(12) United States Patent
Zhou et al.

(10) Patent No.: US 11,026,975 B2
(45) Date of Patent: Jun. 8, 2021

(54) CHIMERIC ANTIGEN RECEPTOR (CAR) BINDING TO BCMA, AND USES THEREOF

(71) Applicants: NANJING IASO BIOTHERAPEUTICS CO., LTD., Jiangsu (CN); INNOVENT BIOLOGICS (SUZHOU) CO., LTD., Jiangsu (CN)

(72) Inventors: Jianfeng Zhou, Jiangsu (CN); Junjian Liu, Jiangsu (CN); Guang Hu, Jiangsu (CN); Yongkun Yang, Jiangsu (CN); Guangrong Meng, Jiangsu (CN); Wenjing Gao, Jiangsu (CN); Yuyu Wang, Jiangsu (CN); Panpan Niu, Jiangsu (CN)

(73) Assignees: Nanjing IASO Biotherapeutics Co., Ltd., Jiangsu (CN); Innovent Biologics (Suzhou) Co., Ltd., Jiangsu (CN)

(*) Notice: Subject to any disclaimer, the term of this patent is extended or adjusted under 35 U.S.C. 154(b) by 0 days.

(21) Appl. No.: 16/650,327

(22) PCT Filed: Jan. 31, 2019

(86) PCT No.: PCT/CN2019/074212
§ 371 (c)(1),
(2) Date: Mar. 24, 2020

(87) PCT Pub. No.: WO2019/149249
PCT Pub. Date: Aug. 8, 2019

(65) Prior Publication Data
US 2020/0376030 A1    Dec. 3, 2020

(30) Foreign Application Priority Data

Feb. 1, 2018  (CN) .......................... 201810100549.6
Oct. 19, 2018 (CN) .......................... 201811228154.0

(51) Int. Cl.
| | | |
|---|---|---|
| *C07K 14/705* | (2006.01) | |
| *C07K 14/715* | (2006.01) | |
| *C07K 16/28* | (2006.01) | |
| *C07K 19/00* | (2006.01) | |
| *C12N 5/10* | (2006.01) | |
| *C12N 15/63* | (2006.01) | |
| *C12N 15/62* | (2006.01) | |
| *A61K 39/395* | (2006.01) | |
| *A61K 35/17* | (2015.01) | |
| *A61P 35/00* | (2006.01) | |
| *C07K 14/54* | (2006.01) | |
| *A61K 39/00* | (2006.01) | |

(52) U.S. Cl.
CPC .......... *A61K 35/17* (2013.01); *A61K 39/3955* (2013.01); *A61P 35/00* (2018.01); *C07K 14/54* (2013.01); *C07K 14/70517* (2013.01); *C07K 14/70575* (2013.01); *C07K 14/715* (2013.01); *C07K 16/28* (2013.01); *C07K 19/00* (2013.01); *C12N 5/10* (2013.01); *C12N 15/62* (2013.01); *C12N 15/63* (2013.01); *A61K 2039/505* (2013.01); *C07K 2317/24* (2013.01); *C07K 2317/56* (2013.01); *C07K 2317/565* (2013.01); *C07K 2319/03* (2013.01)

(58) Field of Classification Search
CPC ........ A61K 2039/505; A61K 39/39558; A61K 39/3955; C07K 16/2878; C07K 2317/24; C07K 2317/73; C07K 2319/00; C07K 2317/76; C07K 16/2896; C07K 2317/565; C07K 16/28; C07K 2317/56
See application file for complete search history.

(56) References Cited

U.S. PATENT DOCUMENTS

2020/0339699 A1* 10/2020 Li .......................... G01N 33/68

FOREIGN PATENT DOCUMENTS

| CN | 104379179 A | 2/2015 |
|---|---|---|
| CN | 105777911 A | 7/2016 |
| CN | 105837693 A | 8/2016 |
| CN | 106687483 A | 5/2017 |
| CN | 107207598 A | 9/2017 |
| JP | 2017538710 A | 12/2017 |
| WO | 2017181119 A2 | 10/2014 |
| WO | 2016094304 A2 | 6/2016 |

OTHER PUBLICATIONS

Ansari et al. Decreased expression of B Cell Maturation Antigen in patients with common variable immunodeficiency. Pediat Allergy Immunol Pulmonol 30(1): 7-13, 2017 (abstract only).*
Bork, P. Powers and pitfalls in sequence analysis: the 70% hurdle. Genome Res 10: 398-400, 2000.*
Bork, P. Go hunting in sequence databases but watch out for the traps. Trends in Genetics 12(10): 425-427, 1996.*
Brenner. S.E. Errors in genome annotation. Trends in Genetics 15:132-133, 1999.*

(Continued)

*Primary Examiner* — Bridget E Bunner
(74) *Attorney, Agent, or Firm* — Honigman LLP; Thomas A. Wootton, Esq.; Jonathan P. O'Brien

(57) ABSTRACT

The invention provides a chimeric antigen receptor (CAR) which can specifically bind to a BCMA protein comprising a BCMA binding structural domain, a transmembrane domain, a co-stimulatory domain, and an intracellular signaling domain. The invention also provides uses of the CAR in treating diseases or conditions linked to the expression of BCMA.

21 Claims, 12 Drawing Sheets
Specification includes a Sequence Listing.

(56) References Cited

OTHER PUBLICATIONS

Brorson et al. Mutational analysis of avidity and fine specificity of anti-levan antibodies, J Immunol 163: 6694-6701, 1999.*
Brummell et al. Probing the combining site of an anti-carbohydrate antibody by saturation-mutagenesis: role of the heavy-chain CDR3 residues. Biochem 32(4): 1180-1187, 1993 (abstract only).*
Casset al. A peptide mimetic of an anti-CD4 monoclonal antibody by rational design. Biochem Biophys Res Comm 307: 198-205, 2003.*
Chen et al. Selection and analysis of an optimized anti-VEGF antibody: crystal structure of an affinity-matured Fab in complex with antigen. J Mol Biol 293: 865-881, 1999.*
Colman, P.M. Effects of amino acid sequence changes on antibody-antigen interactions. Research in Immunol. 145:33-36, 1994.*
De Pascalis et al. Grafting and "abbreviated" complementarity-determining regions containing specificity-determining residues essential for ligand contact to engineer a less immunogenic humanized monoclonal antibody. J Immunol 169: 3076-3084, 2002.*
Doerks et al. Protein annotation: detective work for function prediction. Trends in Genetics 14:248-250, 1998.*
Dogan et al. B-cell maturation antigen expression across hematologic cancers: a systemic literature review. Blood Cancer J 10: 73, 2020 (13 total pages).*
Dotti et al. Design and development of therapies using chimeric angigen receptor-expressing T cells. Immunol Rev 257: 107-126, 2014.*
Han et al. Chimeric antigen receptor-engineered T cells for cancer immunotherapy: progress and challenges. J Hematol Oncol 6: 47, 2013 (7 total pages).*
Holm et al. Functional mapping and single chain construction of the anti-cytokeratin 8 monoclonal antibody TS1. Mol Immunol 44: 1075-1084, 2007.*
Jang et al. The structural basis for DNA binding by an anti-DNA autoantibody. Mol Immunol 35: 1207-1217, 1998.*
Kobayashi et al. Tryptophan H33 plays an important role in pyrimidine (6-4) pyrimidone photoproduct binding by a high-affinity antibody. Protein Engin 12(10): 879-884, 1999.*
MacCallum et al. Antibody-antigen interactions: contact analysis and binding site topography. J Mol Biol 262: 732-745, 1996.*
Ngo et al. "Computational complexity, protein structure prediction, and the Levinthal paradox" in The Protein Folding Problem and Tertiary Structure Prediction, pp. 492-495, 1994.*
Paul, William E., Fundamental Immunology, 3rd Edition, Raven Press, New York, Chapt. 8, pp. 292-295 (1993).*
Rudikoff et al. Single amino acid substitution altering antigen-binding specificity. Proc Natl Acad Sci USA 79: 1979-1983, 1982.*
Skolnick et al. From genes to protein structure and function: novel applications of computational approaches in the genomic era. Trends Biotechnol 18(I):34-39 2000.*
Smith et al. The challenges of genome sequence annotation or "the devil is in the details". Nature Biotechnol 15: 1222-1223, 1997.*
Tokuriki et al. Stability effects of mutations and protein evolvability. Curr Opin Structural Biol 19: 596-604, 2009.*
Vajdos et al. Comprehensive functional maps of the antigen-binding site of an anti-ErbB2 antibody obtained with shotgun scanning mutagenesis. J Mol Biol 320: 415-428, 2002.*
Wells, J.A. Additivity of mutational effects in proteins. Biochemistry 29(37): 8509-8517, 1990.*
PCT/CN2019/074212 International Search Report dated May 5, 2019.

* cited by examiner

SEQUENCE LISTING

<160> NUMBER OF SEQ ID NOS: 52

<210> SEQ ID NO 1
<211> LENGTH: 3
<212> TYPE: PRT
<213> ORGANISM: Artificial Sequence
<220> FEATURE:
<223> OTHER INFORMATION: KOZAK

<400> SEQUENCE: 1

Ala Ala Thr
1

```
<210> SEQ ID NO 2
<211> LENGTH: 9
<212> TYPE: DNA
<213> ORGANISM: Artificial Sequence
<220> FEATURE:
<223> OTHER INFORMATION: KOZAK (nucleotide)

<400> SEQUENCE: 2 gccgccacc                                                             9

<210> SEQ ID NO 3
<211> LENGTH: 21
<212> TYPE: PRT
<213> ORGANISM: Artificial Sequence
<220> FEATURE:
<223> OTHER INFORMATION: CD8a signal peptide

<400> SEQUENCE: 3

Met Ala Leu Pro Val Thr Ala Leu Leu Leu Pro Leu Ala Leu Leu Leu
1               5                   10                  15

His Ala Ala Arg Pro
            20

<210> SEQ ID NO 4
<211> LENGTH: 63
<212> TYPE: DNA
<213> ORGANISM: Artificial Sequence
<220> FEATURE:
<223> OTHER INFORMATION: CD8a signal peptide (nucleotide)

<400> SEQUENCE: 4
atggccctgc ctgtgacagc tctgctcctc cctctggccc tgctgctcca tgccgccaga    60
ccc                                                                  63

<210> SEQ ID NO 5
<211> LENGTH: 9
<212> TYPE: PRT
<213> ORGANISM: Artificial Sequence
<220> FEATURE:
<223> OTHER INFORMATION: HA-tag

<400> SEQUENCE: 5

Tyr Pro Tyr Asp Val Pro Asp Tyr Ala
1               5

<210> SEQ ID NO 6
<211> LENGTH: 27
<212> TYPE: DNA
<213> ORGANISM: Artificial Sequence
<220> FEATURE:
<223> OTHER INFORMATION: HA-tag (nucleotide)

<400> SEQUENCE: 6
tacccatacg atgttccaga ttacgct                                        27

<210> SEQ ID NO 7
<211> LENGTH: 119
<212> TYPE: PRT
<213> ORGANISM: Artificial Sequence
<220> FEATURE:
<223> OTHER INFORMATION: VH

<400> SEQUENCE: 7

Gln Leu Gln Leu Gln Glu Ser Gly Pro Gly Leu Val Lys Pro Ser Glu
1               5                   10                  15
```

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
            35                  40                  45

Trp Ile Gly Ser Ile Ser Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Arg Gly Asp Thr Ile Leu Asp Val Trp Gly Gln Gly
            100                 105                 110

Thr Met Val Thr Val Ser Ser
            115

<210> SEQ ID NO 8
<211> LENGTH: 357
<212> TYPE: DNA
<213> ORGANISM: Artificial Sequence
<220> FEATURE:
<223> OTHER INFORMATION: VH (nucleotide)

<400> SEQUENCE: 8
cagctgcagc tgcaggagtc gggcccagga ctggtgaagc cttcggagac cctgtccctc      60
acctgcactg tctctggtgg ctccatcagc agtagtagtt actactgggg ctggatccgc     120
cagcccccag ggaaggggct ggagtggatt gggagtatct cctatagtgg gagcacctac     180
tacaacccgt ccctcaagag tcgagtcacc atatccgtag acacgtccaa gaaccagttc     240
tccctgaagc tgagttctgt gaccgccgca gacacggcgg tgtactactg cgccagagat     300
cgtggagaca ccatactaga cgtatgggt cagggtacaa tggtcaccgt cagctca        357

<210> SEQ ID NO 9
<211> LENGTH: 10
<212> TYPE: PRT
<213> ORGANISM: Artificial Sequence
<220> FEATURE:
<223> OTHER INFORMATION: HCDR1

<400> SEQUENCE: 9

Gly Gly Ser Ile Ser Ser Ser Tyr Tyr
1               5                   10

<210> SEQ ID NO 10
<211> LENGTH: 7
<212> TYPE: PRT
<213> ORGANISM: Artificial Sequence
<220> FEATURE:
<223> OTHER INFORMATION: HCDR2

<400> SEQUENCE: 10

Ile Ser Tyr Ser Gly Ser Thr
1               5

<210> SEQ ID NO 11
<211> LENGTH: 11
<212> TYPE: PRT
<213> ORGANISM: Artificial Sequence
<220> FEATURE:
<223> OTHER INFORMATION: HCDR3

<400> SEQUENCE: 11

```
Ala Arg Asp Arg Gly Asp Thr Ile Leu Asp Val
1               5                   10
```

<210> SEQ ID NO 12
<211> LENGTH: 30
<212> TYPE: DNA
<213> ORGANISM: Artificial Sequence
<220> FEATURE:
<223> OTHER INFORMATION: HCDR1 (nucleotide)

<400> SEQUENCE: 12
ggtggctcca tcagcagtag tagttactac                              30

<210> SEQ ID NO 13
<211> LENGTH: 21
<212> TYPE: DNA
<213> ORGANISM: Artificial Sequence
<220> FEATURE:
<223> OTHER INFORMATION: HCDR2 (nucleotide)

<400> SEQUENCE: 13
atctcctata gtgggagcac c                                       21

<210> SEQ ID NO 14
<211> LENGTH: 33
<212> TYPE: DNA
<213> ORGANISM: Artificial Sequence
<220> FEATURE:
<223> OTHER INFORMATION: HCDR3 (nucleotide)

<400> SEQUENCE: 14
gccagagatc gtggagacac catactagac gta                          33

<210> SEQ ID NO 15
<211> LENGTH: 106
<212> TYPE: PRT
<213> ORGANISM: Artificial Sequence
<220> FEATURE:
<223> OTHER INFORMATION: VL

<400> SEQUENCE: 15

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys Tyr Asp Leu Leu Thr
                85                  90                  95

Phe Gly Gly Gly Thr Lys Val Glu Ile Lys
            100                 105
```

<210> SEQ ID NO 16
<211> LENGTH: 318
<212> TYPE: DNA
<213> ORGANISM: Artificial Sequence
<220> FEATURE:
<223> OTHER INFORMATION: VL (nucleotide)

-continued

<400> SEQUENCE: 16

```
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcagcaa aaatacgacc tcctcacttt tggcggaggg     300
accaaggttg agatcaaa                                                   318
```

<210> SEQ ID NO 17
<211> LENGTH: 6
<212> TYPE: PRT
<213> ORGANISM: Artificial Sequence
<220> FEATURE:
<223> OTHER INFORMATION: LCDR1

<400> SEQUENCE: 17

Gln Ser Ile Ser Ser Tyr
1               5

<210> SEQ ID NO 18
<211> LENGTH: 3
<212> TYPE: PRT
<213> ORGANISM: Artificial Sequence
<220> FEATURE:
<223> OTHER INFORMATION: LCDR2

<400> SEQUENCE: 18

Ala Ala Ser
1

<210> SEQ ID NO 19
<211> LENGTH: 8
<212> TYPE: PRT
<213> ORGANISM: Artificial Sequence
<220> FEATURE:
<223> OTHER INFORMATION: LCDR3

<400> SEQUENCE: 19

Gln Gln Lys Tyr Asp Leu Leu Thr
1               5

<210> SEQ ID NO 20
<211> LENGTH: 18
<212> TYPE: DNA
<213> ORGANISM: Artificial Sequence
<220> FEATURE:
<223> OTHER INFORMATION: LCDR1 (nucleotide)

<400> SEQUENCE: 20

```
cagagcatta gcagctat                                                    18
```

<210> SEQ ID NO 21
<211> LENGTH: 9
<212> TYPE: DNA
<213> ORGANISM: Artificial Sequence
<220> FEATURE:
<223> OTHER INFORMATION: LCDR2 (nucleotide)

<400> SEQUENCE: 21

```
gctgcatcc                                                               9
```

<210> SEQ ID NO 22

<211> LENGTH: 24
<212> TYPE: DNA
<213> ORGANISM: Artificial Sequence
<220> FEATURE:
<223> OTHER INFORMATION: LCDR3 (nucleotide)

<400> SEQUENCE: 22
cagcaaaaat acgacctcct cact                                          24

<210> SEQ ID NO 23
<211> LENGTH: 18
<212> TYPE: PRT
<213> ORGANISM: Artificial Sequence
<220> FEATURE:
<223> OTHER INFORMATION: Linker (VL-VH)

<400> SEQUENCE: 23

Gly Ser Thr Ser Gly Ser Gly Lys Pro Gly Ser Gly Glu Gly Ser Thr
1               5                   10                  15

Lys Gly

<210> SEQ ID NO 24
<211> LENGTH: 54
<212> TYPE: DNA
<213> ORGANISM: Artificial Sequence
<220> FEATURE:
<223> OTHER INFORMATION: Linker (VL-VH) (nucleotide)

<400> SEQUENCE: 24
ggcagcacca gcggctccgg caagcctggc tctggcgagg gcagcacaaa ggga         54

<210> SEQ ID NO 25
<211> LENGTH: 55
<212> TYPE: PRT
<213> ORGANISM: Artificial Sequence
<220> FEATURE:
<223> OTHER INFORMATION: Structural domain

<400> SEQUENCE: 25

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
                20                  25                  30

Arg Pro Glu Ala Cys Arg Pro Ala Ala Gly Gly Ala Val His Thr Arg
            35                  40                  45

Gly Leu Asp Phe Ala Cys Asp
        50                  55

<210> SEQ ID NO 26
<211> LENGTH: 165
<212> TYPE: DNA
<213> ORGANISM: Artificial Sequence
<220> FEATURE:
<223> OTHER INFORMATION: Structural domain (nucleotide)

<400> SEQUENCE: 26
ttcgtgcccg tgttcctgcc cgccaaacct accaccaccc ctgcccctag acctcccacc   60
ccagccccaa caatcgccag ccagcctctg tctctgcggc ccgaagcctg tagacctgct  120
gccggcggag ccgtgcacac cagaggcctg gacttcgcct gcgac                  165

<210> SEQ ID NO 27
<211> LENGTH: 21
<212> TYPE: PRT

<213> ORGANISM: Artificial Sequence
<220> FEATURE:
<223> OTHER INFORMATION: CD8a transmembrane domain

<400> SEQUENCE: 27

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 28
<211> LENGTH: 63
<212> TYPE: DNA
<213> ORGANISM: Artificial Sequence
<220> FEATURE:
<223> OTHER INFORMATION: CD8a transmembrane domain (nucleotide)

<400> SEQUENCE: 28
atctacatct gggcccctct ggccggcacc tgtggcgtgc tgctgctgag cctggtgatc    60
acc                                                                 63

<210> SEQ ID NO 29
<211> LENGTH: 41
<212> TYPE: PRT
<213> ORGANISM: Artificial Sequence
<220> FEATURE:
<223> OTHER INFORMATION: CD28 costimulatory domain

<400> SEQUENCE: 29

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
            35                  40

<210> SEQ ID NO 30
<211> LENGTH: 123
<212> TYPE: DNA
<213> ORGANISM: Artificial Sequence
<220> FEATURE:
<223> OTHER INFORMATION: CD28 costimulatory domain (nucleotide)

<400> SEQUENCE: 30
agaagcaagc ggagccggct gctgcacagc gactacatga acatgacccc aagacggcct    60
ggccccaccc ggaagcacta ccagccttac gcccctccca gagacttcgc cgcctaccgg   120
tcc                                                                123

<210> SEQ ID NO 31
<211> LENGTH: 42
<212> TYPE: PRT
<213> ORGANISM: Artificial Sequence
<220> FEATURE:
<223> OTHER INFORMATION: 4-1BB costimulatory domain

<400> SEQUENCE: 31

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 32
<211> LENGTH: 126
<212> TYPE: DNA
<213> ORGANISM: Artificial Sequence
<220> FEATURE:
<223> OTHER INFORMATION: 4-1BB costimulatory domain (nucleotide)

<400> SEQUENCE: 32

```
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                                126
```

<210> SEQ ID NO 33
<211> LENGTH: 112
<212> TYPE: PRT
<213> ORGANISM: Artificial Sequence
<220> FEATURE:
<223> OTHER INFORMATION: CD3 intracellular signal transduction domain

<400> SEQUENCE: 33

```
Arg Val Lys Phe Ser Arg Ser Ala Asp Ala Pro Ala Tyr Gln Gln Gly
1               5                   10                  15
Gln Asn Gln Leu Tyr Asn Glu Leu Asn Leu Gly Arg Arg Glu Glu Tyr
            20                  25                  30
Asp Val Leu Asp Lys Arg Arg Gly Arg Asp Pro Glu Met Gly Gly Lys
        35                  40                  45
Pro Arg Arg Lys Asn Pro Gln Glu Gly Leu Tyr Asn Glu Leu Gln Lys
    50                  55                  60
Asp Lys Met Ala Glu Ala Tyr Ser Glu Ile Gly Met Lys Gly Glu Arg
65                  70                  75                  80
Arg Arg Gly Lys Gly His Asp Gly Leu Tyr Gln Gly Leu Ser Thr Ala
                85                  90                  95
Thr Lys Asp Thr Tyr Asp Ala Leu His Met Gln Ala Leu Pro Pro Arg
            100                 105                 110
```

<210> SEQ ID NO 34
<211> LENGTH: 336
<212> TYPE: DNA
<213> ORGANISM: Artificial Sequence
<220> FEATURE:
<223> OTHER INFORMATION: CD3 intracellular signal transduction domain
      (nucleotide)

<400> SEQUENCE: 34

```
agagtgaagt tcagcagatc cgccgacgcc cctgcctacc agcagggaca gaaccagctg      60
tacaacgagc tgaacctggg cagacgggaa gagtacgacg tgctggacaa gcggagaggc     120
cgggaccccg agatgggcgg aaagcccaga cggaagaacc cccaggaagg cctgtataac     180
gaactgcaga agacaagat ggccgaggcc tacagcgaga tcggcatgaa gggcgagcgg     240
aggcgcggca agggccacga tggcctgtac cagggcctga gcaccgccac caaggacacc     300
tacgacgccc tgcacatgca ggccctgccc cccaga                               336
```

<210> SEQ ID NO 35
<211> LENGTH: 18
<212> TYPE: PRT
<213> ORGANISM: Artificial Sequence
<220> FEATURE:
<223> OTHER INFORMATION: cleaving peptide T2A -continued

```
<400> SEQUENCE: 35

Glu Gly Arg Gly Ser Leu Leu Thr Cys Gly Asp Val Glu Glu Asn Pro
1               5                   10                  15

Gly Pro

<210> SEQ ID NO 36
<211> LENGTH: 54
<212> TYPE: DNA
<213> ORGANISM: Artificial Sequence
<220> FEATURE:
<223> OTHER INFORMATION: cleaving peptide T2A (nucleotide)

<400> SEQUENCE: 36
gagggcagag gaagtcttct aacatgcggt gacgtggagg agaatcccgg ccct          54

<210> SEQ ID NO 37
<211> LENGTH: 239
<212> TYPE: PRT
<213> ORGANISM: Artificial Sequence
<220> FEATURE:
<223> OTHER INFORMATION: GFP

<400> SEQUENCE: 37

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 38
<211> LENGTH: 720
<212> TYPE: DNA
<213> ORGANISM: Artificial Sequence
```

<220> FEATURE:
<223> OTHER INFORMATION: GFP (nucleotide)

<400> SEQUENCE: 38

```
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccctgaccta cggcgtgcag tgcttcagcc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacaa cagccacaac gtctatatca tggccgacaa gcagaagaac   480
ggcatcaagg tgaacttcaa gatccgccac aacatcgagg acggcagcgt gcagctcgcc   540
gaccactacc agcagaacac ccccatcggc gacggccccg tgctgctgcc cgacaaccac   600
tacctgagca cccagtccgc cctgagcaaa gaccccaacg agaagcgcga tcacatggtc   660
ctgctggagt tcgtgaccgc cgccgggatc actctcggca tggacgagct gtacaagtaa   720
```

<210> SEQ ID NO 39
<211> LENGTH: 357
<212> TYPE: PRT
<213> ORGANISM: Artificial Sequence
<220> FEATURE:
<223> OTHER INFORMATION: EGFRt

<400> SEQUENCE: 39

| Met | Leu | Leu | Leu | Val | Thr | Ser | Leu | Leu | Leu | Cys | Glu | Leu | Pro | His | Pro |
|---|---|---|---|---|---|---|---|---|---|---|---|---|---|---|---|
| 1 | | | | 5 | | | | | 10 | | | | | 15 | |

| Ala | Phe | Leu | Leu | Ile | Pro | Arg | Lys | Val | Cys | Asn | Gly | Ile | Gly | Ile | Gly |
|---|---|---|---|---|---|---|---|---|---|---|---|---|---|---|---|
| | | | 20 | | | | | 25 | | | | | 30 | | |

| Glu | Phe | Lys | Asp | Ser | Leu | Ser | Ile | Asn | Ala | Thr | Asn | Ile | Lys | His | Phe |
|---|---|---|---|---|---|---|---|---|---|---|---|---|---|---|---|
| | | 35 | | | | | 40 | | | | | 45 | | | |

| Lys | Asn | Cys | Thr | Ser | Ile | Ser | Gly | Asp | Leu | His | Ile | Leu | Pro | Val | Ala |
|---|---|---|---|---|---|---|---|---|---|---|---|---|---|---|---|
| 50 | | | | | 55 | | | | | 60 | | | | | |

| Phe | Arg | Gly | Asp | Ser | Phe | Thr | His | Thr | Pro | Pro | Leu | Asp | Pro | Gln | Glu |
|---|---|---|---|---|---|---|---|---|---|---|---|---|---|---|---|
| 65 | | | | | 70 | | | | | 75 | | | | | 80 |

| Leu | Asp | Ile | Leu | Lys | Thr | Val | Lys | Glu | Ile | Thr | Gly | Phe | Leu | Leu | Ile |
|---|---|---|---|---|---|---|---|---|---|---|---|---|---|---|---|
| | | | | 85 | | | | | 90 | | | | | 95 | |

| Gln | Ala | Trp | Pro | Glu | Asn | Arg | Thr | Asp | Leu | His | Ala | Phe | Glu | Asn | Leu |
|---|---|---|---|---|---|---|---|---|---|---|---|---|---|---|---|
| | | | 100 | | | | | 105 | | | | | 110 | | |

| Glu | Ile | Ile | Arg | Gly | Arg | Thr | Lys | Gln | His | Gly | Gln | Phe | Ser | Leu | Ala |
|---|---|---|---|---|---|---|---|---|---|---|---|---|---|---|---|
| | | 115 | | | | | 120 | | | | | 125 | | | |

| Val | Val | Ser | Leu | Asn | Ile | Thr | Ser | Leu | Gly | Leu | Arg | Ser | Leu | Lys | Glu |
|---|---|---|---|---|---|---|---|---|---|---|---|---|---|---|---|
| | 130 | | | | | 135 | | | | | 140 | | | | |

| Ile | Ser | Asp | Gly | Asp | Val | Ile | Ile | Ser | Gly | Asn | Lys | Asn | Leu | Cys | Tyr |
|---|---|---|---|---|---|---|---|---|---|---|---|---|---|---|---|
| 145 | | | | | 150 | | | | | 155 | | | | | 160 |

| Ala | Asn | Thr | Ile | Asn | Trp | Lys | Lys | Leu | Phe | Gly | Thr | Ser | Gly | Gln | Lys |
|---|---|---|---|---|---|---|---|---|---|---|---|---|---|---|---|
| | | | | 165 | | | | | 170 | | | | | 175 | |

| Thr | Lys | Ile | Ile | Ser | Asn | Arg | Gly | Glu | Asn | Ser | Cys | Lys | Ala | Thr | Gly |
|---|---|---|---|---|---|---|---|---|---|---|---|---|---|---|---|
| | | | 180 | | | | | 185 | | | | | 190 | | |

| Gln | Val | Cys | His | Ala | Leu | Cys | Ser | Pro | Glu | Gly | Cys | Trp | Gly | Pro | Glu |
|---|---|---|---|---|---|---|---|---|---|---|---|---|---|---|---|
| | | 195 | | | | | 200 | | | | | 205 | | | |

| Pro | Arg | Asp | Cys | Val | Ser | Cys | Arg | Asn | Val | Ser | Arg | Gly | Arg | Glu | Cys |
|---|---|---|---|---|---|---|---|---|---|---|---|---|---|---|---|

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
            245                 250                 255

Asn Ile Thr Cys Thr Gly Arg Gly Pro Asp Asn Cys Ile Gln Cys Ala
        260                 265                 270

His Tyr Ile Asp Gly Pro His Cys Val Lys Thr Cys Pro Ala Gly Val
    275                 280                 285

Met Gly Glu Asn Asn Thr Leu Val Trp Lys Tyr Ala Asp Ala Gly His
290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Leu Val Val Ala Leu Gly
            340                 345                 350

Ile Gly Leu Phe Met
        355

<210> SEQ ID NO 40
<211> LENGTH: 1071
<212> TYPE: DNA
<213> ORGANISM: Artificial Sequence
<220> FEATURE:
<223> OTHER INFORMATION: EGFRt (nucleotide)

<400> SEQUENCE: 40
atgctgctgc tcgtgacctc tttactgtta tgtgagctgc cccacccgc ttttttactg      60 atccctcgta aggtgtgtaa cggaatcggc attggcgagt caaggactc tttaagcatc     120 aacgccacaa acatcaagca cttcaagaat tgtacctcca tcagcggcga tttacacatt     180
ctccccgtgg cttttcgtgg cgattccttc acccacaccc ccctctgga ccccaagag      240 ctggacattt taaaaaccgt gaaggagatc accggcttc tgctgatcca agcttggccc     300
gagaatcgta ccgacctcca cgccttcgag aatttagaga ttattcgtgg aaggaccaag     360
cagcacggcc agttctcttt agccgtcgtg tctttaaaca ttaccagcct cggtttaagg     420
tctttaaagg agattagcga cggcgacgtg atcatctccg caacaagaa cctctgctac     480 gccaacacca tcaactggaa gaagctgttc ggaaccagcg gccaaaagac caagatcatc     540
agcaatcgtg agagaactc ttgtaaggcc actggtcaag tttgccacgc cctctgtagc     600
cccgaaggat gttggggccc cgagcctagg gactgtgtta gctgcagaaa cgtgagcaga     660
ggcagagagt gtgtggacaa atgcaattta ctggaaggag agcctaggga gttcgtggag     720
aacagcgaat gtatccagtg ccaccccgag tgtttacctc aagccatgaa catcacttgt     780
accggaaggg gccccgataa ctgcatccaa tgcgcccact acatcgacgg accccactgc     840
gtgaaaactt gtcccgccgg agtgatggga gagaataaca ctttagtgtg gaagtacgcc     900
gacgctggcc acgtctgcca tctgtgccac cccaactgta cctacggctg cactggtccc     960
ggtttagagg gatgtcctac caacggcccc aagatccct ccatcgccac cggaatggtg    1020
ggcgctctgt tattactgct ggtggtggct ctgggcatcg gtttattcat g             1071

<210> SEQ ID NO 41
<211> LENGTH: 246
<212> TYPE: PRT

<213> ORGANISM: Artificial Sequence
<220> FEATURE:
<223> OTHER INFORMATION: scFv0008

<400> SEQUENCE: 41

Asp Ile Val Leu Thr Gln Ser Pro Pro Ser Leu Ala Met Ser Leu Gly
1               5                   10                  15

Lys Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Pro Pro
        35                  40                  45

Thr Leu Leu Ile Gln Leu Ala Ser Asn Val Gln Thr Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Glu Asp Asp Val Ala Val Tyr Tyr Cys Leu Gln Ser Arg
                85                  90                  95

Thr Ile Pro Arg Thr Phe Gly Gly Gly Thr Lys Leu Glu Ile Lys Gly
            100                 105                 110

Ser Thr Ser Gly Ser Gly Lys Pro Gly Ser Gly Glu Gly Ser Thr Lys
        115                 120                 125

Gly Gln Ile Gln Leu Val Gln Ser Gly Pro Glu Leu Lys Lys Pro Gly
    130                 135                 140

Glu Thr Val Lys Ile Ser Cys Lys Ala Ser Gly Tyr Thr Phe Thr Asp
145                 150                 155                 160

Tyr Ser Ile Asn Trp Val Lys Arg Ala Pro Gly Lys Gly Leu Lys Trp
                165                 170                 175

Met Gly Trp Ile Asn Thr Glu Thr Arg Glu Pro Ala Tyr Ala Tyr Asp
            180                 185                 190

Phe Arg Gly Arg Phe Ala Phe Ser Leu Glu Thr Ser Ala Ser Thr Ala
        195                 200                 205

Tyr Leu Gln Ile Asn Asn Leu Lys Tyr Glu Asp Thr Ala Thr Tyr Phe
    210                 215                 220

Cys Ala Leu Asp Tyr Ser Tyr Ala Met Asp Tyr Trp Gly Gln Gly Thr
225                 230                 235                 240

Ser Val Thr Val Ser Ser
                245

<210> SEQ ID NO 42
<211> LENGTH: 738
<212> TYPE: DNA
<213> ORGANISM: Artificial Sequence
<220> FEATURE:
<223> OTHER INFORMATION: scFv0008 (nucleotide)

<400> SEQUENCE: 42
gacatcgtgc tgacccagag cccccccagc ctggccatgt ctctgggcaa gagagccacc      60
atcagctgcc gggccagcga gagcgtgacc atcctgggca gccacctgat ccactggtat     120
cagcagaagc ccggccagcc ccccaccctg ctgatccagc tcgccagcaa tgtgcagacc     180
ggcgtgcccg ccagattcag cggcagcggc agcagaaccg acttcaccct gaccatcgac     240
cccgtggaag aggacgacgt ggccgtgtac tactgcctgc agagccggac catcccccgg     300 accttttggcg gaggcaccaa actggaaatc aagggcagca ccagcggctc cggcaagcct    360
ggctctggcg agggcagcac aaagggacag attcagctgg tgcagagcgg ccctgagctg     420
aagaaacccg gcgagacagt gaagatcagc tgcaaggcct ccggctacac cttcaccgac     480

```
tacagcatca actgggtgaa aagagcccct ggcaagggcc tgaagtggat gggctggatc        540
aacaccgaga caagagagcc cgcctacgcc tacgacttcc ggggcagatt cgccttcagc        600
ctggaaacca gcgccagcac cgcctacctg cagatcaaca acctgaagta cgaggacacc        660
gccacctact tttgcgccct ggactacagc tacgccatgg actactgggg ccagggcacc        720
agcgtgaccg tgtccagc                                                     738
```

```
<210> SEQ ID NO 43
<211> LENGTH: 243
<212> TYPE: PRT
<213> ORGANISM: Artificial Sequence
<220> FEATURE:
<223> OTHER INFORMATION: scFv0026

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys Tyr Asp Leu Leu Thr
                85                  90                  95

Phe Gly Gly Gly Thr Lys Val Glu Ile Lys Gly Ser Thr Ser Gly Ser
            100                 105                 110

Gly Lys Pro Gly Ser Gly Glu Gly Ser Thr Lys Gly Gln Leu Gln Leu
        115                 120                 125

Gln Glu Ser Gly Pro Gly Leu Val Lys Pro Ser Glu Thr Leu Ser Leu
    130                 135                 140

Thr Cys Thr Val Ser Gly Gly Ser Ile Ser Ser Ser Ser Tyr Tyr Trp
145                 150                 155                 160

Gly Trp Ile Arg Gln Pro Pro Gly Lys Gly Leu Glu Trp Ile Gly Ser
                165                 170                 175

Ile Ser Tyr Ser Gly Ser Thr Tyr Tyr Asn Pro Ser Leu Lys Ser Arg
            180                 185                 190

Val Thr Ile Ser Val Asp Thr Ser Lys Asn Gln Phe Ser Leu Lys Leu
        195                 200                 205

Ser Ser Val Thr Ala Ala Asp Thr Ala Val Tyr Tyr Cys Ala Arg Asp
    210                 215                 220

Arg Gly Asp Thr Ile Leu Asp Val Trp Gly Gln Gly Thr Met Val Thr
225                 230                 235                 240

Val Ser Ser
```

```
<210> SEQ ID NO 44
<211> LENGTH: 729
<212> TYPE: DNA
<213> ORGANISM: Artificial Sequence
<220> FEATURE:
<223> OTHER INFORMATION: scFv0026 (nucleotide)

<400> SEQUENCE: 44
gacatccaga tgacccagtc tccatcctcc ctgtctgcat ctgtaggaga cagagtcacc         60
```

```
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcagcaa aaatacgacc tcctcacttt tggcggaggg    300
accaaggttg agatcaaagg cagcaccagc ggctccggca agcctggctc tggcgagggc    360
agcacaaagg acagctgca gctgcaggag tcgggcccag actggtgaa gccttcggag     420 accctgtccc tcacctgcac tgtctctggt ggctccatca gcagtagtag ttactactgg    480
ggctggatcc gccagccccc agggaagggg ctggagtgga ttgggagtat ctcctatagt    540
gggagcacct actacaaccc gtccctcaag agtcgagtca ccatatccgt agacacgtcc    600
aagaaccagt tctccctgaa gctgagttct gtgaccgccg cagacacggc ggtgtactac    660
tgcgccagag atcgtggaga caccatacta gacgtatggg gtcagggtac aatggtcacc    720
gtcagctca                                                           729

<210> SEQ ID NO 45
<211> LENGTH: 482
<212> TYPE: PRT
<213> ORGANISM: Artificial Sequence
<220> FEATURE:
<223> OTHER INFORMATION: CAR0009

<400> SEQUENCE: 45

Asp Ile Val Leu Thr Gln Ser Pro Pro Ser Leu Ala Met Ser Leu Gly
1               5                   10                  15

Lys Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Pro Pro
        35                  40                  45

Thr Leu Leu Ile Gln Leu Ala Ser Asn Val Gln Thr Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Glu Asp Val Ala Val Tyr Tyr Cys Leu Gln Ser Arg
                85                  90                  95

Thr Ile Pro Arg Thr Phe Gly Gly Gly Thr Lys Leu Glu Ile Lys Gly
            100                 105                 110

Ser Thr Ser Gly Ser Gly Lys Pro Gly Ser Gly Glu Gly Ser Thr Lys
        115                 120                 125

Gly Gln Ile Gln Leu Val Gln Ser Gly Pro Glu Leu Lys Lys Pro Gly
    130                 135                 140

Glu Thr Val Lys Ile Ser Cys Lys Ala Ser Gly Tyr Thr Phe Thr Asp
145                 150                 155                 160

Tyr Ser Ile Asn Trp Val Lys Arg Ala Pro Gly Lys Gly Leu Lys Trp
                165                 170                 175

Met Gly Trp Ile Asn Thr Glu Thr Arg Glu Pro Ala Tyr Ala Tyr Asp
            180                 185                 190

Phe Arg Gly Arg Phe Ala Phe Ser Leu Glu Thr Ser Ala Ser Thr Ala
        195                 200                 205

Tyr Leu Gln Ile Asn Asn Leu Lys Tyr Glu Asp Thr Ala Thr Tyr Phe
    210                 215                 220

Cys Ala Leu Asp Tyr Ser Tyr Ala Met Asp Tyr Trp Gly Gln Gly Thr
225                 230                 235                 240
```

```
Ser Val Thr Val Ser Ser Phe Val Pro Val Phe Leu Pro Ala Lys Pro
                245                 250                 255

Thr Thr Thr Pro Ala Pro Arg Pro Pro Thr Pro Ala Pro Thr Ile Ala
            260                 265                 270

Ser Gln Pro Leu Ser Leu Arg Pro Glu Ala Cys Arg Pro Ala Ala Gly
        275                 280                 285

Gly Ala Val His Thr Arg Gly Leu Asp Phe Ala Cys Asp Ile Tyr Ile
    290                 295                 300

Trp Ala Pro Leu Ala Gly Thr Cys Gly Val Leu Leu Leu Ser Leu Val
305                 310                 315                 320

Ile Thr Leu Tyr Cys Asn His Arg Asn Arg Ser Lys Arg Ser Arg Leu
                325                 330                 335

Leu His Ser Asp Tyr Met Asn Met Thr Pro Arg Arg Pro Gly Pro Thr
            340                 345                 350

Arg Lys His Tyr Gln Pro Tyr Ala Pro Pro Arg Asp Phe Ala Ala Tyr
        355                 360                 365

Arg Ser Arg Val Lys Phe Ser Arg Ser Ala Asp Ala Pro Ala Tyr Gln
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
    450                 455                 460

Thr Ala Thr Lys Asp Thr Tyr Asp Ala Leu His Met Gln Ala Leu Pro
465                 470                 475                 480

Pro Arg

<210> SEQ ID NO 46
<211> LENGTH: 1446
<212> TYPE: DNA
<213> ORGANISM: Artificial Sequence
<220> FEATURE:
<223> OTHER INFORMATION: CAR0009 (nucleotide)

<400> SEQUENCE: 46
gacatcgtgc tgacccagag ccccccccagc ctggccatgt ctctgggcaa gagagccacc      60
atcagctgcc gggccagcga gagcgtgacc atcctgggca gccacctgat ccactgtgtat     120 cagcagaagc ccggccagcc ccccaccctg ctgatccagc tcgccagcaa tgtgcagacc     180
ggcgtgcccg ccagattcag cggcagcggc agcagaaccg acttcaccct gaccatcgac     240
cccgtggaag aggacgacgt ggccgtgtac tactgcctgc agagccggac catccccgg      300 accttttggcg gaggcaccaa actggaaatc aagggcagca ccagcggctc cggcaagcct     360
ggctctggcg agggcagcac aaagggacag attcagctgg tgcagagcgg ccctgagctg     420
aagaaacccg gcgagacagt gaagatcagc tgcaaggcct ccggctacac cttcaccgac     480
tacagcatca ctgggtgaa aagagcccct ggcaagggcc tgaagtggat gggctggatc     540
aacaccgaga acagagagcc cgcctacgcc tacgacttcc ggggcagatt cgccttcagc     600
ctggaaacca gcgccagcac cgcctacctg cagatcaaca acctgaagta cgaggacacc     660
```

```
gccacctact tttgcgccct ggactacagc tacgccatgg actactgggg ccagggcacc    720
agcgtgaccg tgtccagctt cgtgcccgtg ttcctgcccg ccaaacctac caccacccct    780
gcccctagac ctcccacccc agccccaaca atcgccagcc agcctctgtc tctgcggccc    840
gaagcctgta gacctgctgc cggcggagcc gtgcacacca gaggcctgga cttcgcctgc    900
gacatctaca tctgggcccc tctggccggc acctgtggcg tgctgctgct gagcctggtg    960
atcaccctgt actgcaacca ccggaacaga agcaagcgga gccggctgct gcacagcgac   1020
tacatgaaca tgaccccaag acggcctggc cccacccgga agcactacca gccttacgcc   1080
cctcccagag acttcgccgc ctaccggtcc agagtgaagt tcagcagatc cgccgacgcc   1140
cctgcctacc agcagggaca gaaccagctg tacaacgagc tgaacctggg cagacgggaa   1200
gagtacgacg tgctggacaa gcggagaggc cgggaccccg agatgggcgg aaagcccaga   1260
cggaagaacc cccaggaagg cctgtataac gaactgcaga agacaagat ggccgaggcc    1320
tacagcgaga tcggcatgaa gggcgagcgg aggcgcggca agggccacga tggcctgtac   1380
cagggcctga gcaccgccac caaggacacc tacgacgccc tgcacatgca ggccctgccc   1440
cccaga                                                              1446

<210> SEQ ID NO 47
<211> LENGTH: 491
<212> TYPE: PRT
<213> ORGANISM: Artificial Sequence
<220> FEATURE:
<223> OTHER INFORMATION: CAR0041

<400> SEQUENCE: 47
```

Tyr Pro Tyr Asp Val Pro Asp Tyr Ala Asp Ile Val Leu Thr Gln Ser
1               5                   10                  15

Pro Pro Ser Leu Ala Met Ser Leu Gly Lys Arg Ala Thr Ile Ser Cys
            20                  25                  30

Arg Ala Ser Glu Ser Val Thr Ile Leu Gly Ser His Leu Ile His Trp
        35                  40                  45

Tyr Gln Gln Lys Pro Gly Gln Pro Pro Thr Leu Leu Ile Gln Leu Ala
    50                  55                  60

Ser Asn Val Gln Thr Gly Val Pro Ala Arg Phe Ser Gly Ser Gly Ser
65                  70                  75                  80

Arg Thr Asp Phe Thr Leu Thr Ile Asp Pro Val Glu Glu Asp Asp Val
                85                  90                  95

Ala Val Tyr Tyr Cys Leu Gln Ser Arg Thr Ile Pro Arg Thr Phe Gly
            100                 105                 110

Gly Gly Thr Lys Leu Glu Ile Lys Gly Ser Thr Ser Gly Ser Gly Lys
        115                 120                 125

Pro Gly Ser Gly Glu Gly Ser Thr Lys Gly Gln Ile Gln Leu Val Gln
    130                 135                 140

Ser Gly Pro Glu Leu Lys Lys Pro Gly Glu Thr Val Lys Ile Ser Cys
145                 150                 155                 160

Lys Ala Ser Gly Tyr Thr Phe Thr Asp Tyr Ser Ile Asn Trp Val Lys
                165                 170                 175

Arg Ala Pro Gly Lys Gly Leu Lys Trp Met Gly Trp Ile Asn Thr Glu
            180                 185                 190

Thr Arg Glu Pro Ala Tyr Ala Tyr Asp Phe Arg Gly Arg Phe Ala Phe
        195                 200                 205

Ser Leu Glu Thr Ser Ala Ser Thr Ala Tyr Leu Gln Ile Asn Asn Leu

```
Lys Tyr Glu Asp Thr Ala Thr Tyr Phe Cys Ala Leu Asp Tyr Ser Tyr
225                 230                 235                 240

Ala Met Asp Tyr Trp Gly Gln Gly Thr Ser Val Thr Val Ser Ser Phe
            245                 250                 255

Val Pro Val Phe Leu Pro Ala Lys Pro Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Asn His
                325                 330                 335

Arg Asn Arg Ser Lys Arg Ser Arg Leu Leu His Ser Asp Tyr Met Asn
            340                 345                 350

Met Thr Pro Arg Arg Pro Gly Pro Thr Arg Lys His Tyr Gln Pro Tyr
        355                 360                 365

Ala Pro Pro Arg Asp Phe Ala Ala Tyr Arg Ser Arg Val Lys Phe Ser
    370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 48
<211> LENGTH: 1473
<212> TYPE: DNA
<213> ORGANISM: Artificial Sequence
<220> FEATURE:
<223> OTHER INFORMATION: CAR0041 (nucleotide)

<400> SEQUENCE: 48
tacccatacg atgttccaga ttacgctgac atcgtgctga cccagagccc ccccagcctg      60
gccatgtctc tgggcaagag agccaccatc agctgccggg ccagcgagag cgtgaccatc     120
ctgggcagcc acctgatcca ctggtatcag cagaagcccg gccagccccc caccctgctg     180
atccagctcg ccagcaatgt gcagaccggc gtgcccgcca gattcagcgg cagcggcagc     240
agaaccgact tcaccctgac catcgacccc gtggaagagg acgacgtggc cgtgtactac     300
tgcctgcaga gccggaccat ccccggacc tttggcggag caccaaaact ggaaatcaag     360
ggcagcacca gcggctccgg caagcctggc tctggcgagg gcagcacaaa gggacagatt     420
cagctggtgc agagcggccc tgagctgaag aaacccggcg agacagtgaa gatcagctgc     480
```

```
aaggcctccg gctacacctt caccgactac agcatcaact gggtgaaaag agcccctggc    540
aagggcctga agtggatggg ctggatcaac accgagacaa gagagcccgc ctacgcctac    600
gacttccggg gcagattcgc cttcagcctg aaaccagcg ccagcaccgc ctacctgcag     660
atcaacaacc tgaagtacga ggacaccgcc acctactttt gcgccctgga ctacagctac    720
gccatggact actggggcca gggcaccagc gtgaccgtgt ccagcttcgt gcccgtgttc    780
ctgcccgcca aacctaccac cacccctgcc cctagacctc ccaccccagc ccaacaatc     840 gccagccagc ctctgtctct gcggcccgaa gcctgtagac ctgctgccgg cggagccgtg    900
cacaccagag gcctggactt cgcctgcgac atctacatct gggcccctct ggccggcacc    960
tgtggcgtgc tgctgctgag cctggtgatc accctgtact gcaaccaccg gaacagaagc    1020
aagcggagcc ggctgctgca cagcgactac atgaacatga ccccaagacg gcctggcccc    1080
acccggaagc actaccagcc ttacgcccct cccagagact cgccgcctac ccggtccaga    1140
gtgaagttca gcagatccgc cgacgcccct gcctaccagc agggacagaa ccagctgtac    1200
aacgagctga acctgggcag acgggaagag tacgacgtgc tggacaagcg agaggccgg    1260 gaccccgaga tgggcggaaa gcccagacgg aagaaccccc aggaaggcct gtataacgaa    1320
ctgcagaaag acaagatggc cgaggcctac agcgagatcg gcatgaaggg cgagcggagg    1380
cgcggcaagg ccacgatgg cctgtaccag ggcctgagca ccgccaccaa ggacacctac    1440
gacgccctgc acatgcaggc cctgcccccc aga                                 1473
```

<210> SEQ ID NO 49
<211> LENGTH: 488
<212> TYPE: PRT
<213> ORGANISM: Artificial Sequence
<220> FEATURE:
<223> OTHER INFORMATION: CAR0037

<400> SEQUENCE: 49

```
Tyr Pro Tyr Asp Val Pro Asp Tyr Ala Asp Ile Gln Met Thr Gln Ser
1               5                   10                  15

Pro Ser Ser Leu Ser Ala Ser Val Gly Asp Arg Val Thr Ile Thr Cys
            20                  25                  30

Arg Ala Ser Gln Ser Ile Ser Ser Tyr Leu Asn Trp Tyr Gln Gln Lys
        35                  40                  45

Pro Gly Lys Ala Pro Lys Leu Leu Ile Tyr Ala Ala Ser Ser Leu Gln
    50                  55                  60

Ser Gly Val Pro Ser Arg Phe Ser Gly Ser Gly Ser Gly Thr Asp Phe
65                  70                  75                  80

Thr Leu Thr Ile Ser Ser Leu Gln Pro Glu Asp Phe Ala Thr Tyr Tyr
                85                  90                  95

Cys Gln Gln Lys Tyr Asp Leu Leu Thr Phe Gly Gly Gly Thr Lys Val
            100                 105                 110

Glu Ile Lys Gly Ser Thr Ser Gly Ser Gly Lys Pro Gly Ser Gly Glu
        115                 120                 125

Gly Ser Thr Lys Gly Gln Leu Gln Leu Gln Glu Ser Gly Pro Gly Leu
    130                 135                 140

Val Lys Pro Ser Glu Thr Leu Ser Leu Thr Cys Thr Val Ser Gly Gly
145                 150                 155                 160

Ser Ile Ser Ser Ser Ser Tyr Tyr Trp Gly Trp Ile Arg Gln Pro Pro
                165                 170                 175

Gly Lys Gly Leu Glu Trp Ile Gly Ser Ile Ser Tyr Ser Gly Ser Thr
            180                 185                 190
```

```
Tyr Tyr Asn Pro Ser Leu Lys Ser Arg Val Thr Ile Ser Val Asp Thr
            195                 200                 205

Ser Lys Asn Gln Phe Ser Leu Lys Leu Ser Ser Val Thr Ala Ala Asp
        210                 215                 220

Thr Ala Val Tyr Tyr Cys Ala Arg Asp Arg Gly Asp Thr Ile Leu Asp
225                 230                 235                 240

Val Trp Gly Gln Gly Thr Met Val Thr Val Ser Ser Phe Val Pro Val
                245                 250                 255

Phe Leu Pro Ala Lys Pro Thr Thr Pro Ala Pro Arg Pro Pro Thr
            260                 265                 270

Pro Ala Pro Thr Ile Ala Ser Gln Pro Leu Ser Leu Arg Pro Glu Ala
            275                 280                 285

Cys Arg Pro Ala Ala Gly Gly Ala Val His Thr Arg Gly Leu Asp Phe
290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Asn His Arg Asn Arg
                325                 330                 335

Ser Lys Arg Ser Arg Leu Leu His Ser Asp Tyr Met Asn Met Thr Pro
            340                 345                 350

Arg Arg Pro Gly Pro Thr Arg Lys His Tyr Gln Pro Tyr Ala Pro Pro
            355                 360                 365

Arg Asp Phe Ala Ala Tyr Arg Ser Arg Val Lys Phe Ser Arg Ser Ala
        370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
            435                 440                 445

Glu Ile Gly Met Lys Gly Glu Arg Arg Arg Gly Lys Gly His Asp Gly
        450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485

<210> SEQ ID NO 50
<211> LENGTH: 1464
<212> TYPE: DNA
<213> ORGANISM: Artificial Sequence
<220> FEATURE:
<223> OTHER INFORMATION: CAR0037 (nucleotide)

<400> SEQUENCE: 50
tacccatacg atgttccaga ttacgctgac atccagatga cccagtctcc atcctccctg        60
tctgcatctg taggagacag agtcaccatc acttgccggg caagtcagag cattagcagc       120
tatttaaatt ggtatcagca gaaaccaggg aaagccccta agctcctgat ctatgctgca       180
tccagtttgc aaagtggggt cccatcaagg ttcagtggca gtggatctgg gacagatttc       240
actctcacca tcagcagtct gcaacctgaa gattttgcaa cttactactg tcagcaaaaa       300
tacgacctcc tcactttggg cggagggacc aaggttgaga tcaaaggcag caccagcggc       360
```

-continued

```
tccggcaagc ctggctctgg cgagggcagc acaaagggac agctgcagct gcaggagtcg      420
ggcccaggac tggtgaagcc ttcggagacc ctgtccctca cctgcactgt ctctggtggc      480
tccatcagca gtagtagtta ctactggggc tggatccgcc agccccagg gaaggggctg       540 gagtggattg ggagtatctc ctatagtggg agcacctact acaacccgtc cctcaagagt      600
cgagtcacca tatccgtaga cacgtccaag aaccagttct ccctgaagct gagttctgtg      660
accgccgcag acacggcggt gtactactgc gccagagatc gtggagacac catactagac      720
gtatggggtc agggtacaat ggtcaccgtc agctcattcg tgcccgtgtt cctgcccgcc      780
aaacctacca ccaccctgc ccctagacct cccaccccag cccaacaat cgccagccag        840 cctctgtctc tgcggcccga agcctgtaga cctgctgccg gcggagccgt gcacaccaga      900
ggcctggact cgcctgcgca catctacatc tgggcccctc tggccggcac ctgtggcgtg      960
ctgctgctga gcctggtgat caccctgtac tgcaaccacc ggaacagaag caagcggagc     1020
cggctgctgc acagcgacta catgaacatg accccaagac ggcctggccc cacccggaag     1080
cactaccagc cttacgcccc tcccagagac ttcgccgcct accggtccag agtgaagttc     1140
agcagatccg ccgacgcccc tgcctaccag cagggacaga accagctgta caacgagctg     1200
aacctgggca gacgggaaga gtacgacgtg ctggacaagc ggagaggccg ggaccccgag     1260
atgggcggaa agcccagacg gaagaacccc caggaaggcc tgtataacga actgcagaaa     1320
gacaagatgg ccgaggccta cagcgagatc ggcatgaagg gcgagcggag gcgcggcaag     1380
ggccacgatg gcctgtacca gggcctgagc accgccacca aggacaccta cgacgccctg     1440
cacatgcagg ccctgcccccc caga                                             1464
```

<210> SEQ ID NO 51
<211> LENGTH: 480
<212> TYPE: PRT
<213> ORGANISM: Artificial Sequence
<220> FEATURE:
<223> OTHER INFORMATION: CAR0085

<400> SEQUENCE: 51

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys Tyr Asp Leu Leu Thr
                85                  90                  95

Phe Gly Gly Gly Thr Lys Val Glu Ile Lys Gly Ser Thr Ser Gly Ser
            100                 105                 110

Gly Lys Pro Gly Ser Gly Glu Gly Ser Thr Lys Gly Gln Leu Gln Leu
        115                 120                 125

Gln Glu Ser Gly Pro Gly Leu Val Lys Pro Ser Glu Thr Leu Ser Leu
    130                 135                 140

Thr Cys Thr Val Ser Gly Gly Ser Ile Ser Ser Ser Ser Tyr Tyr Trp
145                 150                 155                 160
```

```
Gly Trp Ile Arg Gln Pro Pro Gly Lys Gly Leu Glu Trp Ile Gly Ser
            165                 170                 175
Ile Ser Tyr Ser Gly Ser Thr Tyr Tyr Asn Pro Ser Leu Lys Ser Arg
        180                 185                 190
Val Thr Ile Ser Val Asp Thr Ser Lys Asn Gln Phe Ser Leu Lys Leu
    195                 200                 205
Ser Ser Val Thr Ala Ala Asp Thr Ala Val Tyr Tyr Cys Ala Arg Asp
210                 215                 220
Arg Gly Asp Thr Ile Leu Asp Val Trp Gly Gln Gly Thr Met Val Thr
225                 230                 235                 240
Val Ser Ser Phe Val Pro Val Phe Leu Pro Ala Lys Pro Thr Thr Thr
                245                 250                 255
Pro Ala Pro Arg Pro Pro Thr Pro Ala Pro Thr Ile Ala Ser Gln Pro
            260                 265                 270
Leu Ser Leu Arg Pro Glu Ala Cys Arg Pro Ala Ala Gly Gly Ala Val
        275                 280                 285
His Thr Arg Gly Leu Asp Phe Ala Cys Asp Ile Tyr Ile Trp Ala Pro
    290                 295                 300
Leu Ala Gly Thr Cys Gly Val Leu Leu Leu Ser Leu Val Ile Thr Leu
305                 310                 315                 320
Tyr Cys Asn His Arg Asn Lys Arg Gly Arg Lys Lys Leu Leu Tyr Ile
                325                 330                 335
Phe Lys Gln Pro Phe Met Arg Pro Val Gln Thr Thr Gln Glu Glu Asp
            340                 345                 350
Gly Cys Ser Cys Arg Phe Pro Glu Glu Glu Glu Gly Gly Cys Glu Leu
        355                 360                 365
Arg Val Lys Phe Ser Arg Ser Ala Asp Ala Pro Ala Tyr Gln Gln Gly
    370                 375                 380
Gln Asn Gln Leu Tyr Asn Glu Leu Asn Leu Gly Arg Arg Glu Glu Tyr
385                 390                 395                 400
Asp Val Leu Asp Lys Arg Gly Arg Asp Pro Glu Met Gly Gly Lys
                405                 410                 415
Pro Arg Arg Lys Asn Pro Gln Glu Gly Leu Tyr Asn Glu Leu Gln Lys
            420                 425                 430
Asp Lys Met Ala Glu Ala Tyr Ser Glu Ile Gly Met Lys Gly Glu Arg
        435                 440                 445
Arg Arg Gly Lys Gly His Asp Gly Leu Tyr Gln Gly Leu Ser Thr Ala
    450                 455                 460
Thr Lys Asp Thr Tyr Asp Ala Leu His Met Gln Ala Leu Pro Pro Arg
465                 470                 475                 480

<210> SEQ ID NO 52
<211> LENGTH: 1440
<212> TYPE: DNA
<213> ORGANISM: Artificial Sequence
<220> FEATURE:
<223> OTHER INFORMATION: CAR0085 (nucleotide)

<400> SEQUENCE: 52
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcagcaa aaatacgacc tcctcacttt tggcggaggg     300
```

-continued

```
accaaggttg agatcaaagg cagcaccagc ggctccggca agcctggctc tggcgagggc    360
agcacaaagg gacagctgca gctgcaggag tcgggcccag gactggtgaa gccttcggag    420
accctgtccc tcacctgcac tgtctctggt ggctccatca gcagtagtag ttactactgg    480
ggctggatcc gccagccccc agggaagggg ctggagtgga ttgggagtat ctcctatagt    540
gggagcacct actacaaccc gtccctcaag agtcgagtca ccatatccgt agacacgtcc    600
aagaaccagt tctccctgaa gctgagttct gtgaccgccg cagacacggc ggtgtactac    660
tgcgccagag atcgtggaga caccatacta gacgtatggg gtcagggtac aatggtcacc    720
gtcagctcat tcgtgcccgt gttcctgccc gccaaaccta ccaccacccc tgcccctaga    780
cctcccaccc cagccccaac aatcgccagc cagcctctgt ctctgcggcc cgaagcctgt    840
agacctgctg ccggcggagc cgtgcacacc agaggcctgg acttcgcctg cgacatctac    900
atctgggccc ctctggccgg cacctgtggc gtgctgctgc tgagcctggt gatcaccctg    960
tactgcaacc accggaacaa acggggcaga aagaaactcc tgtatatatt caaacaacca   1020
tttatgagac cagtacaaac tactcaagag gaagatggct gtagctgccg atttccagaa   1080
gaagaagaag gaggatgtga actgagagtg aagttcagca gatccgccga cgcccctgcc   1140
taccagcagg gacagaacca gctgtacaac gagctgaacc tgggcagacg ggaagagtac   1200
gacgtgctgg acaagcggag aggccgggac cccgagatgg gcggaaagcc cagacggaag   1260 aaccccagg aaggcctgta taacgaactg cagaaagaca gatggccga ggcctacagc    1320 gagatcggca tgaagggcga gcggaggcgc ggcaagggcc acgatggcct gtaccagggc   1380
ctgagcaccg ccaccaagga cacctacgac gccctgcaca tgcaggccct gccccccaga   1440
```

CHIMERIC ANTIGEN RECEPTOR (CAR) BINDING TO BCMA, AND USES THEREOF

CROSS-REFERENCE TO RELATED APPLICATIONS

This application is a National Stage Application and claims priority under 35 U.S.C. § 371 to Patent Cooperation Treaty application PCT/CN2019/074212, filed Jan. 31, 2019, which claims the benefit of CN 201810100549.6, filed Feb. 1, 2018, and to CN 201811228154.0, filed Oct. 19, 2018. Priority is claimed to these applications and the disclosures of these prior applications are considered part of the disclosure of this application and to the extent allowed the entire contents of the aforementioned applications are incorporated herein.

SEQUENCE LISTING

This application incorporates by reference in its entirety the Sequence Listing entitled "262790-464401_SL_ST25.txt" is 52,507 bytes in size and was created on Mar. 24, 2020, and filed electronically herewith.

TECHNICAL FIELD

The present application relates to the field of biomedicine, and in particular to a chimeric antigen receptor capable of specifically binding to the BCMA protein.

BACKGROUND

The B-cell maturation antigen (BCMA), also known as CD269 or TNFRSF17, is a member of the tumor necrosis factor receptor family. Studies have shown that BCMA can bind with a B-cell activating factor receptor (BAFF) and a B-cell proliferation-inducing ligand (APRIL) to promote the survival of B cells at different stages of development. Abnormal signal transduction may result in the abnormal proliferation of B cells, leading to autoimmune diseases and tumorigenesis (see Rickert, et al., Immunological Reviews, 2011, Vol. 244: 115-133).

The chimeric antigen receptor (CAR) is an antigen receptor that is designed to identify a cell surface antigen in a human leucocyte antigen-independent manner. Some progress has been made in the attempts to treating such patients with CAR-expressing T cells (CAR-T) (Molecular Therapy, 2010, 18:4, 666-668; Blood, 2008, 112: 2261-2271).

Given the effectiveness of the BCMA being used as a therapeutic target in B-cell malignancies, and particularly in multiple myelomas, there is an urgent need in the art to develop a new cellular therapy to achieve the treatment goal by acting on the BCMA.

SUMMARY

The present application provides a chimeric antigen receptor capable of specifically binding to the BCMA and an application thereof. The BCMA chimeric antigen receptor provided by the present application has one or more of the following properties: 1) a higher affinity to the BCMA protein; 2) the CAR being able to be stably expressed in CAR-T cells that are prepared with the CAR; 3) a higher CAR positive rate in the CAR-T cells that are prepared with the CAR; 4) the release of cytokines being promoted by the CAR; 5) being able to be used to treat diseases or conditions associated with the expression of BCMA.

In one aspect, the present application includes a chimeric antigen receptor (CAR), wherein the CAR contains a BCMA-binding domain, a transmembrane domain, a costimulatory domain and an intracellular signal transduction domain, the BCMA-binding domain comprises an antibody or a fragment thereof capable of specifically binding a BCMA, and the antibody contains a heavy chain complementary determining region 1 (HCDR1), a heavy chain complementary determining region 2 (HCDR2) and a heavy chain complementary determining region 3 (HCDR3), wherein the HCDR1 comprises an amino acid sequence of SEQ ID NO: 9, the HCDR2 comprises an amino acid sequence of SEQ ID NO: 10, and the HCDR3 comprises an amino acid sequence of SEQ ID NO: 11.

In some embodiments, the antibody contains a light chain complementary determining region 1 (LCDR1), a light chain complementary determining region 2 (LCDR2) and a light chain complementary determining region 3 (LCDR3), and wherein the LCDR1 comprises an amino acid sequence of SEQ ID NO: 17, the LCDR2 comprises an amino acid sequence of SEQ ID NO: 18, and the LCDR3 comprises an amino acid sequence of SEQ ID NO: 19. In some embodiments, the antibody contains a heavy chain variable region, and the heavy chain variable region comprises an amino acid sequence of SEQ ID NO: 7. In some embodiments, the antibody contains a light chain variable region, and the light chain variable region comprises an amino acid sequence of SEQ ID NO: 15. In some embodiments, the antibody is a single-chain antibody fragment. In some embodiments, the antibody comprises an amino acid sequence of SEQ ID NO: 43.

In some embodiments, the transmembrane domain of the CAR includes transmembrane domains derived from proteins selected from a group of consisting of $\alpha$, $\beta$, $\zeta$ or chain of the T cell receptor, CD28, CD3e, CD45, CD4, CD5, CD8a, CD9, CD16, CD22, CD33, CD37, CD64, CD80, CD86, CD134, CD137 and CD154. In some embodiments, the transmembrane domain comprises an amino acid sequence of SEQ ID NO: 27.

In some embodiments, the costimulatory domain of the CAR includes costimulatory domains derived from proteins selected from a group consisting of CD28, 4-1BB, OX-40 and ICOS. In some embodiments, the costimulatory domain contains an amino acid sequence of SEQ ID NO: 29 or SEQ ID NO: 31.

In some embodiments, the intracellular signal transduction domain of the CAR includes a signal transduction domain derived from CD3. In some embodiments, the intracellular signal transduction domain contains an amino acid sequence of SEQ ID NO: 33.

In some embodiments, the CAR also contains a hinge region that links the BCMA-binding domain to the transmembrane domain. In some embodiments, the hinge region contains an amino acid sequence of SEQ ID NO: 25.

In some embodiments, the CAR is also linked to a signal peptide. In some embodiments, the signal peptide contains an amino acid sequence of SEQ ID NO: 3.

In some embodiments, the CAR is also linked to a cleaving peptide. In some embodiments, the cleaving peptide contains an amino acid sequence derived from a T2A peptide. In some embodiments, the cleaving peptide contains an amino acid sequence of SEQ ID NO: 35.

In some embodiments, the CAR contains an amino acid sequence of SEQ ID NO: 49 or SEQ ID NO: 51.

In another aspect, the present application further comprises an isolated nucleic acid molecule encoding the CAR described in the present application.

In another aspect, the present application also includes an isolated nucleic acid molecule encoding the CAR, which contains a nucleotide sequence of SEQ ID NO: 50 or SEQ ID NO: 52.

In another aspect, the present application also includes a vector, which contains the nucleic acid molecule of the present application. In some embodiments, the vector is selected from a plasmid, a retroviral vector and a lentiviral vector.

In another aspect, the present application also comprises an immune effector cell, which contains the CAR of the present application, the nucleic acid molecule of the present application, or the vector of the present application. In some embodiments, the immune effector cell is selected from a T lymphocyte and a natural killer (NK) cell.

In another aspect, the present application also comprises a method of preparing an immune effector cell, which includes introducing the vector of the present application into the immune effector cell.

In another aspect, the present application further includes a composition, which contains the immune effector cell of the present application.

In another aspect, the present application further comprises a use of the CAR, the nucleic acid molecule, the vector or the immune effector cell in the preparation of drugs used to treat diseases or conditions associated with the expression of BCMA. In some embodiments, the diseases or conditions associated with the expression of BCMA are cancers or malignant tumors.

Other aspects and advantages of the present application will be readily apparent to those skilled in the art from the following detailed description. Only the exemplary embodiments of the present application are shown and described in the following detailed description. The content of the present application enables those skilled in the art to modify the disclosed specific embodiments without departing from the spirit and scope of the invention involved in the present application, as will be realized by those skilled in the art. Accordingly, the drawings of the present application and description in the specification are merely intended to be illustrative and not restrictive.

DETAILED DESCRIPTION

Figure 1:
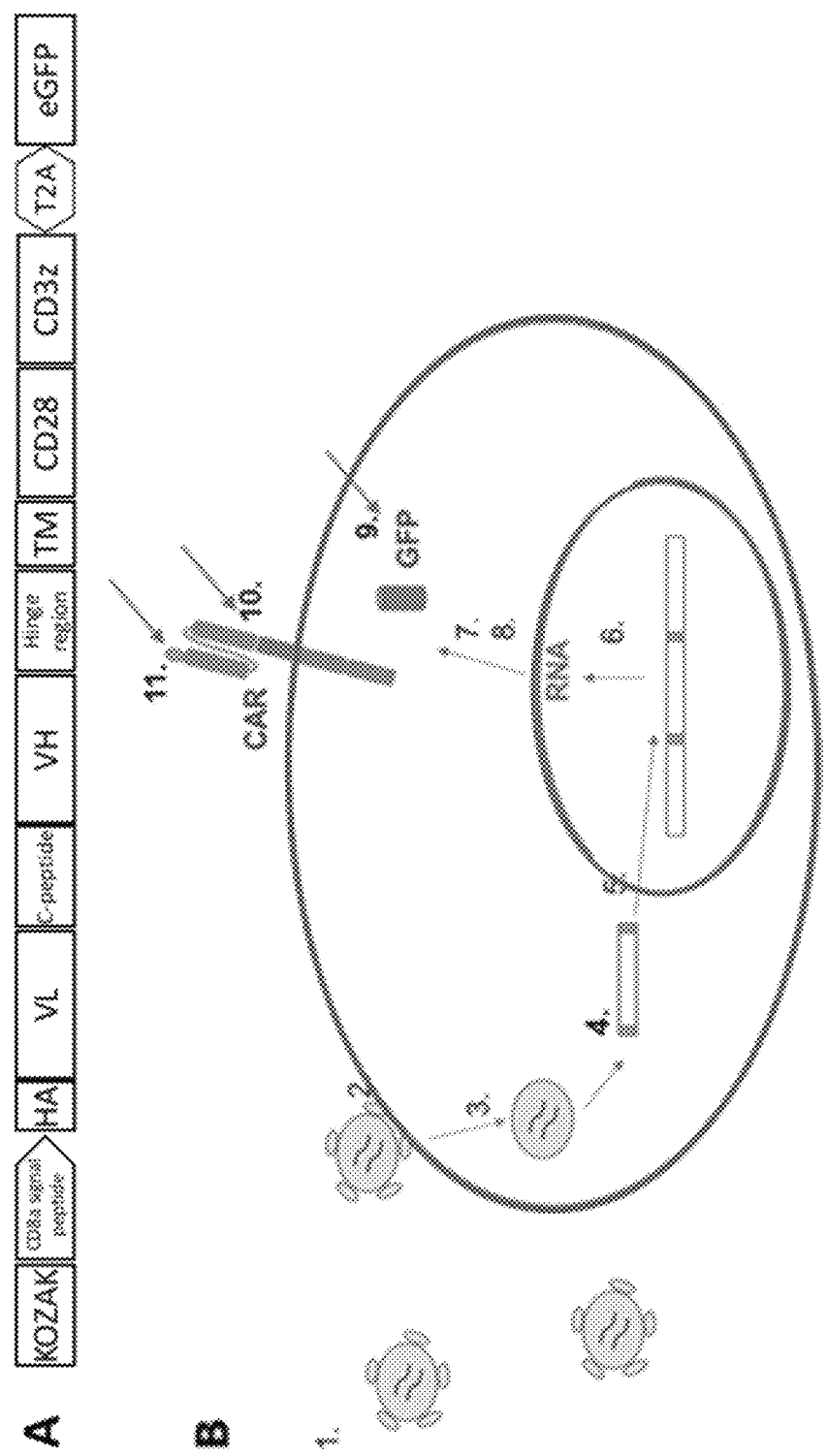
FIG. 1A shows the structure of the CAR of the present application.
FIG. 1B shows the expression level of the CAR of the present application through the evaluation of GFP signal.

The embodiments of the invention of the present application will be described hereinafter through specific examples. Those skilled in the art can easily appreciate other advantages and effects of the invention of the present application from the disclosure of the specification. The CAR of the present application can specifically bind to the BCMA, CAR-T cells that are prepared with the CAR can stably express the CAR, and the CAR-T cells that are prepared with the CAR have a higher CAR positive rate. In addition, the CAR can promote the release of cytokines, and is able to be used to treat diseases or conditions associated with the expression of BCMA.

The methods of conventional chemistry, biochemistry, organic chemistry, molecular biology, microbiology, recombinant DNA technique, genetics, immunology and cytobiology within the skill of the art are adopted to implement the present application unless otherwise explicitly indicated. The description of these methods can be found, for example, in Sambrook, et al., Molecular Cloning: A Laboratory Manual (3rd Edition, 2001); Sambrook, et al., Molecular Cloning: A Laboratory Manual (2nd Edition, 1989); Maniatis, et al., Molecular Cloning: A Laboratory Manual (1982); Ausubel, et al., Current Protocols in Molecular Biology (John Wiley and Sons, updated in July, 2008); Short Protocols in Molecular Biology: A Compendium of Methods from Current Protocols in Molecular Biology, Greene Pub. Associates and Wiley-Interscience; Glover, DNA Cloning: A Practical Approach, vol. I & II (IRL Press, Oxford, 1985); Anand, Techniques for the Analysis of Complex Genomes, (Academic Press, New York, 1992); Transcription and Translation (B. Hames & S. Higgins, Eds., 1984); Perbal, A Practical Guide to Molecular Cloning (1984); Harlow and Lane, Antibodies, (Cold Spring Harbor Laboratory Press, Cold Spring Harbor, N.Y., 1998) Current Protocols in Immunology Q. E. Coligan, A. M. Kruisbeek, D. H. Margulies, E.

M. Shevach and W. Strober, eds., 1991); Annual Review of Immunology; and periodicals and monographs such as Advances in Immunology.

Unless otherwise defined, the meanings of all the technological and scientific terms used in the present application are the same as those generally understood by those of ordinary skill in the art. For the purpose of the present application, the following terms are defined.

In the present application, the term "chimeric antigen receptor (CAR)" generally refers to a fusion protein that contains an extracellular domain capable of binding with an antigen and at least one intracellular domain. The CAR is a core part of a chimeric antigen receptor T cell (CAR-T), and may contain an antigen (such as a tumor-associated antigen (TAA)) binding domain, a transmembrane domain, a costimulatory domain and an intracellular signal domain. In the present application, the CAR may be combined with a T cell receptor-activating intracellular domain specifically based on the antigen (such as the BCMA) of an antibody. The genetically-modified CAR-expressing T cells can specifically identify and eliminate target antigen-expressing malignant cells. The description of the CAR and the CAR-T cells can be found, for example, in Sadelain M, Brentjens R, Rivi'ere I. The basic principles of chimeric antigen receptor design. Cancer Discov. 2013; 3(4): 388-398; Turtle C J, Hudecek M, Jensen M C, Riddell S R. Engineered T cells for anti-cancer therapy. Curr Opin Immunol. 2012; 24(5): 633-639; Dotti G, Gottschalk S, Savoldo B, Brenner M K. Design and development of therapies using chimeric antigen receptor-expressing T cells. Immunol Rev. 2014; 257(1): 107-126; WO2013154760 and WO2016014789.

In the present application, the terms "BCMA" and "B-cell maturation antigen" may be used interchangeably, and generally refer to a protein encoded by TNFRSF17 gene. The BCMA protein is a member of the tumor necrosis factor receptor family. In the present application, the BCMA may be a human BCMA, with a GenBank accession number of BAB60895.1. The BCMA is a type-III transmembrane protein, and possesses a cysteine-rich domain (CRD) characterizing members of the TNFR family in extracellular domain (ECD), which forms a ligand-binding motif. As a B-cell biomarker, the BCMA is expressed in a tumor cell (such as a multiple myeloma cell) or located on the surface of a tumor cell (for example, a malignant plasmocyte of multiple myeloma). The BCMA protein may also comprise a fragment of the BCMA, such as an extracellular domain and a fragment thereof, such as a binding domain, a transmembrane domain, a costimulatory domain, and an intracellular signal transduction domain and a fragment able to bind with any antibody of the present application.

In the present application, the term "BCMA-binding domain" generally refers to a domain that can specifically bind to the BCMA protein. For example, the BCMA-binding domain may comprise a chimeric antigen receptor or a fragment thereof capable of specifically binding to a human BCMA polypeptide expressed on a B cell or, as well as an anti-BCMA antibody or an antigen-binding fragment thereof. Terms "binding domain", "extracellular domain", "extracellular binding domain", "antigen-specific binding domain" and "extracellular antigen-specific binding domain" used in the present application can be used interchangeably, and provide a CAR domains or fragments having the ability to specifically bind to a target antigen (such as BCMA). The BCMA-binding domain may be derived from a natural source, a synthetic source, a semi-synthetic source or a recombinant source.

In the present application, the term "antibody" generally refers to a polypeptide molecule capable of specifically identifying and/or neutralizing a specific antigen. For example, the antibody may comprise an immunoglobulin consisting of at least two heavy (H) chains and two light (L) chains that are connected to each other via disulfide bonds, and comprise any molecule containing an antigen-binding part thereof. The term "antibody" comprises monoclonal antibodies, antibody fragments or antibody derivatives, including but not limited to human antibodies, humanized antibodies, chimeric antibodies, single-domain antibodies (such as dAb), single-chain antibodies (such as scFv) and antigen-binding antibody fragments (such as Fab, Fab' and (Fab)2 fragments). The term "antibody" further comprises all recombinant forms of the antibody, such as an antibody expressed in prokaryotic cells, an unglycosylated antibody, as well as any antigen-binding antibody fragment and derivatives thereof. Each heavy chain can be composed of a heavy chain variable region (VH) and a heavy chain constant region. Each light chain can be composed of a light chain variable region (VL) and a light chain constant region. The VH and VL can be further divided into hypervariable regions known as complementary determining regions (CDR), which are scattered in more-conserved regions known as framework regions (FR). Each of the VH and VL can be composed of three CDRs and four FRs, which may be arranged from the amino terminal to the carboxyl terminal according to the following order: FR1, CDR1, FR2, CDR2, FR3, CDR3 and FR4. The variable regions of heavy chains and light chains comprise a binding domain interacting with antigens. The constant regions of the antibody may mediate the binding of the immunoglobulin to a host tissue or factor that comprises a variety of cells (such as effector cells) of the immune system and a first component (Clq) of the classical complement system.

In the present application, the term "antigen-binding molecule" generally refers to a molecule containing an antigen-binding region or antigen-binding part capable of binding a target antigen. For example, the antigen-binding molecule may be a protein or a polypeptide. In the present application, when the target antigen is a B-cell maturation antigen (BCMA), the antigen-binding molecule binding BCMA is also called as a BCMA-binding molecule. The antigen-binding molecules include, for example, antibodies and antigen-binding fragments thereof, single-chain scFv antibodies, as well as various fusions and conjugates constructed based on scFv (such as scFv-Fc antibodies, immunoconjugates, antibody-drug conjugates (ADCs), multispecific/bispecific antibodies, and chimeric antigen receptors (CARs)). As known by those skilled in the art, the antigen-binding part of the antibody generally comprises an amino acid residue derived from the "complementary determining regions" or "CDRs". In some cases, "BCMA-binding molecule" and "antibody of the present application" or "anti-BCMA antibody" may be used interchangeably according to the context.

In the present application, the term "single-chain antibody fragment" may be an antibody that is formed by the heavy chain variable regions and the light chain variable regions connected via a connecting peptide.

In the present application, the term "transmembrane domain" generally refers to a domain in the CAR that passes through the cell membrane and is linked to the intracellular signal transduction domain, playing a role of signaling.

In the present application, the term "costimulatory domain" generally refers to an intracellular domain capable of providing an immunocostimulatory molecule, and the immunocostimulatory molecule is a cell surface molecule required in the effective response of lymphocytes to an antigen. The costimulatory domain mentioned may include a costimulatory domain of CD28, and may also include costimulatory domains of the TNF receptor family, such as costimulatory domains of OX40 and 4-1BB.

In the present application, the term "hinge region" generally refers to a connecting region between an antigen-binding region and an immunocyte Fc receptor (FcR)-binding region.

In the present application, the term "HA-tag" generally refers to a protein tag based on a human influenza hemagglutinin antigen, and its chemical nature is a short amino acid sequence derived from human influenza hemagglutinin amino acids 98-106. After a method of molecular biology is adopted to splice the HA-tag sequence to one terminal of a target protein, an anti-HA-tag specific antibody can be used to bind with the recombinant protein, which is favorable for the conduct of experiments such as immunohistochemistry (IHC), Western Blotting, etc. (see Schembri, Laura, et al., The HA tag is cleaved and loses immunoreactivity during apoptosis. Nature Methods. February 2007, 4 (2): 107-108).

In the present application, the term "intracellular signal transduction domain" generally refers to a domain that is located inside a cell and can transduce signals. In the present application, the intracellular signal transduction domain can transduce signals into the cell. For example, the intracellular signal transduction domain is an intracellular signal transduction domain of the chimeric antigen receptor. For example, in some embodiments, the intracellular signal transduction domain may be selected from a group consist of a CD3 intracellular domain, a CD28 intracellular domain, a CD28 intracellular domain, a 4-1BB intracellular domain and an OX40 intracellular domain.

In the present application, the term "signal peptide" generally refers to a peptide chain for guiding the protein transfer. In some embodiments, the signal peptide may be a short peptide chain, which have a length of 5 to 30 amino acids.

In the present application, the term "cleaving peptide" refers to a type of polypeptides that is able to implement a protein cleaving function. For example, the cleaving peptide can achieve the protein cleaving by ribosome skipping rather than protease hydrolysis. For example, the cleaving peptide mentioned may be cleaving 2A peptides that may include T2A, F2A, P2A, etc.

In the present application, the term "marker detection signal" generally refers to a gene, a protein or other molecules with known functions and sequences that can play the role of a specific marker and emit detectable signals. The marker detection signal may be fluorescent proteins, such as GFP, RFP, YFP, etc. The marker detection signal mentioned may be EGFRt.

In the present application, the term "EGFRt" generally refers to a gene encoding a truncated human epidermal growth factor receptor polypeptide. The EGFRt lacks a membrane-distal EGF-binding domain and a cytoplasmic signal transduction tail, but keeps an extracellular epitope identified by an anti-EGFR antibody. The EGFRt can be used as a non-immunogenic selection tool with a function of genetically modifying cells and a tracking marker. In the present application, the EGFRt may serve as a marker molecule for a CAR-T cell. The EGFRt mentioned may eliminate the cetuximab-mediated ADCC pathway for the CAR-T cells in the body if necessary (see U.S. Pat. No. 8,802,374B2).

In the present application, the term "Kozak sequence" generally refers to a (gcc)gccRccAUGG sequence that is common in the mRNAs of eukaryotes. The Kozak sequence plays an important role in initiating the translation process, and is identified as a translation initiation site by ribosomes (see, DeAngioletti M, et al., a novel silent beta-thalassaemia mutation, the first in the Kozak sequence. Br J Haematol. 2004, 124 (2): 224-31.).

In the present application, the term "isolated" generally means that an antibody which has been separated from its components in the natural environment. In some embodiments, the antibody is purified to have a purity of higher than 95% or 99%, which is determined by, for example, electrophoresis (such as SDS-PAGE, isoelectric focusing (IEF) or capillary electrophoresis) or chromatography (such as ion exchange or reversed-phase HPLC). The overview of the method for evaluating the antibody purity can be found in Flatman, S. et al, J. Chrom. B 848 (2007) 79-87.

In the present application, the term "nucleic acid molecule" generally refers to an isolated nucleotide, deoxyribonucleotide or ribonucleotide or an analogue thereof of any length. In some embodiments, the nucleic acid molecule of the present application may be isolated from the natural environment. In some embodiments, the nucleic acid molecule of the present application may be produced or synthesized by the following methods: (i) in-vitro amplification, such as polymerase chain reaction (PCR) amplification; (ii) cloning and recombination; (iii) purification, such as digestion and gel electrophoresis fractionation; (4) synthesis, such as chemical synthesis. In some embodiments, the isolated nucleic acid is a nucleic molecule prepared by the recombinant DNA technology. In the present application, the nucleic acid encoding the antibody or the antigen-binding fragment thereof can be prepared by a variety of methods known in the art, including but not limited to adopting restriction fragment operation or overlap extension PCR of synthesized oligonucleotide. The specific operation can be found in Sambrook, et al., Molecular Cloning, A Laboratory Manual, Cold Spring Harbor Laboratory Press, Cold Spring Harbor, N.Y., 1989; and Ausube, et al., Current Protocols in Molecular Biology, Greene Publishing and Wiley-Interscience, New York N.Y., 1993.

In the present application, the "vector" generally refers to a nucleic acid molecule capable of self-replicating in a suitable host, and it is used to transfer the inserted nucleic acid molecules into host cells and/or the intercellular substance between host cells. The vector may comprise a vector mainly used for inserting DNA or RNA into cells, a vector mainly used for replicating DNA or RNA, and a vector mainly used for the expression of transcription and/or translation of DNA or RNA. The vector further includes a vector with a variety of the aforementioned functions. The vector may be a polynucleotide which can be transcribed and translated into a polypeptide when it is introduced into a suitable host cell. Generally, the vector can produce a desirable expression product by culturing the suitable host cell containing the vector. In the present application, the vector may contain one or more types of the nucleic acid molecules. In addition, the vector may further contain other genes, for example, a marker gene allowing the vector to be selected in a suitable host cell and an appropriate condition. In addition, the vector may also contain an expression control element that allows the coding region to be correctly expressed in a suitable host. Such a control element is well-known to those skilled in the art, and, for example, can include a promoter, a ribosome-binding site, an enhancer, and other control elements for regulating gene transcription or mRNA translation. In some embodiments, the expression control sequence is a regulable element. The specific structure of the expression control sequence can be varied according to the functions of species or cell types, but generally contains a 5' non-transcribed sequence and 5' and 3' non-translated sequences which participate in the transcription initiation and the translation initiation respectively, such as a TATA box, a capped sequence, a CAAT sequence, etc. For example, 5' non-transcribed expression control sequence can contain a promoter region, which can comprise a promoter sequence for transcribing and controlling functionally-linked nucleic acids. The vector of the present application can be selected from a plasmid, a retroviral vector and a lentiviral vector. The plasmid, retroviral vector and lentiviral vector of the present application can contain the CAR.

In the present application, the term "plasmid" generally refers to a DNA molecule other than chromosomes or nucleoids in organisms such as bacteria, saccharomycetes, etc. Plasmids, which can exist in cytoplasm, have the capability of self-replicating, so that a constant copy number therefor can be kept in offspring cells and the carried genetic information can be expressed. Plasmids can be used as vectors for genes in genetic engineering researches.

In the present application, the term "retroviral vector" generally refers to a virion that can clone and express exogenous genes but cannot be self-packaged to have the proliferation capability. Most of such viruses have reverse transcriptase. A retrovirus comprises at least three types of genes: gag, comprising a gene for proteins forming the viral core and structure; pol, comprising a gene for reverse transcriptase and env, comprising a gene forming virus coat. The genome of the retroviral vector itself and an exogenous gene carried by it can be randomly and stably integrated into the genome of a host cell through the retrovirus transfection, for example, the CAR molecule may be integrated into the host cell.

In the present application, the term "lentiviral vector" generally refers to a diploid RNA viral vector that belongs to the retrovirus. The lentiviral vector is a vector that is prepared by removing multiple sequence structures associated with virus activity in the genome of a lentivirus to provide the genome with biological safety and then introducing the sequence and expression structure of a target gent needed by an experiment into this genome framework. The genome of the retroviral vector itself and an exogenous gene carried by it can be randomly and stably integrated into the genome of a host cell through the lentiviral vector transfection, for example, the CAR molecule can be integrated into the host cell.

In the present application, the term "transposon" generally refers to a discrete DNA fragment containing a transposase gene. The flanking sequences are terminal inverted repeats (TIRs) containing transposase-binding sites. The transposase can bind with a TIR and transfer the transposon to a new site. The transposon of the present application is a double-component system composed of a CAR-carrying plasmid (transposon) and a transposase-carrying plasmid. The transposon may be introduced into a target cell by electric transduction or other methods. For example, the two components are first electroporated into a peripheral blood mononuclear cell (PBMC), and the expressed transposase acts on the terminal inverted repeats (TIRs) on both sides of the CAR, so that the CAR (transposon) is cut and then integrated onto the TA dinucleotide sequence in the genome of the target cell (such as a T cell). After the transposition and the stable genome integration are complete, a CAR protein can be expressed on the surface of the target cell (see Cheng Zhang, Jun Liu, Jiang F Zhong, et al. Engineering CAR-T cells. Biomarker Research. 2017, 5: 22).

In the present application, the term "gene editing" generally refers to a technique for site-directed modification of a targeted genome. The gene editing may include techniques based on zinc finger nucleases (ZFNs), transcription activator like effector nucleases (TALENs), clustered regularly interspaced short palindromic repeats/CRISPR-associated (Cas9), CRISPR/Cas9), etc. The gene editing can achieve the highly efficient targeted modification on a genome by adding, removing or changing the genetic material at a specific position of a genome. The gene editing of the present application can comprise introducing the CAR molecule into the genome of a recipient cell by a gene editing technique (such as CRISPR-Cas9).

In the present application, the term "immune effector cell" generally refers to an immunocyte that participates in removing foreign antigens and performing an effector function in the immune response. For example, in some embodiments, the immune effector cell may be a plasmocyte, a cytotoxic T cell, a NK cell, an APSC pluripotent cell, a mast cell, etc.

In the present application, the term "pharmaceutically acceptable adjuvant" generally refers to a pharmaceutically acceptable preparation vector, solution or additive for enhancing preparation properties. Such additives are well-known to those skilled in the art.

In the present application, the term "cancer" generally refers to a disease caused by the abnormality of the mechanism for controlling cell proliferation. In the present application, hyperproliferative diseases known as cancers include but are not limited to solid tumors, such as cancers occurring in breasts, respiratory tracts, brains, reproductive organs, alimentary canals, urethrae, eyes, livers, skins, heads and necks, thyroid glands and parathyroid glands, as well as distant metastases thereof. Such diseases also include lymphomas, sarcomas and leukemias. The examples of breast cancers include but are not limited to invasive ductal carcinoma, invasive lobular carcinoma, ductal carcinoma in situ and lobular carcinoma in situ. The examples of respiratory tract cancers include but are not limited to small cell lung cancer, non-small cell lung cancer, bronchial adenoma and pleuropulmonary blastoma. The examples of brain cancers include but are not limited to brain stem and hypothalamic gliomas, cerebellar and cerebral astrocytomas, medulloblastoma, ependymoma and neuroectodermal and pineal tumors. Male genital neoplasms include but are not limited to prostatic cancers and testicular cancers. Female genital neoplasms include but are not limited to endometrial cancer, cervical cancer, ovarian cancer, vaginal cancer, vulvar cancer and hysteroma. Gastrointestinal tumors include but are not limited to anal cancer, colon cancer, colorectal cancer, esophageal cancer, gallbladder cancer, stomach cancer, pancreatic cancer, rectal cancer, small intestine cancer and salivary gland cancer. Urethral tumors include but are not limited to bladder cancer, penile cancer, renal carcinoma, renal pelvic carcinoma, ureteral cancer and urethral cancer. Eye cancers include but are not limited to intraocular melanoma and retinoblastoma. The examples of liver cancers include but are not limited to hepatocellular carcinoma (hepatocellular carcinoma with or without fibrolamellar variation), cholangiocarcinoma (intrahepatic cholangiocarcinoma) and combined hepatocellular-cholangiocarcinoma. Skin cancers include but are not limited to squamous-cell carcinoma, Kaposi's sarcoma, malignant melanoma, Merkel cell carcinoma and non-melanoma skin cancers. Head and neck cancers include but are not limited to laryngeal/hypopharyngeal/nasopharyngeal/oropharyngeal carcinomas, as well as lip and oral cancers. Lymphomas include but are not limited to AIDS-associated lymphoma, non-Hodgkin's lymphoma, cutaneous T-cell lymphoma, Hodgkin's disease and central nervous system lymphoma. Sarcomas include but are not limited to soft tissue sarcoma, osteosarcoma, malignant fibrous histiocytoma, lymphosarcoma and rhabdomyosarcoma. Leukemias include but are not limited to acute myeloid leukemia, acute lymphocytic leukemia, chronic lymphocytic leukemia, chronic myelocytic leukemia and hairy cell leukemia.

The term "and/or" should be understood as any one of the options or both of the options.

As used in the present application, the term "comprise" or "include" is intended to encompass the described elements, integers or steps, but does not exclude any other elements, integers or steps. In the present application, when the term "comprise" or "include" is used, it encompasses a case composed of the elements, integers or steps unless otherwise specified. For example, when it relates to "comprising" the antibody variable region of a certain specific sequence, it is also intended to cover an antibody variable region composed of the specific sequence.

In the present application, the term "about" generally refers to a variation within a range of 0.5%-10% above or below a specified value, for example, a variation within a range of 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10% above or below a specified value.

Chimeric Antigen Receptor

In the present application, the CAR may comprise an extracellular domain capable of specifically binding a BCMA, a transmembrane domain, an intracellular costimulatory signal transduction domain, and an intracellular signal transduction domain. In the present application, the extracellular domain of the CAR may comprise the single-chain antibody fragment (scFv) of the present application. For example, the single-chain antibody fragment may be linked to the transmembrane domain through a hinge region (such as a CD8 hinge). In the present application, the CAR may be used to transduce an immune effector cell (such as a T cell), and be expressed on the cell surface. Thus, the present application can also provide a T cell expressing the chimeric antigen receptor, as well as a use of the T cell and/or the CAR in the preparation of drugs for treating B cell-associated diseases.

In the present application, the chimeric antigen receptor (CAR) may comprise a BCMA-binding domain, a transmembrane domain, a costimulatory domain and an intracellular signal transduction domain.

In the present application, the BCMA-binding domain may comprise an antibody fragment capable of specifically binding a BCMA, and the antibody may comprise a heavy chain complementary determining region 1 (HCDR1), a heavy chain complementary determining region 2 (HCDR2) and a heavy chain complementary determining region 3 (HCDR3), wherein the HCDRs 1-3 may comprise amino acid sequences of SEQ ID NOs: 9-11 in sequence; the antibody may also comprise a light chain complementary determining region 1 (LCDR1), a light chain complementary determining region 2 (LCDR2) and a light chain complementary determining region 3 (LCDR3), and the LCDRs 1-3 may comprise amino acid sequences of SEQ ID NOs: 17-19 in sequence. In the present application, the antibody may comprise a heavy chain variable region that may comprise an amino acid sequence of SEQ ID NO: 7. In the present application, the antibody may comprise a light chain variable region that may comprise an amino acid sequence of SEQ ID NO: 15.

In the present application, the antibody may be a single-chain antibody fragment. In some embodiments, the antibody may comprise an amino acid sequence of SEQ ID NO: 43. For example, the single-chain antibody fragment may include scFv0026 with a sequence of SEQ ID NO: 43.

For example, the single-chain antibody fragment of the present application may be scFv0026 with a sequence of SEQ ID NO: 43. The LCDRs 1-3 of the single-chain antibody fragment (scFv0026) comprise an amino acid sequence of SEQ ID NO: 17, SEQ ID NO: 18 and SEQ ID NO: 19 respectively; the VL comprises an amino acid sequence of SEQ ID NO: 15; the HCDRs 1-3 comprise an amino acid sequence of SEQ ID NO: 9, SEQ ID NO: 10 and SEQ ID NO: 11 respectively; and the VH comprise an amino acid sequence of SEQ ID NO: 7.

The CAR of the present application may comprise a transmembrane domain, and the transmembrane domain may comprise a transmembrane domain derived from proteins selected from a group consisting of α, β or ζ chain of the T cell receptor, CD28, CD3e, CD45, CD4, CD5, CD8a, CD9, CD16, CD22, CD33, CD37, CD64, CD80, CD86, CD134, CD137 and CD154. In the present application, the transmembrane domain may comprise an amino acid sequence of SEQ ID NO: 27. For example, the transmembrane domain of the present application may comprise a transmembrane domain of CD8a, with a sequence of SEQ ID NO: 27.

In the present application, the costimulatory domain may comprise a costimulatory domain derived from proteins selected from a group consisting of CD28, 4-1BB, OX40 and ICOS. In the present application, the costimulatory domain may comprise an amino acid sequence of SEQ ID NO: 29 or SEQ ID NO: 31.

The CAR of the present application can contain an intracellular signal transduction domain, and the intracellular signal transduction domain can include a signal transduction domain derived from CD3. In the present application, the intracellular signal transduction domain may comprise an amino acid sequence of SEQ ID NO: 33.

The CAR of the present application may contain a hinge region that links the antibody and the transmembrane domain. In the present application, the hinge region may comprise an amino acid sequence of SEQ ID NO: 25.

The CAR of the present application may also comprise an HA-tag that may be located at the N terminal of the CAR. In the present application, the HA-tag may comprise an amino acid sequence of SEQ ID NO: 5. In the present application, an anti-HA antibody may be used to specifically bind with the CAR so as to assay the expression of the CAR of the present application and enrich the CAR-T cell for functionality study.

The CAR of the present application may be linked to a signal peptide that may comprise an amino acid sequence of SEQ ID NO: 3. For example, the signal peptide may be a CD8a signal peptide with a sequence of SEQ ID NO: 3. For example, CAR0037, CAR0085 and CAR0087 may be linked to the CD8a signal peptide.

In the present application, the CAR may also be linked to a cleaving peptide. In the present application, the cleaving peptide may comprise an amino acid sequence derived from a T2A peptide. In the present application, the cleaving peptide may comprise an amino acid sequence may comprise SEQ ID NO: 35. For example, the cleaving peptide may be a T2A with a sequence of SEQ ID NO: 35. For example, CAR0037 and CAR0087 may be linked to the cleaving peptide T2A.

In the present application, the CAR may also be linked to a marker detection signal that may be located at the C terminal of the CAR. In the present application, the marker detection signal may be a fluorescent protein, which may be selected from a group consisting of GFP, RFP and YFP. In the present application, the expression of CAR molecules may be indirectly evaluated by detecting the GFP signal. For example, the CAR may comprise CAR0037 with a marker detection signal sequence of SEQ ID NO: 37. In the present application, the marker detection signal may be EGFRt. For example, CAR0087 may be linked to a marker detection signal with a sequence of SEQ ID NO: 39.

In the present application, the CAR may be linked to a Kozak sequence with a sequence of SEQ ID NO: 1. In the present application, the CAR may be linked to a Kozak sequence that may be located at the N terminal of the CAR. For example, CAR0037, CAR0085 or CAR0087 may be linked to a Kozak sequence with a sequence of SEQ ID NO: 1.

In the present application, the CAR may comprise an amino acid sequence of SEQ ID NO: 49 or SEQ ID NO: 51. For example, the CAR may be selected from CAR0037 with a sequence of SEQ ID NO: 49. As another example, the CAR may be selected from CAR0085 with a sequence of SEQ ID NO: 51; and the CAR may be selected from CAR0087 with a sequence of SEQ ID NO: 51.

In certain embodiments, the CAR of the present application may, from its N terminal, comprise a BCMA-binding domain, a transmembrane domain, a costimulatory domain and an intracellular signal transduction domain in sequence. The CAR may comprise a BCMA-binding domain, and the BCMA-binding domain comprise a sequence of SEQ ID NO: 43. The BCMA-binding domain may comprise HCDRs 1-3 with sequences of SEQ ID NOs: 9-11 in sequence, and the BCMA-binding domain may comprise LCDRs 1-3 with sequences of SEQ ID NO: 17-19 in sequence. For example, the CAR may comprise CAR0037 or the CAR of the present application having the same LCDR 1-3 and HCDR 1-3 as CAR0037. The BCMA-binding domain may comprise a heavy chain variable region with a sequence of SEQ ID NO: 7; and the BCMA-binding domain may also comprise a light chain variable region with a sequence of SEQ ID NO: 15. For example, the CAR may comprise CAR0037 or the CAR of the present application having the same light chain variable region and heavy chain variable region as CAR0037. A connecting peptide may also be comprised between the light chain variable region and the heavy chain variable region, which has a sequence pf SEQ ID NO: 23. For example, the CAR may comprise CAR0037 or the CAR of the present application having the same connecting peptide as CAR0037. The transmembrane domain may comprise a transmembrane domain derived from CD8a, with a sequence of SEQ ID NO: 27. For example, the CAR may comprise CAR0037 or a CAR of the present application having the same transmembrane domain as CAR0037. The costimulatory domain can comprise a costimulatory domain derived from CD28, with a sequence of SEQ ID NO: 29. For example, the CAR may comprise CAR0037 or the CAR of the present application having the same costimulatory domain as CAR0037. The intracellular signal transduction domain may comprise a signal transduction domain derived from CD3, with a sequence of SEQ ID NO: 33. For example, the CAR may comprise CAR0037 or a CAR of the present application having the same intracellular signal transduction domain as CAR0037.

The CAR may also comprise a hinge region that may be located at the C terminal of the BCMA-binding domain and the N terminal of the transmembrane domain, and the hinge region has a sequence of SEQ ID NO: 25. For example, the CAR may comprise CAR0037 or a CAR of the present application having the same hinge region as CAR0037.

The CAR may also be linked to an HA-tag that may be located at the N terminal of the BCMA-binding domain, and the HA-tag has a sequence of SEQ ID NO: 5. For example, the CAR may comprise CAR0037 or a CAR of the present application having the same HA-tag as CAR0037.

The CAR may also be linked to a signal peptide that may be located at the N terminal of the CAR, and the signal peptide has a sequence of SEQ ID NO: 3.

The CAR may also be linked to a cleaving peptide such as T2A. The cleaving peptide may be located at the C terminal of the intracellular signal transduction domain, and the cleaving peptide has a sequence of SEQ ID NO: 35. The CAR may also be linked to a marker detection signal that may be located at the C terminal of the CAR (or the cleaving peptide). The marker detection signal may be selected from a group consisting of GFP, RFP and YFP, and the marker detection signal comprises a sequence of SEQ ID NO: 37.

For example, the CAR of the present application may be CAR0037, and the LCDRs 1-3 comprise an amino acid sequence of SEQ ID NO: 17, SEQ ID NO: 18 and SEQ ID NO: 19 respectively; the VL comprises an amino acid sequence of SEQ ID NO: 15; the HCDRs 1-3 comprise an amino acid sequence of SEQ ID NO: 9, SEQ ID NO: 10 and SEQ ID NO: 11 respectively; the VH comprises an amino acid sequence of SEQ ID NO: 7; the connecting peptide between the VH and the VL comprises a sequence of SEQ ID NO: 23; its hinge region comprises a sequence of SEQ ID NO: 25; its transmembrane domain comprises an amino acid sequence of SEQ ID NO: 27; its costimulatory domain is a CD28 costimulatory domain, with a sequence of SEQ ID NO: 29; its CD3 intracellular signal transduction domain comprises an amino acid sequence of SEQ ID NO: 33; the CAR0043 may also comprise a cleaving peptide of SEQ ID NO: 35 and a GFP marker detection signal of SEQ ID NO: 37; and the CAR0037 may also comprise a KOZAK sequence of SEQ ID NO: 1, a CD8a signal peptide of SEQ ID NO: 3, and an HA-tag of SEQ ID NO: 5.

For example, the CAR of the present application may be CAR0085, and the LCDRs 1-3 comprise an amino acid sequence of SEQ ID NO: 17, SEQ ID NO: 18 and SEQ ID NO: 19 respectively; the VL comprises an amino acid sequence of SEQ ID NO: 15; the HCDRs 1-3 comprise an amino acid sequence of SEQ ID NO: 9, SEQ ID NO: 10 and SEQ ID NO: 11 respectively; the VH comprises an amino acid sequence of SEQ ID NO: 7; the connecting peptide between the VH and the VL comprises a sequence of SEQ ID NO: 23; its hinge region comprises a sequence of SEQ ID NO: 25; its transmembrane domain comprises a sequence of SEQ ID NO: 27; its costimulatory domain is a 4-1BB costimulatory domain of SEQ ID NO: 31; its CD3 intracellular signal transduction domain comprises a sequence of SEQ ID NO: 33; the CAR0085 may also comprise a KOZAK sequence of SEQ ID NO: 1 and a CD8a signal peptide of SEQ ID NO: 3.

For example, the CAR of the present application may be CAR0087, and the LCDRs 1-3 comprise an amino acid sequence of SEQ ID NO: 17, SEQ ID NO: 18 and SEQ ID NO: 19 respectively; the VL comprises an amino acid sequence of SEQ ID NO: 15; the HCDRs 1-3 comprises an amino acid sequence of SEQ ID NO: 9, SEQ ID NO: 10 and SEQ ID NO: 11 respectively; the VH comprises an amino acid sequence of SEQ ID NO: 7; the connecting peptide between the VH and the VL comprises a sequence of SEQ ID NO: 23; its hinge region comprises a sequence of SEQ ID NO: 25; its transmembrane domain comprises a sequence of SEQ ID NO: 27; its costimulatory domain is a 4-1BB costimulatory domain of SEQ ID NO: 31; its CD3 intracellular signal transduction domain comprises a sequence of SEQ ID NO: 33; the CAR0085 may also comprise a cleaving peptide of SEQ ID NO: 35 and an EGFRt marker detection signal of SEQ ID NO: 39; and the CAR0087 may also comprise a KOZAK sequence of SEQ ID NO: 1 and a CD8a signal peptide of SEQ ID NO: 3.

The proteins, the polypeptides and/or the amino acid sequences involved in the present application should also be understood to at least include functional variants or homologues having the same or similar functions as the proteins or the polypeptides.

In the present application, the functional variants may be proteins or polypeptides which are obtained by substituting, deleting or adding one or more amino acids in the amino acid sequences of the above proteins and/or polypeptides (such as antibodies able to specifically bind with the BCMA or fragments thereof). For example, the functional variants can include proteins or polypeptides that have different amino acid sequences due to substitution, deletion and/or insertion of at least one amino acid, such as 1 to 30, 1 to 20 or 1 to 10, or such as 1, 2, 3, 4 or 5. The functional variants can substantially remain the biological characteristics of the proteins or the polypeptides that are unmodified (substitution, deletion or addition). For example, the functional variants can remain at least 60%, 70%, 80%, 90% or 100% of the biological activity (such as antigen binding ability) of the original proteins or polypeptides. For example, the substitution may be a conservative one.

In the present application, the homologues may be proteins or polypeptides that have at least about 85% (such as at least about 85%, 90%, 91%, 92%, 93%, 94%, 95%, 96%, 97%, 98%, 99% or higher) of amino acid sequence homology with the above proteins and/or polypeptides (such as antibodies able to specifically bind with the BCMA or fragments thereof).

In the present application, the homology generally refers to the likeness, similarity or correlation between two or more sequences. The "sequence homology percentage" can be calculated by the following method: two to-be-compared sequences being compared in a comparison window to determine the number of positions having the same nucleic acid base (such as A, T, C, G and I) or the same amino acid residues (such as Ala, Pro, Ser, Thr, Gly, Val, Leu, Ile, Phe, Tyr, Trp, Lys, Arg, His, Asp, Glu, Asn, Gln, Cys and Met) in the two sequences so that the number of matching positions is obtained; then the number of the matching positions being divided by the total number of positions in the comparison window (i.e. the window size); and the result being multiplied by 100 to obtain the sequence homology percentage. The comparison for determining the sequence homology percentage can be conducted by a variety of methods known in the art, for example, using publically available computer software such as BLAST, BLAST-2, ALIGN or Megalign (DNASTAR) software. Those skilled in the art can determine appropriate parameters for sequence comparison, including any algorithm needed for implementing maximum comparison within compared full-length sequence ranges or target sequence regions. The homology may also be determined by the following methods: FASTA and BLAST. The description of the FASTA algorithm can be found in "Improved Tools for Biological Sequence Comparison" by W. R. Pearson and D. J. Lipman, Proceedings of the National Academy of Sciences of the United States of America (Proc. Natl. Acad. Sci.), 85: 2444-2448, 1988; and "Rapid and Sensitive Protein Similarity Searches" by D. J. Lipman and W. R. Pearson, Science, 227: 1435-1441, 1989. The description of the BLAST algorithm could be found "A Basic Local Alignment Search Tool" by S. Altschul, W. Gish, W. Miller, E. W. Myers and D. Lipman, Journal of Molecular Biology, 215: 403-410, 1990.

Nucleic Acid, Vector, Cell, Preparation Method and Composition

In another aspect, the present application provides an isolated nucleic acid molecule, which may encode the CAR of the present application. The isolated nucleic acid molecule encoding the CAR of the present application may comprise a nucleotide sequence of SEQ ID NO: 50 or SEQ ID NO: 52 or functional variants thereof. The nucleic acid molecule of the present application may be isolated. For example, the nucleic acid molecule may be produced or synthesized by the following methods: (i) in-vitro amplification, such as polymerase chain reaction (PCR) amplification; (ii) cloning and recombination; (iii) purification, such as digestion and gel electrophoresis separation; or (iv) synthesis, such as chemical synthesis. In some embodiments, the isolated nucleic acid molecule is prepared by the recombinant DNA technology.

In another aspect, the present application provides a vector, which may contain the nucleic acid molecule. In the present application, the vector can be selected from one or more of a plasmid, a retroviral vector and a lentiviral vector. The lentiviral vector of the present application may comprise the CAR. For example, the lentiviral vector of the present application may comprise a nucleotide sequences of SEQ ID NO: 50 and/or SEQ ID NO: 52 or functional variants thereof. In addition, the vector can also contain other genes, for example, a marker gene allowing the vector to be selected in a suitable host cell and under an appropriate condition. In addition, the vector can also contain an expression control element that allows the coding region to be correctly expressed in a suitable host. Such a control element is well-known to those skilled in the art, and, for example, can include a promoter, a ribosome-binding site, an enhancer, and other control elements for regulating gene transcription or mRNA translation. In some embodiments, the expression control sequence is a regulable element. The specific structure of the expression control sequence can be varied according to the functions of species or cell types, but generally contains a 5' non-transcribed sequence and 5' and 3' non-translated sequences which participate in the transcription initiation and the translation initiation respectively, such as a TATA box, a capped sequence, a CAAT sequence, etc. For example, 5' non-transcribed expression control sequence can contain a promoter region, which can comprise a promoter sequence for transcribing and controlling functionally-linked nucleic acids. The one or more nucleic acid molecules of the present application can be operably linked to the expression control element. The vector can include, for example, plasmids, cosmids, viruses, bacteriophages or other vectors commonly used in, for example, genetic engineering. For example, the vector is an expression vector, including a vector scFv plasmid and/or a CAR plasmid.

In some embodiments, the virus-involved vector may be a lentiviral vector that may comprise vector scFv plasmids and/or CAR plasmids. For example, the virus may be a lentivirus LV0002, which may comprise a vector scFv plasmid PXL0008 that may comprise a nucleic acid scFv0008 molecule, and/or a CAR plasmid PXL0009 that may comprise a nucleic acid CAR0009 molecule. For example, the virus may be a lentivirus LV0011, which may comprise a vector scFv plasmid PXL0008 that may comprise a nucleic acid scFv0008 molecule, and/or a CAR plasmid PXL0041 that may comprise a nucleic acid CAR0041 molecule. For example, the virus may be a lentivirus LV0007, which may a vector scFv plasmid PXL0026 that may comprise a nucleic acid scFv0026, and/or a CAR plasmid PXL0037 that may comprise a nucleic acid CAR0037. For example, the virus may be a lentivirus LV0020, which may a vector scFv plasmid PXL0026 that may comprise a nucleic acid scFv0026, and/or a CAR plasmid PXL0085 that may comprise a nucleic acid CAR0085. For example, the virus may be a lentivirus LV0021, which may a vector scFv plasmid PXL0026 that may include a nucleic acid scFv0026, and/or a CAR plasmid PXL0087 that may include a nucleic acid CAR0087. In some embodiments, the virus-involved vector may comprise retroviral vectors, which may be the scFv plasmids and/or the CAR plasmids.

In another aspect, the present application provides an immune effector cell that may comprise the CAR, the nucleic acid molecule or the vector of the present application. In the present application, the immune effector cell can be a mammalian cell. In the present application, the immune effector cell can be selected from a T lymphocyte and a natural killer (NK) cell.

In the present application, the T lymphocyte may comprise thymocyte, natural T lymphocyte, immature T lymphocyte, mature T lymphocyte, resting T lymphocyte or activated T lymphocyte. The T cell may be a helper T cell (Th), such as a helper T cell 1 (Th1) or a helper T cell 2 (Th2). The T lymphocyte may be a $CD4^+$ helper T cell (HTL; $CD4^+$ T cell), a cytotoxic T cell (CTL; $CD8^+$ T cell), a tumor-infiltrating cytotoxic T cell (TIL; $CD8^+$ T cell), a $CD4^+/CD8^+$ T cell, a $CD4^-/CD8^-$ T cell or any other T lymphocyte subtypes. In some embodiments, the T lymphocyte may be a naive T cell ($T_N$ cell). In some embodiments, the T lymphocyte may be a central memory T cell ($T_{CM}$ cell). In some embodiments, the T lymphocyte may be an effector T cell ($T_{EM}$ cell). In some embodiments, the T lymphocyte may be a NK T cell. In the present application, the T lymphocyte may be derived from peripheral blood cells, umbilical cord blood cells and/or leukocytes.

In the present application, the T lymphocyte may be a $T_{CM}$ cell, which may have the characteristics of $CD45RO^+/CD62L^+$. The T lymphocyte may be a $T_{EM}$ cell, which may have the characteristics of $CD45RO^{+/CD}62L^-$. The T lymphocyte may be a $T_N$ cell, which may have the characteristics of $CD45RO^-/CD62L^+$. The T lymphocyte may be a NK T cell, which may be subdivided as $NK1.1^+$, $NK1.1^-$, $CD4^+$, $CD4^-$, $CD8^+$ and $CD8^-$. After activated, the NK T cell can produce a large number of interferon $-\gamma$, IL-4 (interleukin 4) and granulocyte-macrophage colony-stimulating factor. In addition, the NK T cell can also produce some cytokines and chemotactic factors (such as IL-2, IL-13, IL-17, IL-21 and tumor necrosis factor-$\alpha$).

In another aspect, the present application provides a method for preparing the immune effector cell, which may comprise introducing the vector of the present application into the immune effector cell. For example, the vector of the present application can be introduced into the immune effector cell, such as the T lymphocyte or the natural killer (NK) cell. In some embodiments, each type of or each cell may comprise one or one type of vector of the present application. In some embodiments, each type of or each cell may comprise multiple (such as two or more) or multiple types (such as two or more types) of vectors of the present application. In the present application, the vector of the present application can be introduced into the immune effector cell by a method known in the art when it is needed. For example, the immune effector cell can be transfected by the retroviral vector to integrate a viral genome carrying the CAR molecule into a host genome, ensuring the long-term, stable expression of a target gene. For another example, the transposon can be utilized to introduce a CAR-carrying plasmid (transposon) and a transposase-carrying plasmid into a target cell. For another example, the CAR molecule can be added into the genome by a gene editing method (such as CRISPR/Cas9). In the present application, the CAR molecule-carrying vector of the present application can be introduced into the cell by a method known in the art, such as electroporation, lipofectamine (lipofectamine 2000, Invitrogen), etc.

In another aspect, the present application provides a composition, which may comprise the immune effector cell and a pharmaceutically acceptable adjuvant.

The pharmaceutically acceptable adjuvants may comprise buffer, antioxidant, preservative, low-molecular weight polypeptide, protein, hydrophilic polymer, amino acid, sugar, chelating agent, counter-ion, metal complex and/or nonionic surfactant.

In the present application, the composition may be prepared for oral administration, intravenous administration (such as intravenous injection, I.V), intramuscular administration (such as intramuscular injection, I.M.), in-situ administration in a tumor site, inhalation, rectal administration, vaginal administration, transdermal administration or subcutaneous repository administration.

The composition of the present application may contain a therapeutically effective amount of the antibody or antigen-binding fragment thereof. The therapeutically effective amount is a dose required to prevent and/or treat (at least partially treat) a disease (such as cancer) and/or any complication thereof in a subject having that disease or a development risk therefor.

Pharmaceutical Use

In another aspect, the present application provides a use of the CAR, the nucleic acid molecule, the vector or the immune effector cell in the preparation of drugs, wherein the drugs are used to treat diseases or conditions associated with the expression of BCMA.

In the present application, the diseases or conditions associated with the expression of BCMA may be cancers or malignant tumors. In some embodiments, the cancers or malignant tumors may be selected from plasmocyte malignancy diseases, such as multiple myeloma, and may also be selected from B-cell malignant diseases, such as Hodgkin's lymphoma and non-Hodgkin's lymphoma.

In another aspect, the present application provides the CAR, the nucleic acid molecule, the vector or the immune effector cell, treating diseases or conditions associated with the expression of BCMA.

In another aspect, the present application provides a method for treating diseases or conditions associated with the expression of BCMA, comprising administering the CAR, the nucleic acid molecule, the vector or the immune effector cell to a patent.

Without intending to be bound by any theory, the following examples are merely intended to illustrate the working modes of the chimeric antigen receptor, vector, cell and composition of the present application, rather than to limit the scope of the invention of the present application.

EXAMPLES

Example 1

Construction of Recombinant Lentiviral Vectors

The following nucleotide sequences were first artificially synthesized: KOZAK (the nucleotide sequence of SEQ ID NO: 2), CD8a signal peptide (the nucleotide sequence SEQ ID NO: 4), HA-tag (the nucleotide sequence SEQ ID NO: 6), scFv0026 (the nucleotide sequence of SEQ ID NO: 44), hinge region (the nucleotide sequence SEQ ID NO: 26), transmembrane domain (the nucleotide sequence SEQ ID NO: 28), CD28 costimulatory factor (the nucleotide sequence SEQ ID NO: 30), 4-1BB costimulatory domain (the nucleotide sequence SEQ ID NO: 32), CD3 intracellular signal transduction domain (the nucleotide sequence SEQ ID NO: 34), T2A cleaving peptide (the nucleotide sequence SEQ ID NO: 36), GFP (the nucleotide sequence SEQ ID NO: 38), and EGFRt (the nucleotide sequence SEQ ID NO: 40).

Meanwhile, a scFv0008 molecule was constructed as a control, and the scFv0008 molecule comprises an amino acid sequence of SEQ ID NO: 41 (see US9034324, SEQ ID NO: 3 and SEQ ID NO: 4).

The HA-tag was located at the N terminal of the CAR molecule, and directly linked to the CD8a signal peptide. When the CAR molecule was expressed on the cell surface, the HA-tag could serve as a tag for detecting the CAR molecule or enriching of the CAR-T cell. In addition, the GFP was located at the most C terminal of the CAR molecule, and directly linked to the T2A cleaving peptide. The CAR molecule and the GFP protein in equal amounts could be formed after the T2A cleaving (see Szymczak, et al., correction of multi-gene deficiency in vivo using a single self-cleaving 2A peptide-based retroviral vector, nature biotechnology, 2004. 22: p. 589). Therefore, the expression process (as shown in FIG. 1B) of the CAR molecules could be indirectly evaluated by detecting the GFP signal. FIG. 1B specifically shows the detection process: a lentiviral particle (1) being introduced into a cell by the cell membrane fusion (2); the package being removed (3); then the reverse transcription (4) being performed; the integration (5), transcription (6) and translation (7) then being performed; and the cleaving (8) being performed by the T2A cleaving peptide. The transduction efficiency can be evaluated by the expression of the GFP (9), the binding efficiency of the scFv and BCMA protein can be studied by BCMA-Fc (10), and the anti-HA antibody can be used to detect the expression of the CAR and enrich the CAR-T cell for functionality analysis (11).

Besides by detecting the GFP protein, the expression of the CAR molecule can also be determined by other methods. For example, an appropriate amount of biotinylated BCMA and PE streptavidin can be used to mark the CAR molecule so that the expression of the CAR molecule can be reflected by PE signals. For another example, an appropriate amount of biotinylated anti-HA monoclonal antibody (biotinylated anti-HA mAb) and PE streptavidin can be used to mark the CAR molecules for detection.

The scFv molecule-contained plasmids, the CAR molecule-contained plasmids and the lentiviruses corresponding thereto used in the present application are shown in Table 1.

TABLE 1

| | Types of Lentiviral Vectors | | | | |
|---|---|---|---|---|---|
| No. | scFv plasmid | scFv molecule | CAR plasmid | CAR molecule | Lentivirus |
| 1 | PXL0008 | scFv0008 | PXL0009 | CAR0009 | LV0002 |
| 2 | PXL0008 | scFv0008 | PXL0041 | CAR0041 | LV0011 |
| 3 | PXL0026 | scFv0026 | PXL0037 | CAR0037 | LV0007 |
| 4 | PXL0026 | scFv0026 | PXL0085 | CAR0085 | LV0020 |
| 5 | PXL0026 | scFv0026 | PXL0087 | CAR0087 | LV0021 |

The following CAR plasmids were prepared (see FIG. 1A).

A lentiviral vector PLVX-EFlalpha-IRES-Puro was double digested with NotI and MluI, and the vector fragment was recovered. The candidate scFv plasmid PXL0026 (the nucleotide sequence of SEQ ID NO: 44) was amplified by PCR, and at the 5' terminal in sequence added a NotI restriction enzyme cutting site (containing a protective base), a CD8a signal peptide, an HA-tag by extension PCR; the gene synthesis of a hinge region, a transmembrane domain, a CD28 costimulatory factor and a CD3 intracellular signal transduction domain and then the PCR amplification was conducted; a T2A cleaving peptide and an eGFP were obtained from a plasmid pMy-BirA-T2A-eGFP by PCR amplification, with a MluI restriction enzyme cutting site and a protective base on the 3' terminal; and then a PCR fragment, with a NotI restriction enzyme cutting site at the 5' terminal and a MluI restriction enzyme cutting site at the 3' terminal, was obtained by overlap PCR, the obtained fragment was double digested with NotI and MluI, and was recovered. The CAR plasmid numbered as PXL0037 was constructed through T4 ligation (the nucleotide sequence of CAR0037 was shown as SEQ ID NO: 50).

The CAR plasmid numbered as PXL0085 was obtained by a similar method. A lentiviral vector PLVX-EFlalpha-IRES-Puro was double digested with NotI and MluI, and the vector fragment was recovered. The candidate scFv plasmid PXL0026 was amplified by PCR, and at the 5' terminal in sequence added a NotI restriction enzyme cutting site (containing a protective base), a CD8a signal peptide by extension PCR; the gene synthesis of a hinge region, a transmembrane domain, a 4-1BB costimulatory factor (the nucleotide sequence of SEQ ID NO: 32) and a CD3 intracellular signal transduction domain and the PCR amplification was performed; then a PCR fragment, with a NotI restriction enzyme cutting site at the 5' terminal and a MluI restriction enzyme cutting site at the 3' terminal, was obtained by overlap PCR, the obtained fragment was double digested with NotI and MluI, and the fragment was recovered. The CAR plasmid numbered as PXL0085 was constructed through T4 ligation (the nucleotide sequence of the CAR molecule portion of CAR0085 was shown as SEQ ID NO: 52).

The CAR plasmid numbered as PXL0087 was obtained by a similar method. A lentiviral vector PLVX-EFlalpha-IRES-Puro was double digested with NotI and MluI, and the vector fragment was recovered. The candidate scFv plasmid PXL0026 was amplified by PCR, and at the 5' terminal in sequence added a NotI restriction enzyme cutting site (containing a protective base), a CD8a signal peptide by extension PCR; the gene synthesis of a hinge region, a transmembrane domain, a 4-1BB costimulatory factor (the nucleotide sequence of SEQ ID NO: 32), a CD3 intracellular signal transduction domain, a T2A cleaving peptide and EGFRt (the nucleotide sequence of SEQ ID NO: 40) and the PCR amplification was performed; then a PCR fragment, with a NotI restriction enzyme cutting site at the 5' terminal and a MluI restriction enzyme cutting site at the 3' terminal, was obtained by overlap PCR, the obtained fragment was double digested with NotI and MluI, and the fragment was recovered. The CAR plasmid numbered as PXL0087 was constructed through T4 ligation (the nucleotide sequence of the CAR molecule portion of CAR0087 was shown as SEQ ID NO: 52).

Meanwhile, a CAR plasmid containing the scFv plasmid PXL0008 was constructed as a control.

The CAR plasmid numbered as PXL0041 was obtained through the same method (the nucleotide sequence of the CAR molecule portion of CAR0041 was shown as SEQ ID NO: 48). A lentiviral vector PLVX-EF1alpha-IRES-Puro was double digested with NotI and MluI, and the vector fragment was recovered. The candidate scFv plasmid PXL0008 (the nucleotide sequence of SEQ ID NO: 42) was amplified by PCR, and at the 5' terminal in sequence added a NotI restriction enzyme cutting site (containing a protective base), a CD8a signal peptide, an HA-tag by extension PCR; the gene synthesis of a hinge region, a transmembrane domain, a CD28 costimulatory factor and a CD3 intracellular signal transduction domain and then the PCR amplification was conducted; a T2A cleaving peptide and an GFP were obtained from a plasmid pMy-BirA-T2A-eGFP by PCR amplification, with a MluI restriction enzyme cutting site and a protective base on the 3' terminal; and then a PCR fragment, with a NotI restriction enzyme cutting site at the 5' terminal and a MluI restriction enzyme cutting site at the 3' terminal, was obtained by overlap PCR, the obtained fragment was double digested with NotI and MluI, and the fragment was recovered. The CAR plasmid numbered as PXL0041 was constructed through T4 ligation (the nucleotide sequence of the CAR molecule portion of CAR0041 was shown as SEQ ID NO: 48).

The CAR plasmid numbered as PXL0009 was obtained by a similar method. A lentiviral vector PLVX-EFlalpha-IRES-Puro was double digested with NotI and MluI, and the vector fragment was recovered. The candidate scFv plasmid PXL0008 was amplified by PCR, and at the 5' terminal in sequence added a NotI restriction enzyme cutting site (containing a protective base), a CD8a signal peptide; the gene synthesis of a hinge region, a transmembrane domain, a CD28 costimulatory factor and a CD3 intracellular signal transduction domain and the PCR amplification was performed; then a PCR fragment, with a NotI restriction enzyme cutting site at the 5' terminal and a MluI restriction enzyme cutting site at the 3' terminal, was obtained by overlap PCR, the obtained fragment was double digested with NotI and MluI, and the fragment was recovered. The CAR plasmid numbered as PXL0009 was constructed through T4 ligation (the nucleotide sequence of the CAR molecule portion of CAR0009 was shown as SEQ ID NO: 46).

Example 2

Expressions of CAR Molecules on Transiently-Transfected 293T Cell Samples

Figure 2:
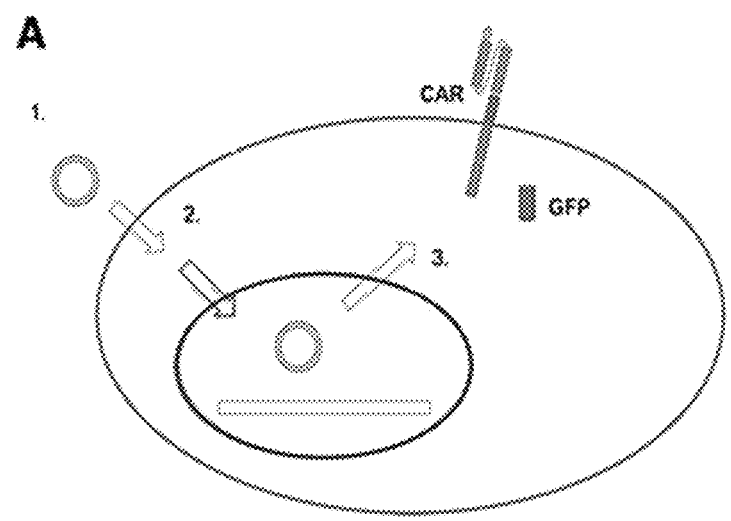
FIG. 2A shows a schematic diagram of the process of transiently transfecting T cells with the CAR plasmids of the present application.
FIG. 2B shows the expression of CAR molecules in the T cells transiently transfected with the CAR plasmids of the present application.
Figure 2:
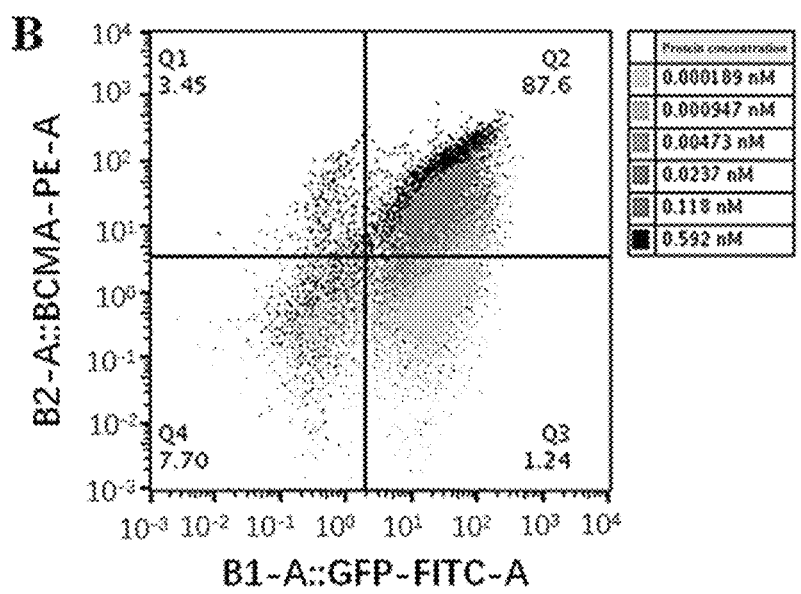

As shown in FIG. 2A, the CAR plasmids PXL0009, PXL0041 and PXL0037 prepared in example 1 were transiently transfected into 293T cells using PEI as the transfection reagent, so that a PXL0009-293T cell, a PXL0041-293T cell and a PXL0037-293T cell were respectively obtained. At 72 hours after transient transfection, the PXL0009-293T cell, the PXL0041-293T cell and the PXL0037-293T cell were used to evaluate the expression capabilities of the candidate CAR molecules. In FIG. 2A, 1 represented a plasmid and a transfection reagent, 2 represented transient transfection, and 3 represented expression and T2A cleaving peptide cleaving.

The expressions of the CAR molecules were evaluated by utilizing the methods in example 1. Specifically, the dose of the biotinylated BCMA was changed by gradient dilution in the presence of excessive PE streptavidin with a fixed concentration, so that the change of PE signals (shown in FIG. 2B) was obtained. X axis represented GFP protein signals expressed in the cells, and Y axis represented PE signals obtained by the CAR molecules marked using the gradiently-diluted biotinylated BCMA and the fixed amount of PE streptavidin.

Figure 3:
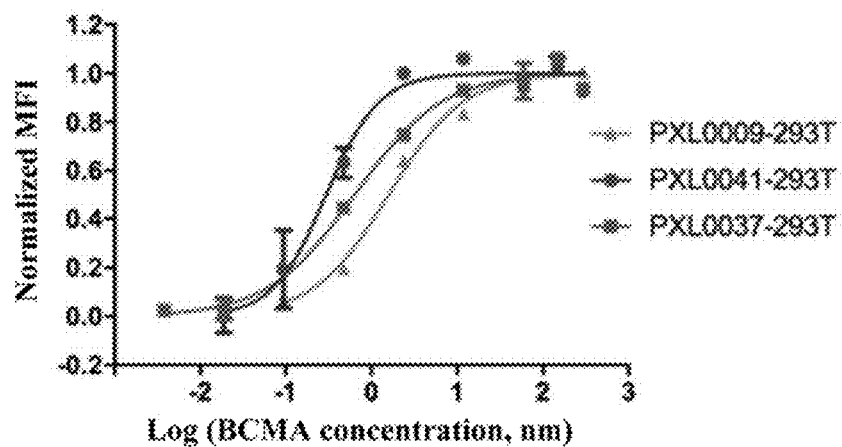
FIG. 3 shows the expression of CAR molecules in the T cells transiently transfected with the CAR plasmids of the present application.

The gradiently-diluted biotinylated BCMA protein (295.86 nM to 3.79 pM) was used to assay the 293T cells transiently transfected with the candidate CAR plasmids, so that a PE signal change curve (shown in FIG. 3) was obtained. $EC_{50}$ values for BCMA proteins binding of CAR molecules on the cell surface calculated by curve fitting were shown in Table 2.

TABLE 2

Results of Expressions of CAR Molecules by detecting GFP Proteins

| Sample | GFP % | Percentage of CAR marked with 500 ng of BCMA | CAR %: GFP % | $EC_{50}$ (nM) |
|---|---|---|---|---|
| PXL0037-293T | 38.5 | 9.2 | 0.24 | 0.64 |
| PXL0041-293T | 41.8 | 16.1 | 0.39 | 0.30 |
| PXL0009-293T | N/A | 18.0 | N/A | 1.59 |

Similarly, the 293T cell samples at 72 hours after transient transfection, the CAR molecules were marked by using the biotinylated anti-HA monoclonal antibody (anti-HA mAb) and the PE streptavidin, and then GFP positive rates (GFP %), CAR positive rates (CAR %), and ratios of them were obtained by flow cytometry. The results were shown in Table 3.

TABLE 3

Flow Cytometry Results for Expressions of CAR Molecules

| Sample | GFP % | Percentage of CAR marked with 500 ng of anti-HA mAb | CAR %: GFP % |
|---|---|---|---|
| PXL0037-293T | 35.9 | 29.4 | 0.82 |
| PXL0041-293T | 43.1 | 18.8 | 0.44 |
| PXL0009-293T | N/A | N/A | N/A |

PXL0009 was a well-known reference plasmid that could normally express the CAR molecule, which did not contain genes encoding the GFP protein and the HA tag, and its sequence was shown as SEQ ID NO: 45. The GFP signal in the cell sample could not be detected, nor PE signal for the binding of a CAR with a biotinylated anti-HA monoclonal antibody (biotinylated anti-HA mAb). Therefore, a PXL0009-293T cell sample could be used as a control sample for flow cytometry. Different from PXL0009, PXL0041 and PXL0037 as reference plasmids could encode the GFP protein and the HA tag, so that GFP signals could be detected in a PXL0041-293T cell sample, and the binding (PE signal) of the CAR with the biotinylated BCMA protein or the biotinylated anti-HA monoclonal antibody could also be detected respectively, therefore, they could serve as positive controls.

The result showed that both the GFP signal and the binding (PE signal) of the CAR with the biotinylated BCMA protein or the biotinylated anti-HA monoclonal antibody (biotinylated anti-HA mAb) could be detected in a PXL0037-293T cell sample, demonstrating that the CAR molecule encoded by the PXL0037 plasmid could be expressed on cells and could normally bind with the BCMA protein.

Example 3

Expressions of CAR Molecules on Lentivirus-Transduced 293T Cell Samples 3.1. Packaging of Lentiviruses The CAR plasmids numbered as PXL0009, PXL0041 and PXL0037 that were prepared in example 1 with a shuttle plasmid and other packaging plasmids were co-transfected simultaneously into 293T cells, so that the lentiviruses were packaged in the cells. The specific steps were as follows.

Taking lentivirus packaging in 10 cm culture dishes as an example, the 293T cells were inoculated into DMEM medium containing 10% of FBS at a density of $6 \times 10^4$ cells/cm$^2$, and were cultured in the environment of 37° C., 5% $CO_2$ and saturated humidity for 3 days, and then the transfection was conducted. Before transfection, two EP tubes were prepared with 500 μl of opti-MEM in each EP tube, wherein, 3 μg of lentiviral helper vector PSPAX2, 2 of lentiviral helper vector pMD2.G and 5 μg of the vector prepared in example 1 (CAR plasmid numbered as PXL0009, PXL0041 or PXL0037) were added to one tube and the mixture solution was thoroughly mixed, so that a tube containing plasmid was obtained; and 30 μl of PEI with a concentration of 1 mg/ml was added to the other tube and the mixture solution was thoroughly mixed. The solution containing PEI in the other tube was then added dropwise to the tube containing the plasmid while the obtained solution was mixed, and 30 minutes after standing at room temperature, the resultant solution was uniformly added to the aforementioned 293T cells dropwise. 24 hours after transfection, the medium was changed to 6 ml of DMEM medium containing 10% of FBS.

72 hours later, the supernatant was collected and added to a centrifuge tube, and then was centrifuged at 3000 g under 4° C. for 10 minutes, and the supernatant was ready for purification after filtered by a 0.45 μm filter.

The supernatant was centrifuged by an ultracentrifuge at 27000 g under 4° C. for 4 hours. The supernatant was removed, the precipitate was resuspended with 100 μl of pre-cooled PBS, and then the mixture solution was mixed until no particle existed. The obtained solution was placed overnight at 4° C. Then the virus suspension was taken out and dispensed. Lentiviruses LV0002 (corresponding to the CAR plasmid PXL0009), LV0011 (corresponding to the CAR plasmid PXL0041) and LV0007 (corresponding to the CAR plasmid PXL0037) were obtained respectively.

3.2. Evaluation of Packaging Efficiencies of Lentiviruses

By detecting viral titers (biological titers) with transduction activities in the supernatant obtained in the process of lentiviral packaging, the packaging efficiencies of lentiviruses were evaluated. The specific assay steps were as follows.

293T cells were inoculated into a six-well plate in a quantity of $1 \times 10^5$ cells/well, and were cultured with 500 μl of DMEM medium containing 10% of FBS in the environment of 37° C., 5% $CO_2$ and saturated humidity. After the cells were cultured for 24 hours, 100 μl, 50 μl, 25 μl and 12.5 μl of the supernatant above-mentioned were taken and added to six-well plates (two wells for each sample volume) for lentiviral transduction. After the lentiviral transduction, the cells were then continued to be cultured in the environment of 37° C., 5% $CO_2$ and saturated humidity. 72 hours after the lentiviral transduction, the 293T cells were digested and resuspended for flow cytometry.

Figure 4:
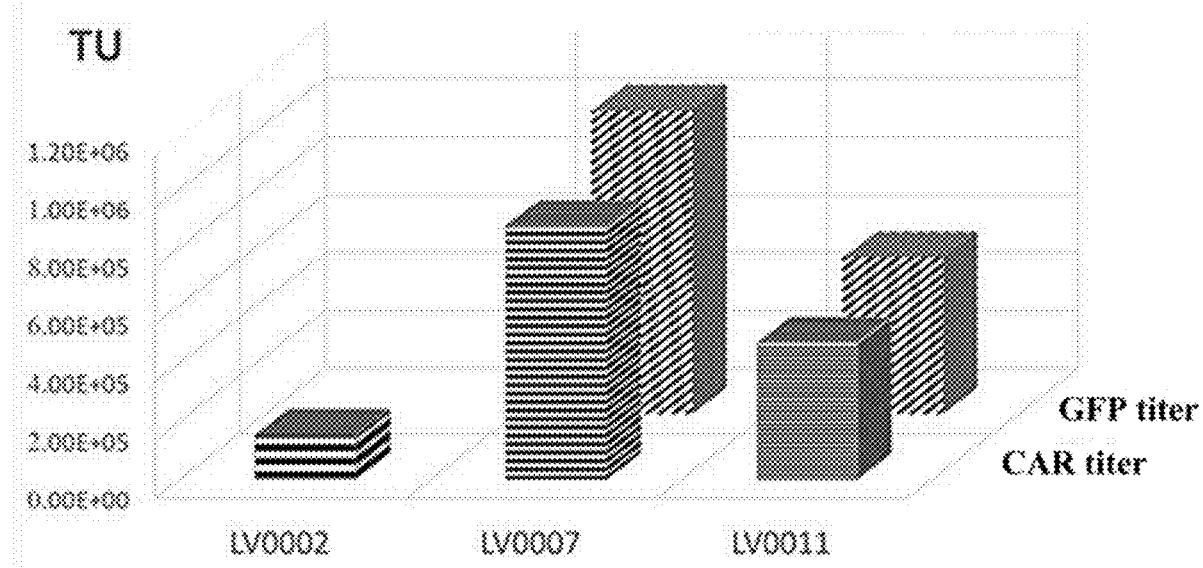
FIG. 4 shows results of a biological titer assay for the CAR plasmids of the present application packed with lentivirus.

As both the CAR molecular-encoding gene and the GFP protein-encoding gene were carried in LV0007, so both the CAR molecule and the GFP protein could be expressed in 293T cells transduced with LV0007. By detecting the GFP fluorescence signals in the 293T cells through the flow cytometry, the lentiviral biological titer (referred to as GFP titer) in the supernatant could be calculated:

biological titer(TU/ml)=(GFP positive rate×293T cell number)/virus sample volume Or, the LV0007-transduced 293T cells were marked with the biotinylated BCMA and the PE-streptavidin, and the CAR positive rate (referred to as CAR titer) was detected through the flow cytometry:

biological titer (TU/ml)=(CAR positive rate×293T cell number)/virus sample volume The biological titer assay results for supernatants obtained in the aforementioned packaging process were shown in FIG. 4 and Table 4.

Table 4 showed the biological titer data of supernatants for lentiviral packaging. "GFP titer" generally referred to a titer that was calculated by detecting the GFP positive rate in to-be-detected virus-transduced 293T cells through GFP signals; and "CAR titer" generally referred to a titer that was calculated by detecting the CAR positive rate in to-be-detected virus-transduced 293T cells with the biotinylated BCMA and the PE-streptavidin.

TABLE 4

Biological Titer Assay Results for Lentiviral Packaging

| Sample | CAR titer (TU/ml) | GFP titer (TU/ml) |
|---|---|---|
| LV0002 | 1.52E+05 | N/A |
| LV0007 | 8.73E+05 | 1.05E+06 |
| LV0011 | 4.68E+05 | 5.38E+05 |

Example 4

Preparation of CAR-T Cells

On day 1, about 65 ml of peripheral blood was collected from a healthy donor, Ficoll was used for separation to obtain PBMCs, and then CD3 MicroBeads was further used for sorting out T cells. The obtained T cells were further activated by using CD3/CD28 Dynabeads. About 24 hours after the activation (on day 2), the lentiviruses LV0007 and LV0011 prepared in example 3 were added respectively for transduction (MOI=4), with a T cell density of about $1.5\times10^6$ cells/ml during the transduction. On day 3, the transduced T cells were refreshed with new medium once. Afterwards, counting was performed every day, the cell density was kept between $0.6\times10^6$ cells/ml and $2.0\times10^6$ cells/ml, and the growth curve of the cells was plotted.

On day 6 of the cell culture, a CAR positive rate (CAR %), a GFP positive rate (GFP %) and a CD4/CD8 ratio were detected by the flow cytometry. On day 10, the functions of CAR-T cells were evaluated in vitro.

According to the aforementioned process, LV0007-CAR-T and LV0011-CAR-T cells were obtained, and the T cells of the donor were adopted as a control. Table 5 summarized the aforementioned preparation process for CAR-T cells.

TABLE 5

Preparation Process of CAR-T Cells

| Time | Event | Data |
|---|---|---|
| Day 1 | Collecting peripheral blood from a healthy donor | 65 ml |
| | Obtaining PBMCs by Ficoll separation | $2.05 \times 10^8$ cells |
| | Obtaining T cells by CD3 MicroBeads sorting | $9.16 \times 10^7$ cells |
| | Time for activation by CD3/CD28 Dynabeads | ~24 h |
| | CAR-T cell medium condition | CTS OpTmizer, 1% CTS Immune Cell SR, 50-200 IU/ml IL-2, 1% L-Glu |
| Day 2 | Lentiviral transduction of T cells | MOI = 4, cell concentration = $1.49 \times 10^6$ cells/ml; Except not adding lentiviruses, other operations for the T cell control group are the same as those for the CAR-T cell group. |
| Day 6 | Determination of CAR positive rate | Data are as shown in Table 6. |
| Day 10 | CD107a degranulation test | Data are as shown in Table 8 and FIG. 10. |

Figure 5:
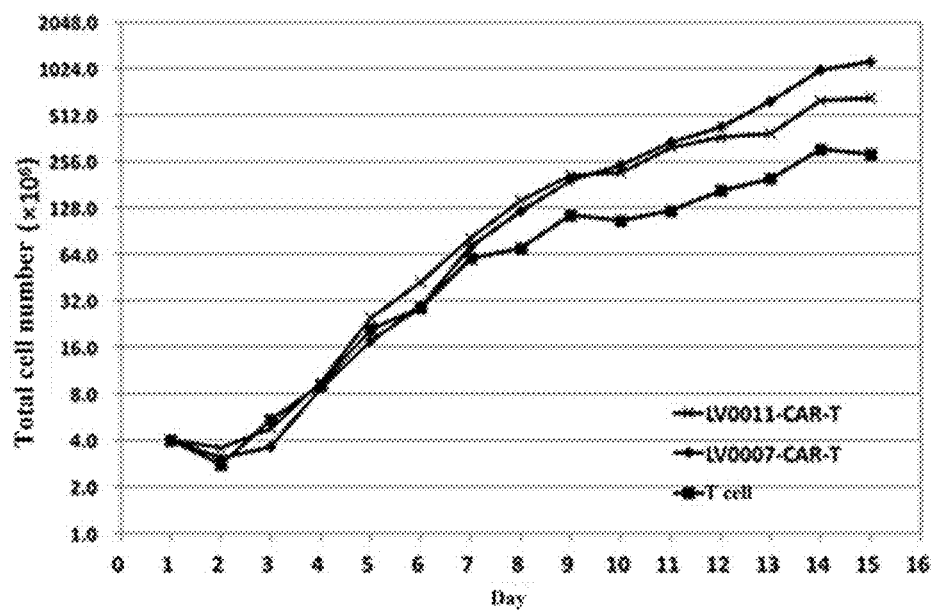
FIG. 5 shows the growth of the CAR-T cells of the present application.

Growth curves for the LV0007-CAR-T cell group, the LV0011-CAR-T cell group and the T cell control group were as shown in FIG. 5. Data such as the CAR positive rates that were obtained by the flow cytometry on day 6 of the cell culture were shown in Table 6.

TABLE 6

Results of CAR Positive Rate Assay by Flow Cytometry

| Sample | CAR % | CAR MFI | CD8% | CAR % in CD4 | CAR % in CD8 |
|---|---|---|---|---|---|
| LV0007-CAR-T | 56.3 | 25.1 | 35.6 | 54.0 | 56.5 |
| LV0011-CAR-T | 62.8 | 30.7 | 37.6 | 58.3 | 68.5 |
| Tcell | N/A | N/A | 29.6 | N/A | N/A |

Example 5

Data for the Binding of CAR Molecules with the BCMA Protein

Figure 6:
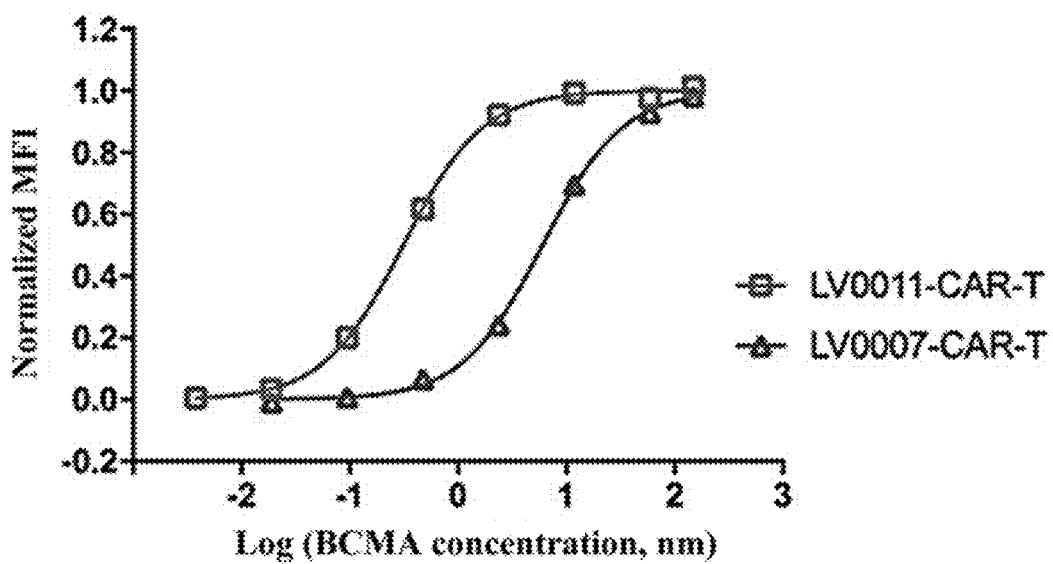
FIG. 6 shows results of the ability of the CAR molecules of the CAR-T cells of the present application to bind with the BCMA protein.

Further, the capabilities of CAR molecules expressed on the CAR-Ts prepared in example 4 to bind with the BCMA protein were detected by using gradiently-diluted biotinylated BCMA protein to mark CAR molecules (identical with the method in example 2) in the presence of excessive PE streptavidin with a fixed concentration. The results were shown in FIG. 6 and Table 7.

TABLE 7

Results for Binding of CAR Molecules with the BCMA Protein

| Sample | $EC_{50}$ |
|---|---|
| LV0007-CAR-T | 6.00 |
| LV0011-CAR-T | 0.31 |

According to the aforementioned data, the candidate CAR molecules expressed on the T cells could normally bind to the BCMA protein. However, there was a significant difference between determined $EC_{50}$ values for cell samples prepared in different batches. Such a difference might be caused by the different densities of the CAR molecules expressed on the surfaces of the cells due to the different cell types, sample preparation methods and batches.

Example 6

CD107a Degranulation Test 6.1. CD107a Degranulation Test

The biological potency of the CAR-T cells was evaluated in vitro by the CD107a Degranulation Test. CD107a is a marker of an intracellular microvesicle. When the microvesicle loaded with granzyme is fused with a cell membrane, the quantity of CD107a on the cell membrane is increased. Therefore, when the CD107a recovery is blocked by using monesin (obtained from BioLegend), the intensity of microvesicle release can be quantitatively reflected. After the CAR-T is stimulated by a target antigen on a target cell, the granzyme is released. The activation of T cells can be determined by detecting the increase of CD107a through the flow cytometry.

Firstly, the CAR-T cells (LV0007-CAR-T cells or L00011-CAR-T cells) obtained in example 4, together with target cells U266, monesin and a CD107a antibody were incubated for 3 to 6 hours, wherein the CAR-T cells and the target cells had the same cell density of $5\times10^5$ cells/ml. Then, after the sample was marked with CD8 and PD1 antibodies, the flow cytometry was performed. The CAR positive cells among the CAR-T cells were detected by detecting coexpressed GFP, while CAR positive cells among L00011-CAR-T cells as a control were marked by biotinylated BCMA-Fc and PE streptavidin. In the test, K562 cells were co-incubated with CAR-T cells as the negative control, and the positive control was using a cocktail instead of target cells to activate the CAR-T cells.

Figure 7:
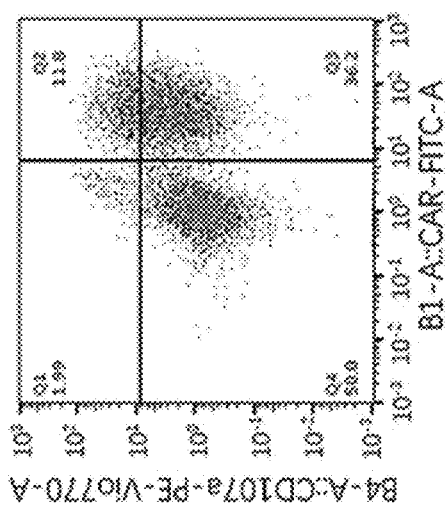
FIG. 7A and FIG. 7B show results of FACS analysis of CD107a degranulation tests for the CAR-T cells of the present application.
Figure 7:
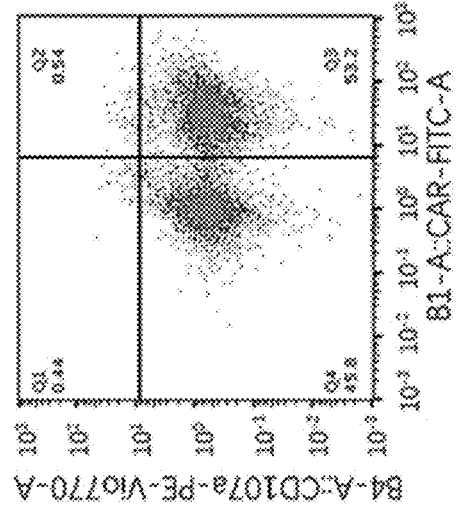
Figure 7:
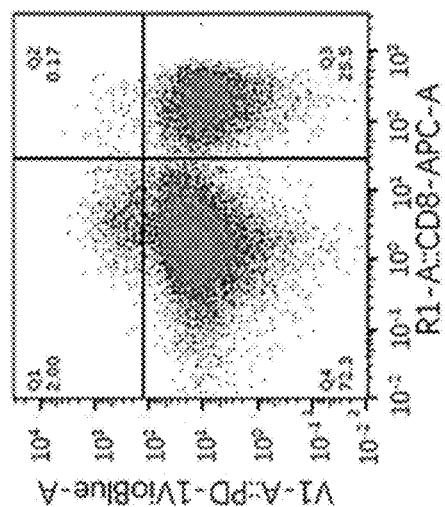
Figure 7:
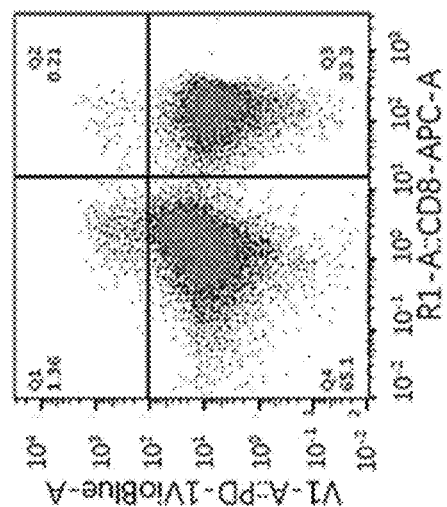
Figure 7:
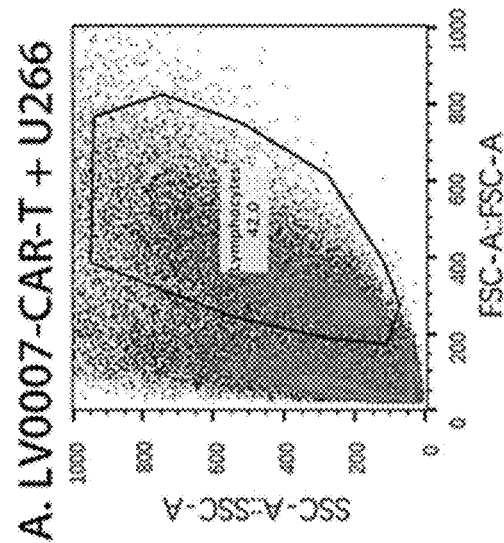
Figure 7:
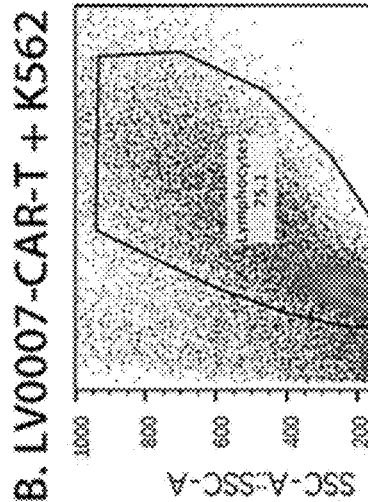

Taking LV0007-CAR-T cells as an example, the flow cytometry result was shown in FIG. 7A and FIG. 7B.

For the cell sample in which LV0007-CAR-T and U266 were co-incubated, a P1 gate was selected on the FSC:SSC scatter plot, and cell debris at the lower left corner were removed; for cells in the P1 gate, CD8:PD1 could be further analyzed to obtain a CD8+/PD1-cell population (Q3); and in the CD8+/PD1- cell population, GFP:CD107a could be analyzed again to obtain the proportion of the CD107a expressing in the CD8+/PD1-/CAR+ cell population (the CAR positive cell was marked by a coexpressed GFP signal) and the CD8+/PD1-/CAR- cell population respectively.

For the cell sample in which LV0007-CAR-T and K562 were co-incubated, the cells were divided into population P1 and population P2 on the FSC: SSC scatter plot, wherein nearly no CD8 was expressed on the cells in population P2, which therefore might be K562 cells; for cells in the P1 gate, CD8:PD1 could be further analyzed; in the CD8+/PD1- cell population (Q3), GFP: CD107a could be analyzed again to obtain the proportion of the CD107a expressing in each of CD8+/PD1-/CAR+ and CD8+/PD1-/CAR- as well.

6.2. CD107a Degranulation Test Data

According to the test operation in section 6.1 of example 6, the CAR-T cell samples (LV0007-CAR-T or L00011-CAR-T cells) were co-incubated with target cells U266 (BCMA-positive) or K562 (BCMA-negative) respectively for 3 hours, and then the flow cytometry was performed. The CD107a degranulation test data results for cell samples were shown in Table 8 and FIG. 8, and Table 8 and FIG. 8 both showed the ratios of the CD107a-expressing positive cells in the CD8+/PD1-/CAR+ cell subpopulation and the CD8+/PD1-/CAR- cell subpopulation.

TABLE 8

Ratios of CD107a-Expressing Positive Cells in Different Cell Subpopulations

| | CD8+/PD1-/CAR+ subpopulation | | CD8+/PD1-/CAR- subpopulation | |
|---|---|---|---|---|
| Sample | K562 | U266 | K562 | U266 |
| LV0007-CAR-T | 0.97 | 25.10 | 1.01 | 3.91 |
| LV0011-CAR-T | 2.01 | 10.70 | 2.71 | 3.33 |
| Tcell | N/A | N/A | 0.64 | 1.09 |

Figure 8:
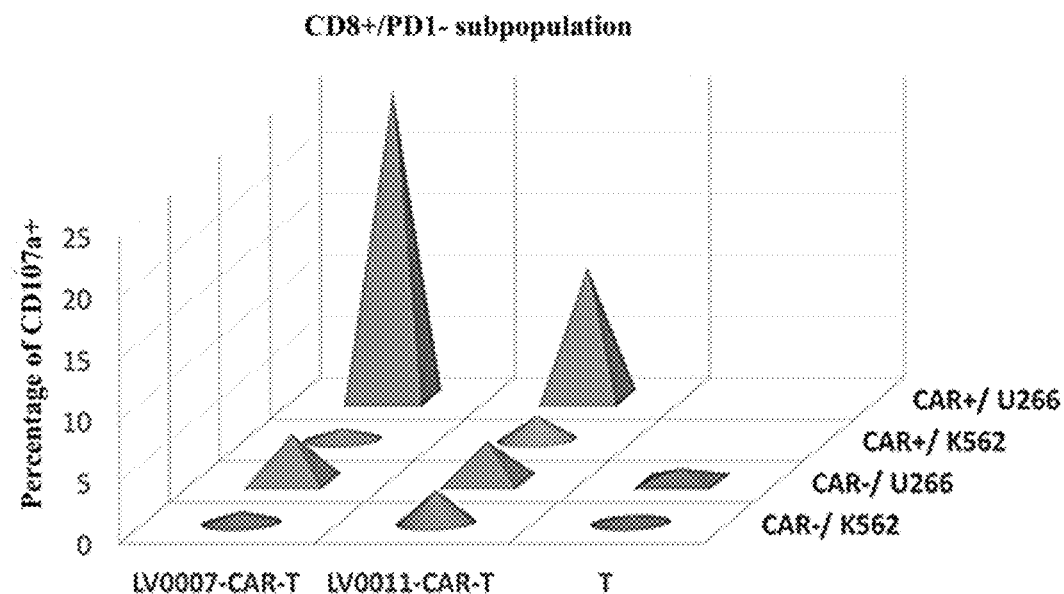
FIG. 8 shows results of CD107a degranulation test obtained after the incubation of CAR-T cells of the present application with different target cells.

As shown in Table 8 and FIG. 8, in the CAR-T sample co-incubated with U266, the CD107a value on the CD8+/PD1-/CAR+ cell subpopulation could reflect the situation where the CAR-T cells were specifically activated; while, in the CAR-T sample co-incubated with K562, the CD107a value on the CD8+/PD1-/CAR+ cell subpopulation could reflect the situation where the CAR-T cells were nonspecifically activated. By comparing the CD107a values on the CD8+/PD1-/CAR+ cell subpopulations from CAR-T samples co-incubated with U266, it could be concluded that the CD8+/PD1-/CAR+ subpopulation of LV0007-CAR-T cells could be specifically activated by the BCMA-positive cells (U266), and the activation for LV0007-CAR-T cells was stronger than that for L00011-CAR-T cells as a control.

6.3. CD107a Degranulation Test Data Under a BCMA Protein Competition Condition In addition, as the extracellular part of the BCMA protein expressed on the surface of a multiple myeloma (MM) cell could be cut by γ-secretase, a soluble BCMA (sBCMA) could be formed. The content of the soluble BCMA could be increased in the serum of a patient with MM, and its concentration was positively correlated with the malignant degree of a tumor. Therefore, when the CAR-T cells were co-incubated with target cells, 1 μg/ml of BCMA protein was added to the medium to evaluate the effect of the soluble BCMA on CAR-T cells activation.

Figure 9:
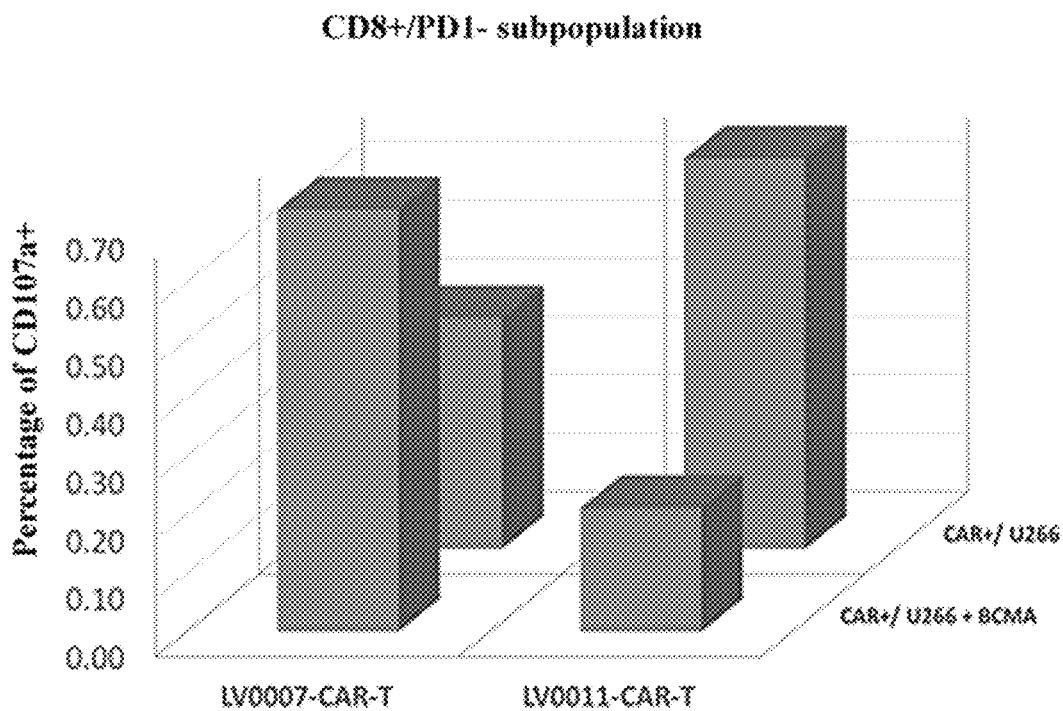
FIG. 9 shows results of CD107a degranulation test obtained after the incubation of CAR-T cells of the present application with different target cells under a BCMA protein competition condition.

The CD107a degranulation test results for the CAR-T cell samples under a BCMA protein competition condition were shown in Table 9 and FIG. 9. As shown in FIG. 9, the activation of the CAR-T cells by the U266 cells was not competitively suppressed by the BCMA protein in the LV0007-transduced cell sample; while the activation of the L00011-CAR-T cell sample as a control was significantly suppressed.

TABLE 9

CD107a Degranulation Test Data under a BCMA Protein Competition Condition

| | CD8+/PD1-/CAR+ subpopulation | | CD8+/PD1-/CAR- subpopulation | |
|---|---|---|---|---|
| Sample | U266 and BCMA | U266 | U266 and BCMA | U266 |
| LV0007-CAR-T | 72.46 | 39.61 | 7.51 | 2.95 |
| LV0011-CAR-T | 21.18 | 67.05 | 7.54 | 8.97 |
| Tcell | N/A | N/A | 0.00 | 8.58 |

Example 7

Determination of Cytokine Release

In a cytokine release determination experiment, after the to-be-determined CAR-T cells ($5\times10^5$ cells, 100 μl) and target cells ($5\times10^5$ cells, 100 μl) were co-incubated in RPMI-1640 medium for 24 hours, the cell culture supernatant was collected, and the secretions of IL-2, IL-4, IL-6, IL-10, IL-17A, TNF-α, IFN-γ and other factors were determined by the CBA method.

Figure 10:
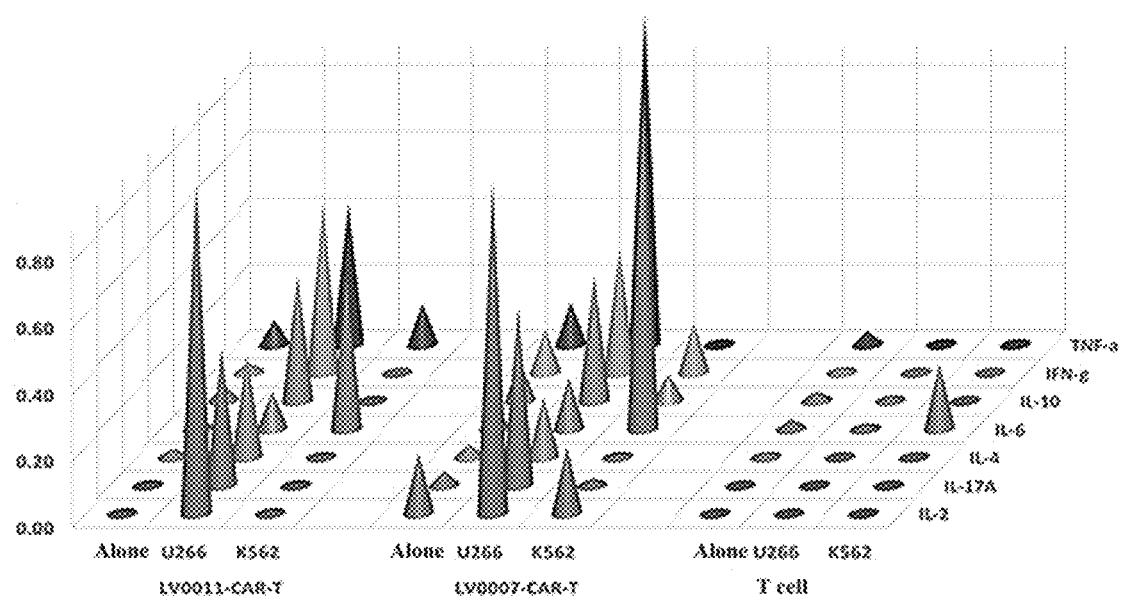
FIG. 10 shows results of cytokine-release assay obtained after the co-incubation of CAR-T cells of the present application with target cells.

The assay results of cytokine release, obtained after the CAR-T cell samples were co-incubated with the target cells respectively, as shown in Table 10 and FIG. 10. The release amount of a cytokine shown in FIG. 10 was a percentage relative to the detected maximum value in a sample. As shown in Table 10 and FIG. 10, the amounts of TNF-α, IFN-γ and IL-2 secreted by the LV0007-CAR-T cells stimulated by the BCMA-positive target cells U266 (+U226), were all greatly increased. The amounts of TNF-α, IFN-γ and IL-2 secreted by LV0007-CAR-T stimulated by the BCMA-negative K562 (+K562), were not increased.

TABLE 10

Determination Results of Cytokine Release

| Sample | IL-2 | IL-17A | IL-4 | IL-6 | IL-10 | IFN-γ | TNF-α |
|---|---|---|---|---|---|---|---|
| LV0011-CAR-T | 44.72 | 4.61 | 14.12 | 10.83 | 5.85 | 277.35 | 569.91 |
| LV0011-CAR-T + U226 | 8181.1 | 343.74 | 160.77 | 31.82 | 47.66 | 4847.04 | 3265.38 |
| LV0011-CAR-T + K562 | 117.31 | 4.1 | 3.04 | 126.72 | 0.45 | 4.25 | 942.7 |
| LV007-CAR-T | 1487.07 | 36.95 | 20.63 | 17.46 | 15.15 | 1248.25 | 986.38 |
| LV0007-CAR-T + U226 | 8181.1 | 443.26 | 96.62 | 43.42 | 48.17 | 3555.68 | 7658.65 |
| LV0007-CAR-T + K562 | 1652.22 | 18.65 | 5 | 279.96 | 10.6 | 1438.33 | 19.54 |
| T | 7.03 | N/A | 8.17 | 8.35 | 3.82 | 171.96 | 315.4 |
| T + U226 | N/A | N/A | N/A | 5.29 | 2.47 | 21.85 | 83.8 |
| T + K562 | N/A | N/A | N/A | 55.54 | N/A | N/A | 123.2 |

Example 8

Functions of CAR-T Cells from Different Donors

Figure 11:
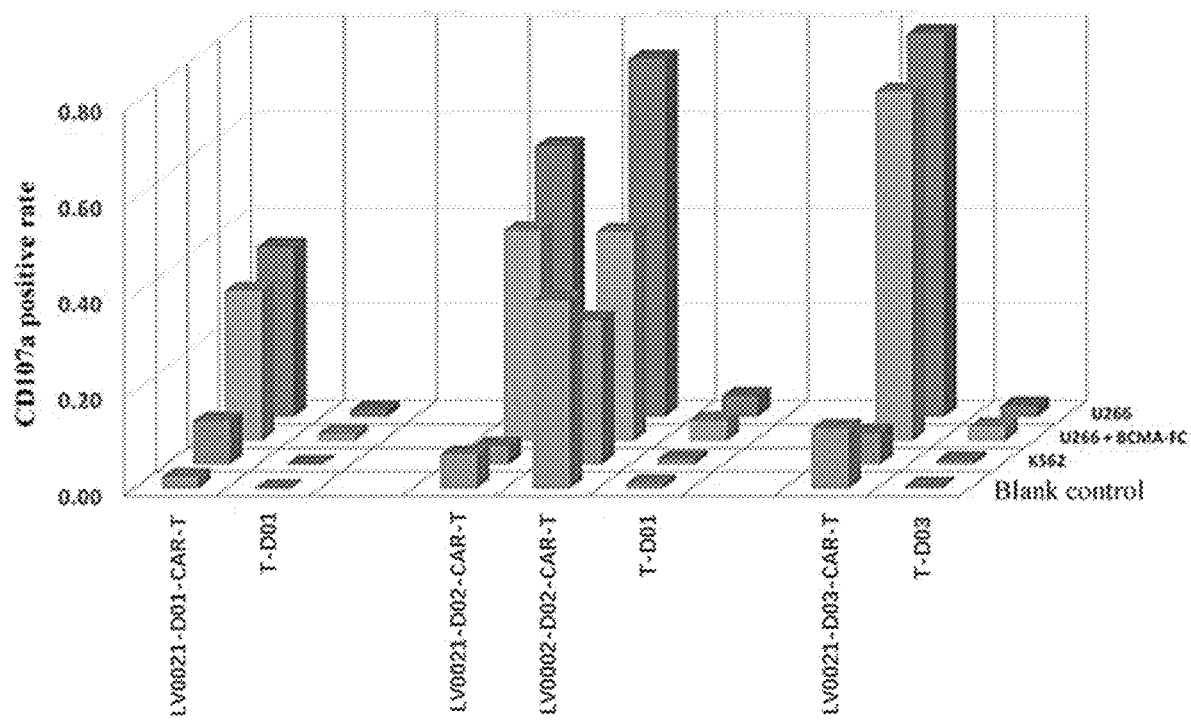
FIG. 11 shows results of function assay of CAR-T cells from different donors of the present application.

LV0002-CAR-T cells and L00021-CAR-T cells were prepared by transducing the lentiviruses LV0002 and LV0021 prepared in example 3 into CAR-T cells with a experimental method similar to example 4, wherein, LV0021 viruses (corresponding to the CAR molecule encoded by the PXL0087 plasmid, with a costimulatory factor of 4-1BB) and LV0002 viruses (corresponding to the CAR molecule encoded by the PXL0009 plasmid, with a costimulatory factor of CD28) were used to transduce T cells from different donors, for preparing CAR-T cells. T cells from donor 1 transduced with LV0002 viruses were named as LV0002-D01-CAR-T cells, T cells from donor 1 transduced with LV0002 viruses were named as LV0002-D02-CAR-T cells, and T cells from donor 3 transduced with LV0002 viruses were named as LV0002-D03-CAR-T cells; T cells from donor 1 transduced with LV0021 viruses were named as L00021-D01-CAR-T cells, T cells from donor 2 transduced with LV0021 viruses were named as L00021-D01-CAR-T cells, and T cells from donor 3 transduced with LV0021 viruses were named as L00021-D03-CAR-T cells. Meanwhile, T cells from the donor's own were adopted as controls, wherein, T cells coming from donor 1 were named as T cell-D01, T cells coming from donor 2 were named as T cell-D02, and T cells coming from donor 3 were named as T cell-D03. The functions of these CAR-T cells were also assayed by using the CD107a degranulation test in example 6. The results were shown in Table 11 and FIG. 11.

The data showed that the results for L00021-CAR-T cells from two different donors were similar, that was, the L00021-CAR-T cells of both donors could be specifically stimulated by the BCMA-positive U266 cells to produce CD107a, while the CD107a values generated under the stimulation of the BCMA-negative K562 cells were similar to the values generated under no stimulation (blank). The LV0002-CAR-T cells as a control could produce more CD107a under the stimulation of the U266 cells, which might result from the different scFvs and costimulatory factors for them. Moreover, the LV0002-CAR-T cells could have higher CD107a values under both the condition of no stimulation (blank) and the condition of K562 cell stimulation. In addition, the effect of a free BCMA protein on the capability of L00021-CAR-T to produce CD107a was minor, while the effect of a free BCMA protein on the capability of LV0002-CAR-T to produce CD107a was large.

TABLE 11

Comparison of Functions of CAR-T Cells from Different Donors

| | | CD8+/PD1−/CAR+ subpopulation | | | |
|---|---|---|---|---|---|
| Donor | Sample | U266 | U266 and BCMA | K562 | Blank control |
| Donor 1 | LV0021-D01-CAR-T | 35.2 | 31.1 | 9.10 | 2.34 |
| | T cell-D01 | 1.43 | 1.47 | 0.02 | 0.01 |
| Donor 2 | LV0021-D02-CAR-T | 56.3 | 43.6 | 3.91 | 7.13 |
| | LV0002-D02-CAR-T | 74.3 | 43.3 | 30.0 | 39.2 |
| | T cell-D02 | 4.29 | 4.24 | 1.15 | 1.01 |
| Donor 3 | LV0021-D03-CAR-T | 79.6 | 72.5 | 6.62 | 12.6 |
| | T cell-D03 | 2.25 | 3.01 | 0.86 | 0.55 |

Example 9

In-vitro Killing Assay of CAR-T on Target Cells

The CAR-T cells L00021-D02-CAR-T prepared in example 8 were used for in-vitro killing function assay which was specifically conducted by the calcein-AM fluorescence method. The steps of this assay were as follows. $5 \times 10^5$ BCMA-positive U266 cells and BCMA-negative K562 cells were respectively taken and resuspended in PBS+4% FBS solution, so that cell suspensions with density of $1 \times 10^6$ cells/ml were prepared. The U266 cells and the K562 cells were respectively marked with 25 μM of calcein-AM. The marked U266 and K562 cells were respectively inoculated into U-bottom 96-well plates according to the quantity of 5000 cells per well; the to-be-assayed CAR-T cells or T cells as the control were then respectively added to the corresponding wells according to the effector cell/target cell ratios of 50:1, 25:1 and 5:1 (E:T value), and the solution volume in each well was 200 μl. In addition, a PBS solution, instead of the effector cells, was added to the U266 or K562 cells, serving as a negative control for the assay; and the cell lysis solution, in place of the effector cells, was added to the U266 or K562 cells, serving as a positive control for assay. Then, the U-bottom 96-well plates were incubated in the dark at 37° C. for 3 hours, and the supernatant solution was pipetted (with no cells being pipetted) from each well for fluorescence assay (excitation wavelength: 485/20 nm; emission wavelength: 530/25 nm). The relative proportion of the target cells (U266 or K562) which were killed by the effector cells and lysed to release calcein-AM can be calculated by the following formula:

$$\text{dissolution proportion (\%)} = \frac{F_{test} - F_{spont.}}{F_{max.} - F_{spont.}}$$

wherein, $F_{test}$ was an average fluorescence value for the replicate wells containing the target cells and the to-be-assayed T/CAR-T cells, $F_{spont.}$ was an average fluorescence value for the replicate wells containing the target cells and PBS, and $F_{max.}$ was an average fluorescence value for the replicate wells containing the target cells and the lysis solution.

Figure 12:
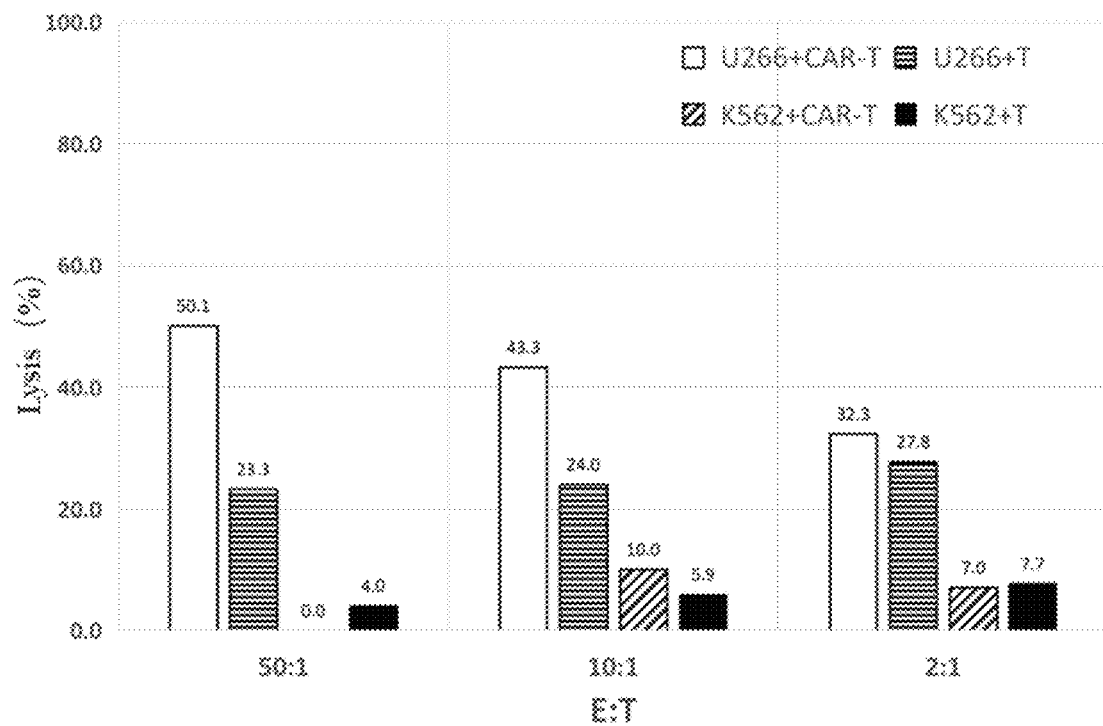
FIG. 12 shows in-vitro killing effects of CAR-T cells of the present application against target cells.

Taking the L00021-D02-CAR-T sample as an example, the in-vitro killing effect of the CAR-T cells against the target cells was shown in FIG. 12. The CAR-T cells had a strong killing effect against the BCMA-positive U266 cells, and the killing effect was enhanced as the E:T value increases, showing that a higher proportion of U266 cells were lysed to release calcein-AM. As a contrast, the CAR-T cells had a poor killing effect against the BCMA-negative K562 cells. In addition, the T cells had a certain degree of nonspecific killing effect against the U266 cells, and the nonspecific killing effect would not be changed as the E:T value increases. Therefore, the CAR-T cells had a remarkable BCMA-specific killing effect.

Example 10

Tumor Suppression Assay in Tumor-Bearing Animal Models

The CAR-T cells (L00021-D02-CAR-T) coming from donor 2 which were prepared in example 8 were used for the animal model experiment. The L00021-CAR-T cells were named as XL103-07. Meanwhile, T cells coming from donor 2 (T cell-D02) were adopted as control T cells. Proliferating U266 cells were subcutaneously injected into immunodeficient NSG mice in a quantity of $2 \times 10^6$ cells per mouse, creating a U266 subcutaneous tumor-bearing model. When the tumor sizes reached 100-150 mm³, the tumor-bearing mice were divided into five groups according to Table 12, and the CAR-T cells (XL103-07), the control T cells (T cell-D02), PBS or cell cryopreservation medium containing 7.5% of DMSO, 23% of human serum albumin, 32.5% of compound electrolyte solution, 35% of glucose injection and 2% of normal saline) were injected into the tumor-bearing mice respectively. The grouping and an administration regimen were shown in Table 12.

TABLE 12

Grouping Solution for Animal Model Experiment

| Group | Number | CAR-T information | Administration method | Administration Dosage | Frequency of administration |
|---|---|---|---|---|---|
| 1 | 5 | PBS control | I.V. | 100 µl | single administration |
| 2 | 5 | control T cell | I.V. | 10 × 10⁶ cells/animal | single administration |
| 3 | 5 | CAR-T cell (low-dosage group) | I.V. | 2 × 10⁶ cells/animal | single administration |
| 4 | 5 | CAR-T cell (high-dosage group) | I.V. | 10 × 10⁶ cells/animal | single administration |
| 5 | 5 | cell cryopreservation medium | I.V. | 100 µl | single administration |

Figure 13:
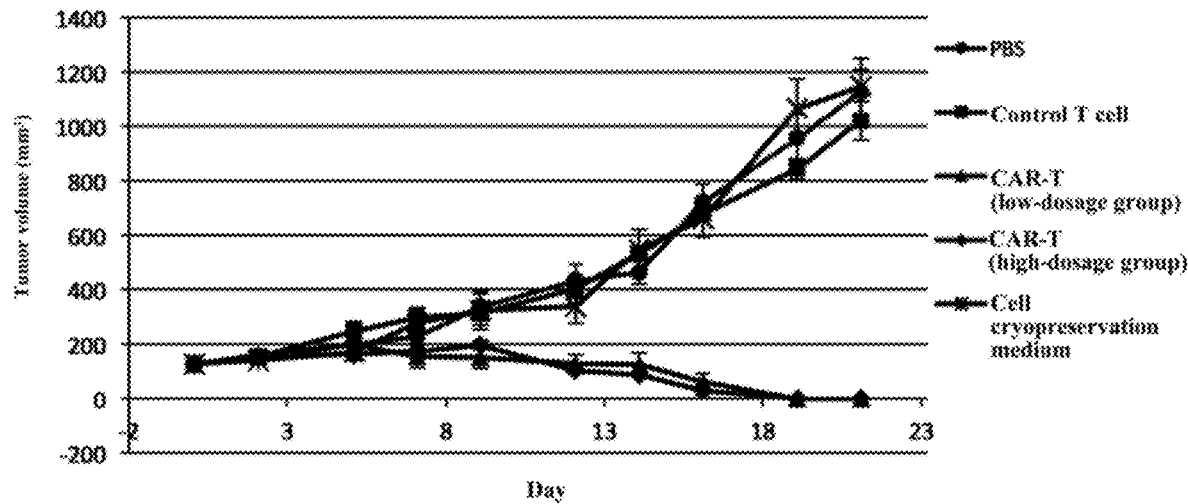
FIG. 13 shows results of tumor-bearing mouse model experiment for the tumor-killing effects of CAR-T cells of the present application.

The mice were continuously fed, and the tumor sizes, the mouse weights and the survival states of the mice were recorded. The results were shown in FIG. 13. The results of the mouse model experiment indicated that the high-dosage group and the low-dosage group both showed a good tumor-killing effect after a single injection of the CAR-T cells, and that 19 days after the injection, the tumors completely disappeared. On the contrary, the tumors in the mice for which injected the control T cells, PBS or the cell cryopreservation medium continued to grow.

Example 11

Assay for Cytokines in Tumor-Bearing Animal Models

The same CAR-T cells XL103-07 as those in example 10 were used to detect the changes of cytokines (IFNγ, IL2, IL10, IL7, IL6 and TNF-α) in the peripheral blood plasma of mice administrated drugs by the cytometric beads array method (the specific method can be found in BD™ CBA Flex Set Reagents and BD FACS Array™ Bioanalyzer). The tumor-bearing mice were divided into three groups: a control T cell group, an XL103-07 high-dosage group and an XL103-07 low-dosage group, and there were five tumor-bearing mice in each group. XL103-07-H represents the high-dosage group, and the dosage was 10×10⁶ cells (XL103-07 cells)/animal; XL103-07-L represented the low-dosage group, and the dosage was 2×10⁶ cells (XL103-07 cells)/animal.

Figure 14:
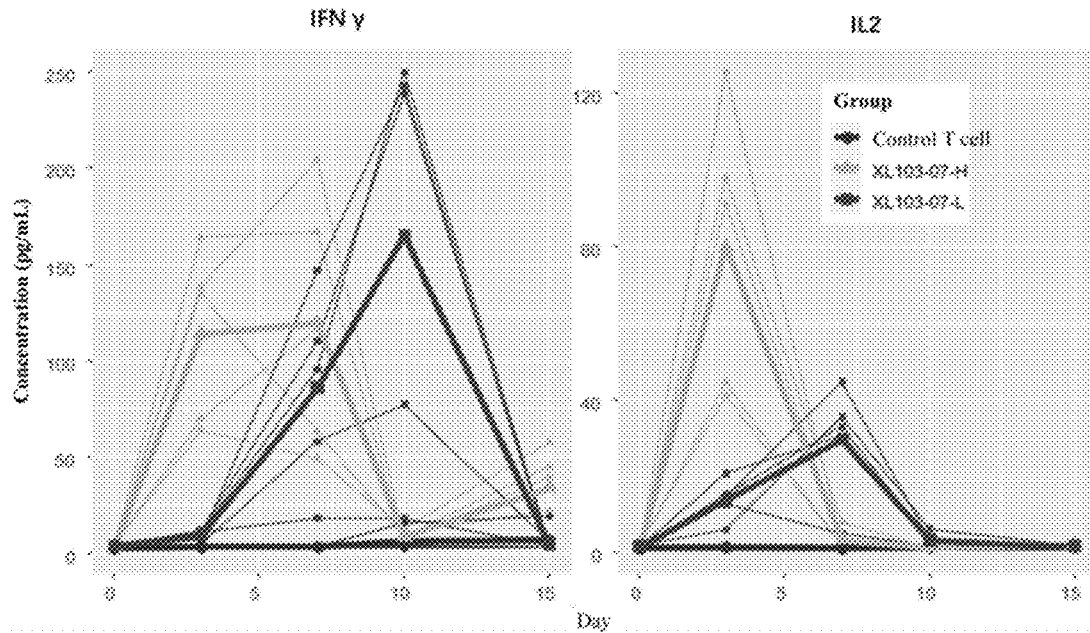
FIG. 14 and FIG. 15 show changes of cytokines in tumor-bearing mouse models administrated with the CAR-T cells of the present application.

The results for IFNγ and IL2 were shown in FIG. 14. The results showed that the peaks of IFN-γ and IL2 in the mice of the low-dosage group appeared on day 10 and day 7 respectively; and that the peaks of IFNγ and IL2 in the high-dosage group appeared on day 3-7 and day 3 respectively, wherein the peak appearing times were earlier than that of the low-dosage group. The level of the control T cell group was low, without an obvious tendency of change.

Figure 15:
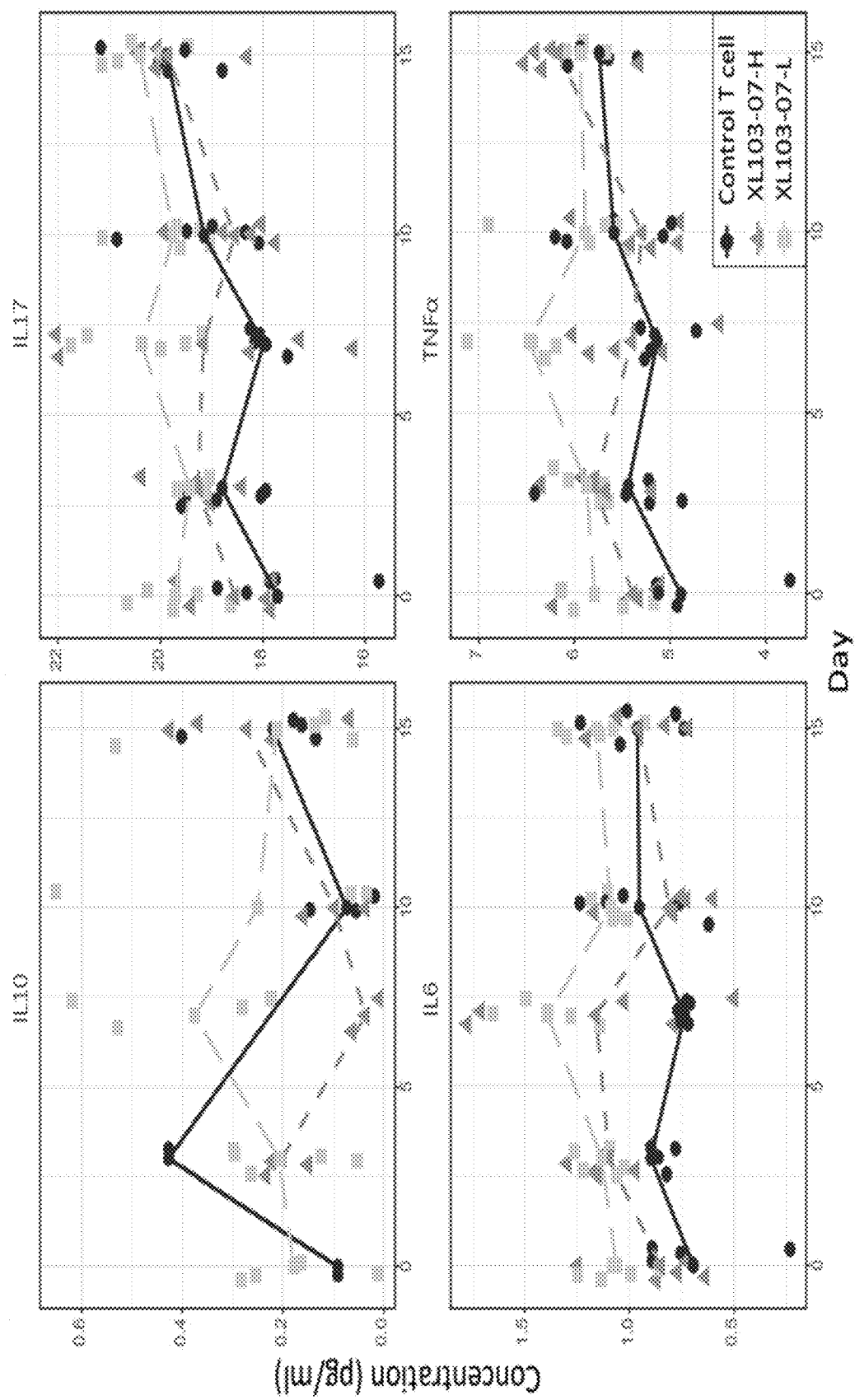

The results for IL10, IL7, IL6 and TNF-α were shown in FIG. 15. The results in FIG. 15 showed that all the cytokine levels were low and did not have an obvious tendency of change in comparison with that of the control T cell group.

Example 12

Figure 16:
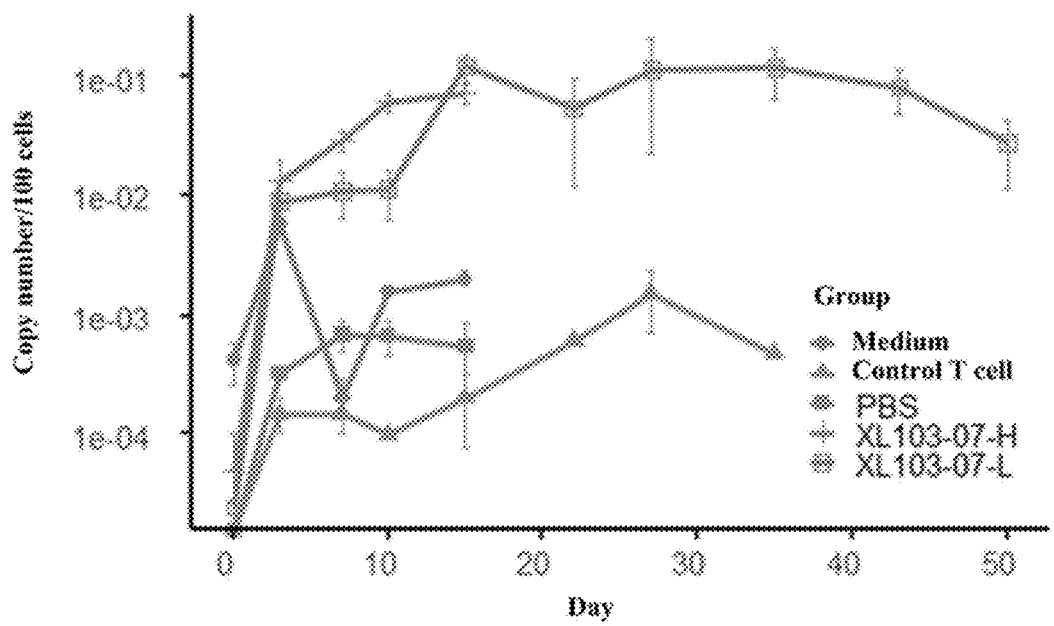
FIG. 16 shows changes of the CAR copy numbers in the peripheral blood of tumor-bearing mouses administrated with the CAR-T cells of the present application.

Assay for Changes of Copy Numbers of CAR Molecules in Tumor-Bearing Animal Models With the quantitative PCR method, the changes of the DNA copy numbers of the CAR molecules of XL103-07 in the genomic DNA of the peripheral blood cells of the tumor-bearing mice animal model in example 10 were detected and the proliferation situations of the CAR-T cells in the mice were analyzed. The results were shown in FIG. 16. Similarly, the tumor-bearing mice were divided into three groups: a control T cell group, an XL103-07 high-dosage group and an XL103-07 low-dosage group, and there were five tumor-bearing mice in each group. XL103-07-H represented the high-dosage group, and the dosage was $10 \times 10^6$ cells (XL103-07 cells)/animal; XL103-07-L represented the low-dosage group, and the dosage was $2 \times 10^6$ cells (XL103-07 cells)/animal.

The results showed that in comparison with that of the control T cell group, the CAR copy number for the high-dosage group started to raise on day 3, and the peak was achieved on day 10 and maintained until day 15. On the contrary, there was no proliferation in Mock-T and other control groups. This indicates that the CAR-T cells were proliferated in a large amount in the tumor killing process.

Example 13

Exploratory Clinical Research

After the stable production process for the plasmid PXL0085, the lentiviral vector LV0020 and the CAR-T cells were obtained by a pharmaceutical research, we carried out an exploratory clinical research to investigate their safety, tolerance and preliminary effectiveness and to explore PK/PD characteristics. The GCP principles were followed in this research in terms of experimental sample preparation, researchers and research institutions, experimental schemes, processes for ethical review and informed consent, enrollment screening as well as diagnosis and treatment for subjects, reporting and treatment of adverse reactions, collection and statistic analysis of experimental data, etc.

Figure 17:
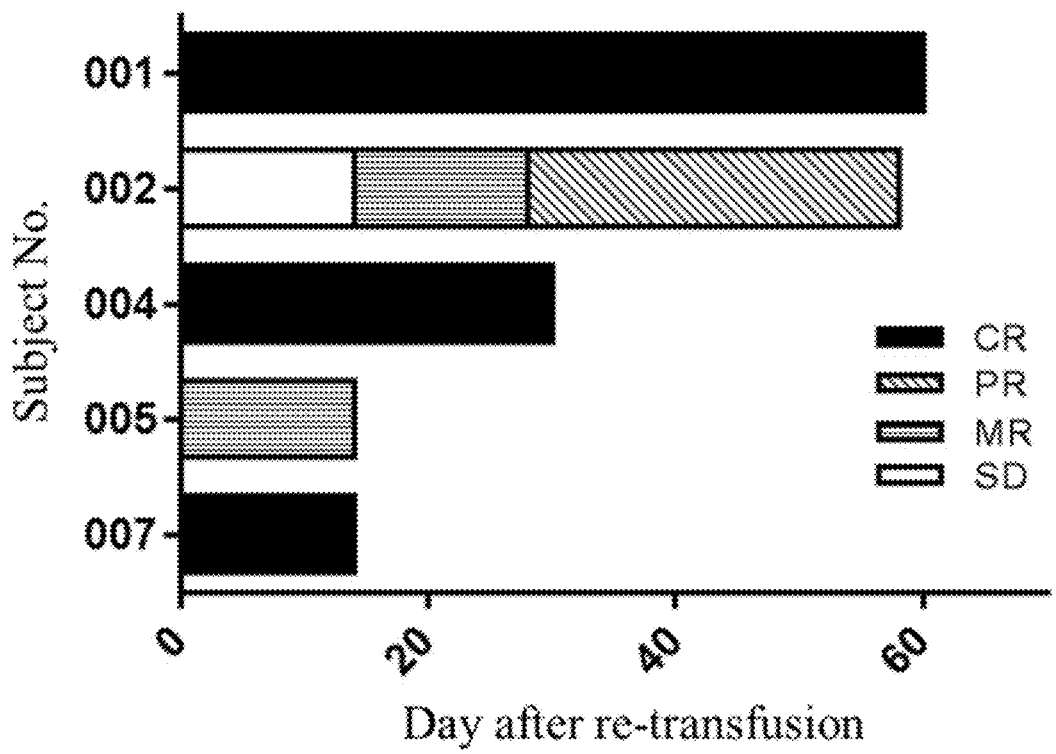
FIG. 17 shows the evaluation for the therapeutic effects of the CAR-T cells of the present application in bodies of the subjects in need.

A total of five subjects (respectively numbered as 001, 002, 004, 005 and 007) with relapsing/refractory multiple myeloma were enrolled and treated in the clinical research. The therapeutic effect was evaluated according to the response criteria for multiple myeloma recommended by the International Myeloma Working Group (IMWG) 2016. The best overall response rate for the five subjects reached 100%. Three of the subjects completely responded, one subject partially responded, one subject minimally responded, and the responses of the PR and MR subjects were continuously enhanced (FIG. 17).

Example 14

Assay for DNA Copy Number of CAR in Subjects

Figure 18:
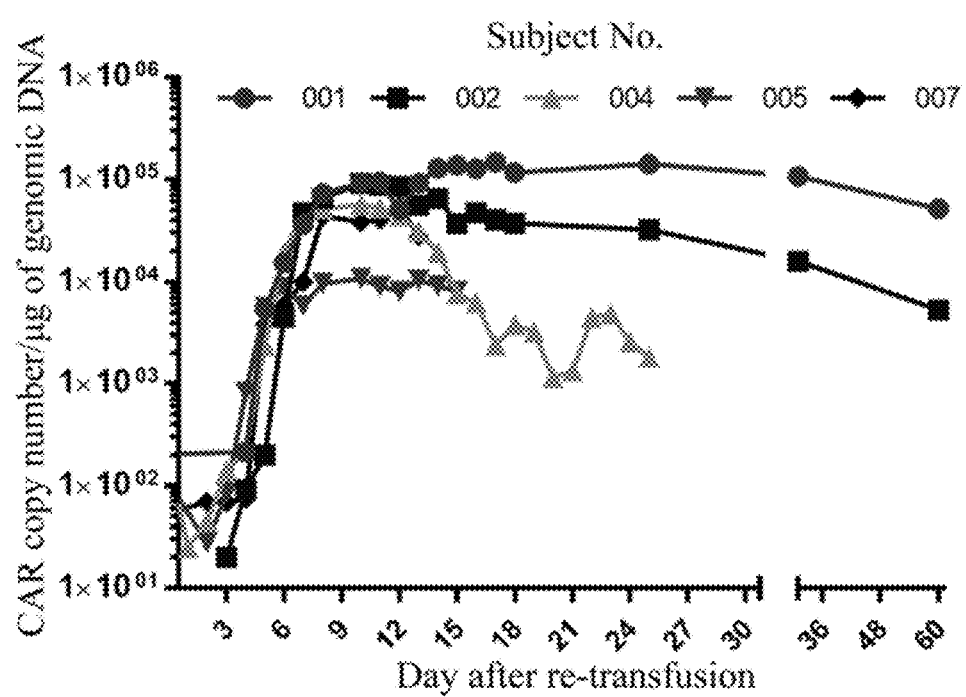
FIG. 18 shows changes of the CAR copy numbers in the peripheral blood in vivo of the subjects of the present application.

The DNA copy numbers of the CAR in the peripheral blood of the five subjects in example 13 was detected by using the droplet digital PCR method (see Bio-Rad QX200 Description), to evaluate the pharmacokinetic characteristics of the CAR-T cells. The result was shown in FIG. 18. After administrated, the product was rapidly proliferated in vivo, and could still be detected 60 days after administration. The time to peak of the CAR-T in most of the subjects was approximately 10 days, and the time to peak of the CAR-T in subject 001 was the 17 days.

Example 15

Pharmacokinetic Analysis in Subjects

With NonCompart package of the R 3.5.0 software, the changes of the DNA copy numbers of the CAR in example 14 were further analyzed and pharmacokinetics-related parameters were calculated. The results were shown in Table 13. In Table 13, T0 represents a time when the nonzero concentration was initially observed, peak concentration of drug (Cmax) represented a maximum peak for drug concentration, time to peak (Tmax) represented a time needed to reach a peak concentration of drug, AUC (0-28) represented an integral area under the curve from day 0 to day 28, and AUC (0-CLST) represented an integral area under the curve from 0 to final observation time.

TABLE 13

Pharmacokinetic Research and Analysis

| Subject No. | T0 (day) | Peak concentration of drug (Cmax) (copy number/μg DNA) | Time to peak (Tmax) (day) | AUC (0-28) | AUC (0-CLST) |
|---|---|---|---|---|---|
| 001 | 1 | 148182 | 17 | 2449678 | 5004465 |
| 002 | 2 | 91250 | 10 | 1050197 | 1389729 |
| 004 | 0 | 56500 | 10 | 420084.9 | 417261.2 |
| 005 | 1 | 10725 | 10 | 142147.7 | 92527.47 |
| 007 | 1 | 54250 | 12 | 493486.2 | 251114 |

The results showed that the first dosage group had an average Cmax of (98644±5000) copy number/μg DNA and an average AUC (0-28) of (1306653.3±100000); and the second dosage group had an average Cmax of (32487.5±2000) copy number/μg DNA and an average AUC (0-28) of (317816.95±150000).

The aforementioned detailed description is provided in an explanatory and illustrative manner rather than intended to limit the scope of the appended claims. So far, a variety of variations of the embodiments illustrated in the present application are apparent to those of ordinary skill in the art, and are kept within the scope of the appended claims and equivalent embodiments thereof.

What is claimed is:

1. A chimeric antigen receptor (CAR), wherein the CAR comprises a B-cell maturation antigen (BCMA) binding domain, a transmembrane domain, a costimulatory domain and an intracellular signal transduction domain, the BCMA-binding domain comprises an antibody or a fragment thereof capable of specifically binding-a BCMA protein, and the antibody comprises a heavy chain complementary determining region 1 (HCDR1), a heavy chain complementary determining region 2 (HCDR2) and a heavy chain complementary determining region 3 (HCDR3), wherein the HCDR1 comprises the amino acid sequence of SEQ ID NO: 9, the HCDR2 comprises the amino acid sequence of SEQ ID NO: 10, and the HCDR3 comprises the amino acid sequence of SEQ ID NO: 11; and wherein the antibody comprises a light chain complementary determining region 1 (LCDR1), a light chain complementary determining region 2 (LCDR2) and a light chain complementary determining region 3 (LCDR3), and wherein the LCDR1 comprises the amino acid sequence of SEQ ID NO: 17, the LCDR2 comprises the amino acid sequence of SEQ ID NO: 18, and the LCDR3 comprises the amino acid sequence of SEQ ID NO: 19.

2. The CAR of claim 1, wherein the antibody comprises a heavy chain variable region, and the heavy chain variable region comprises the amino acid sequence of SEQ ID NO: 7.

3. The CAR of claim 1, wherein the antibody comprises a light chain variable region, and the light chain variable region comprises the amino acid sequence of SEQ ID NO: 15.

4. The CAR of claim 1, wherein the antibody is a single-chain antibody fragment.

5. The CAR of claim 1, wherein the antibody comprises the amino acid sequence of SEQ ID NO: 43.

6. The CAR of claim 1, wherein the transmembrane domain comprises a transmembrane domain from a protein selected from a group consisting of σ, β or ζ chain of the T cell receptor, CD28, CD3e, CD45, CD4, CD5, CD8a, CD9, CD16, CD22, CD33, CD37, CD64, CD80, CD86, CD134, CD137 and CD154.

7. The CAR of claim 1, wherein the transmembrane domain comprises the amino acid sequence of SEQ ID NO: 27.

8. The CAR of claim 1, wherein the costimulatory domain comprises a costimulatory domain from a protein selected from a group consisting of CD28, 4-1BB, OX-40 and ICOS.

9. The CAR of claim 1, wherein the costimulatory domain comprises the amino acid sequence of SEQ ID NO: 29 or SEQ ID NO: 31.

10. The CAR of claim 1, wherein the intracellular signal transduction domain comprises a signal transduction domain from CD3t.

11. The CAR of claim 1, wherein the intracellular signal transduction domain comprises the amino acid sequence of SEQ ID NO: 33.

12. The CAR of claim 1, wherein the CAR further comprises a hinge region linking the BCMA-binding domain to the transmembrane domain.

13. The CAR of claim 1, wherein the CAR is further linked to a signal peptide.

14. The CAR of claim 1, comprising the amino acid sequence of SEQ ID NO: 49 or SEQ ID NO: 51.

15. An isolated nucleic acid molecule, encoding the CAR of claim 1.

16. A vector, comprising the nucleic acid molecule of claim 15.

17. A method of preparing an immune effector cell, comprising introducing the vector of claim 16 into the immune effector cell.

18. An immune effector cell, comprising the CAR of claim 1.

19. A composition, comprising the immune effector cell of claim 18.

20. A method for treating a plasmocyte malignancy disease, comprising administering the CAR of claim 1.

21. The use method of claim 20, wherein the plasmocyte malignancy disease is a multiple myeloma.

* * * * *

UNITED STATES PATENT AND TRADEMARK OFFICE
CERTIFICATE OF CORRECTION

PATENT NO. : 11,026,975 B2
APPLICATION NO. : 16/650327
DATED : June 8, 2021
INVENTOR(S) : Jianfeng Zhou et al.

Page 1 of 1

It is certified that error appears in the above-identified patent and that said Letters Patent is hereby corrected as shown below:

In the Claims

Column 75, Claim 1, Line 6, delete the "-" between "binding" and "a".

Column 76, Claim 10, Line 3, "CD3t" should be "CD3ζ".

Signed and Sealed this
Twenty-seventh Day of July, 2021

Drew Hirshfeld
*Performing the Functions and Duties of the*
*Under Secretary of Commerce for Intellectual Property and*
*Director of the United States Patent and Trademark Office*